(12) United States Patent
Vidalis et al.

(10) Patent No.: US 10,898,116 B2
(45) Date of Patent: Jan. 26, 2021

(54) METHODS OF MANUFACTURE TO OPTIMIZE PERFORMANCE OF TRANSDERMAL SAMPLING AND ANALYSIS DEVICE

(71) Applicant: Flexible Medical Systems LLC, Rockville, MD (US)

(72) Inventors: Joseph J Vidalis, Bethesda, MD (US); Joseph A Marcanio, Greensburg, PA (US); John Frederick Currie, Bethesda, MD (US); Helena Woodvine Snyder, Washington, DC (US); Vikas Bhatia, Gaithersburg, MD (US)

(73) Assignee: Cambridge Medical Technologies LLC, Carson City, NV (US)

( * ) Notice: Subject to any disclaimer, the term of this patent is extended or adjusted under 35 U.S.C. 154(b) by 997 days.

(21) Appl. No.: 14/208,344

(22) Filed: Mar. 13, 2014

(65) Prior Publication Data

US 2014/0275895 A1    Sep. 18, 2014

Related U.S. Application Data

(60) Provisional application No. 61/791,970, filed on Mar. 15, 2013.

(51) Int. Cl.
*A61B 5/15* (2006.01)
*A61B 5/1486* (2006.01)
(Continued)

(52) U.S. Cl.
CPC ...... *A61B 5/150076* (2013.01); *A61B 5/1486* (2013.01); *A61B 5/14532* (2013.01);
(Continued)

(58) Field of Classification Search
CPC .................................................. A61B 5/157
See application file for complete search history.

(56) References Cited

U.S. PATENT DOCUMENTS 6,022,316 A *  2/2000  Eppstein ............ A61N 1/0416
                                                    600/309
6,233,471 B1 * 5/2001  Berner .............. A61B 5/14532
                                                    600/345
(Continued)

FOREIGN PATENT DOCUMENTS

WO    2009/042631 A2    4/2009

OTHER PUBLICATIONS

Xu, Electrochemical detection optimized for capillary liquid chromatographic determination of neuroactive compounds, 2012, Doctoral Dissertation, University of Pittsburgh, Web, Retrieved from: http://d-scholarship.pitt.edu/10478/.*

(Continued)

*Primary Examiner* — Michael R Bloch
(74) *Attorney, Agent, or Firm* — The Marbury Law Group, PLLC

(57) ABSTRACT

Methods and systems for manufacturing a transdermal sampling and analysis device for non-invasively and transdermally obtaining biological samples from a subject and determining levels of analytes of the obtained biological samples are provided. A method of manufacturing the device may improve performance and includes forming channel structures on the lid of the device, thereby making the spacer/channel support structures physically independent and separable from the sensing electrode. Other methods of manufacturing the device may improve performance and include forming at least one of the electrodes on each of the base and the lid, and forming a recessed second spacer layer over the channel support structures, thereby separating the (Continued)

channel support structures and the electrode on the lid to allow a larger area of the electrode to be exposed to the biological sample.

13 Claims, 43 Drawing Sheets

(51) Int. Cl.
*A61B 5/145* (2006.01)
*A61B 5/157* (2006.01)
*A61B 5/151* (2006.01)
(52) U.S. Cl.
CPC ........ *A61B 5/157* (2013.01); *A61B 5/150022* (2013.01); *A61B 5/15134* (2013.01); *A61B 5/150274* (2013.01); *A61B 5/150862* (2013.01)

(56) References Cited

U.S. PATENT DOCUMENTS

| | | | | |
|---|---|---|---|---|
| 6,393,318 B1 * | 5/2002 | Conn | ................... | A61B 5/1486 604/20 |
| 6,436,078 B1 * | 8/2002 | Svedman | ........... | A61B 5/14521 604/289 |
| 2002/0055704 A1 * | 5/2002 | Scott | ................... | A61N 1/0436 604/20 |
| 2003/0003524 A1 * | 1/2003 | Taniike | ................ | A61B 5/1486 435/25 |
| 2003/0100846 A1 * | 5/2003 | Custer | ................ | A61B 5/14514 600/573 |
| 2003/0214304 A1 | 11/2003 | Karinka et al. | | |
| 2004/0224369 A1 * | 11/2004 | Cai | ................... | G01N 27/3272 435/7.7 |
| 2005/0175505 A1 * | 8/2005 | Cantor | ............. | B01L 3/502707 422/68.1 |
| 2005/0182307 A1 | 8/2005 | Currie et al. | | |
| 2005/0228340 A1 | 10/2005 | Cleary et al. | | |
| 2009/0308742 A1 * | 12/2009 | Paranjape | ............ | A61B 5/0537 204/403.1 |
| 2012/0150004 A1 | 6/2012 | Currie et al. | | |
| 2013/0144142 A1 * | 6/2013 | Vidalis | ................ | A61B 5/1486 600/347 |
| 2014/0135679 A1 * | 5/2014 | Mann | ..................... | A61N 1/325 604/20 |

OTHER PUBLICATIONS

International Search Report and Written Opinion issued for International Application No. PCT/US2014/027362, dated Sep. 1, 2014.

\* cited by examiner

METHODS OF MANUFACTURE TO OPTIMIZE PERFORMANCE OF TRANSDERMAL SAMPLING AND ANALYSIS DEVICE

RELATED APPLICATIONS

This application claims priority to U.S. Provisional Patent Application No. 61/791,970 entitled "Methods of Manufacture to Optimize Performance of Transdermal Sampling and Analysis Device" filed on Mar. 15, 2013, the entire contents of which are hereby incorporated by reference for all purposes.

BACKGROUND

Effective diagnoses and treatment of diseases depend on accurate monitoring of the current physiological state of a subject. Monitoring the concentration of molecules in the body is an example of a method for determining the physiological state. For example, diabetics must actively monitor their body's glucose levels to treat and prevent potentially life threatening conditions such as hypo- or hyperglycemia.

Monitoring the internal physiological state of a subject requires a two step process. First, biological samples must be obtained from the body of the subject. Second, the sample must be analyzed using any of a variety of methods and systems. Some common methods and systems that may be used to analyze samples obtained from a subject include using assays, sensors and/or biosensors.

Biosensors combine a biological component with a physiochemical detector component to allow for the detection of analytes in biological samples. An analyte is a substance or chemical constituent that is determined in an analytical procedure. For example, glucose is the analyte in the process used in the blood glucose biosensors. Biosensors can be used for detecting or determining characteristics of any kind of analyte that can be analyzed by biological means.

A typical biosensor may include three main parts: i) Biologically reactive elements such as biological materials (e.g., tissues, microorganisms, organelles, cell receptors, enzyme, antibodies, and take acid, etc.), a biologically derived material or biomimic. The sensitive biological elements may be created by biological engineering; ii) a transducer or detector elements which work in a physiochemical way (e.g., optical, piezoelectric, electrochemical, etc.), that may transform the signal resulting from the interaction of the analyte with the biological elements into another signal that can be more easily measured and quantified; and iii) associated electronics or signal processors that are primarily responsible for the display of the results in a user-friendly way.

A common commercial biosensor is the blood glucose biosensor. A blood glucose biosensor may measure current produced by the enzymatic oxidation of glucose in an electrochemical cell. The current generated may be proportional to the concentration of glucose, given that it is the limiting reactant. For this reaction, the enzyme glucose oxidase converts glucose to gluconolactone, releasing electrons in the process. These electrons are transferred to the anode of the electrochemical cell by an electron mediator such as ferricyanide, thus generating a measurable current proportional to the glucose concentration. The generated current is run through an ammeter, then returned through the cathode of the electrochemical cell Biological samples may be obtained using different methods, such as by swabs or transdermally.

Swabbing is a non-invasive method for collecting biological samples from surfaces of the epithelium. This method is used to collect cells or organisms that may be used in testing for genetic traits, monitoring for cancer and detecting the presence of bacteria.

Conventional methods for obtaining biological samples are typically painful and invasive. For example, to determine blood glucose levels, diabetics must draw blood by puncturing or lacerating their skin to draw blood using a sharp instrument. This procedure may be uncomfortable, painful, and especially irritating when it has to be performed multiple times a day in the case of diabetics. In addition to pain and discomfort, there are other undesirable side effects associated with these invasive tissue extraction techniques. For example, diabetics who also suffer from hemophilia face the danger of severe hemorrhage every time they have to test their blood glucose levels using invasive procedures. In another example, these invasive procedures expose immuno-compromised diabetics to increased chances of local or systemic infections.

The currently available biosensors are also designed in a manner to require a relatively large sample to accurately determine analyte concentration. For example, the currently available blood glucose biosensors require at least 300 nl of blood in order to analyze the blood glucose levels. To obtain these larger biological samples, painful and invasive procedures must be employed, which are not desirable.

Therefore, additional research may be required to provide a non-invasive, pain-free procedure which requires a small sample to perform accurate analysis. Transdermal collection of biological samples which permits the non-invasive obtaining of samples from below the epithelial surface is desired. To obtain samples transdermally, the epithelium may be breached without lacerating or puncturing of the skin.

A novel, one-step home monitoring glucose biosensor may provide effective in situ measurement of glucose concentration from small quantities of the interstitial fluid collected from the capillary-like channels of the patient's skin. This system (referred to herein as the "transdermal sampling and analysis device" or "transdermal glucose biosensor") is described in U.S. patent application Ser. No. 13/294,368, entitled "Transdermal Sampling and Analysis Device" and in U.S. patent application Ser. No. 13/688,954, entitled "Anti-Interferent Barrier Layers for Non-Invasive Transdermal Sampling and analysis Device", the contents of both are hereby incorporated by reference for the purpose of describing the systems and methods disclosed therein.

SUMMARY OF THE INVENTION

The various embodiment methods produce a transdermal sampling and analysis device with increased accuracy of the glucose sensing. The improved accuracy may result from a manufacture process that results in more uniform layer of analyte sensing reagent (for example, a biologically reactive element) used therein. The various embodiment methods may implement channel and reservoir configurations that prevent the analyte sensing reagent from blocking the flow through channels of a collected sample to be analyzed.

Some embodiment methods may include forming a base structure with at least one counter electrode, a first spacer layer with a plurality of channel support structures, and a second spacer layer formed over the first spacer layer, forming a lid configured to be positioned above the second spacer layer, and attaching the lid to the base structure, in which attaching the lid to the base structure forms a plurality of channels in a reservoir between the plurality of channel support structures. In some embodiments, the lid has at least one sensing electrode and an analyte sensing layer. In some embodiments, the second spacer layer is recessed back from an edge of the plurality of channel support structures.

BRIEF DESCRIPTION OF THE DRAWINGS

The accompanying drawings, which are incorporated herein and constitute part of this specification, illustrate exemplary aspects of the invention, and together with the general description given above and the detailed description given below, serve to explain the features of the invention.

DETAILED DESCRIPTION

Figure 1:
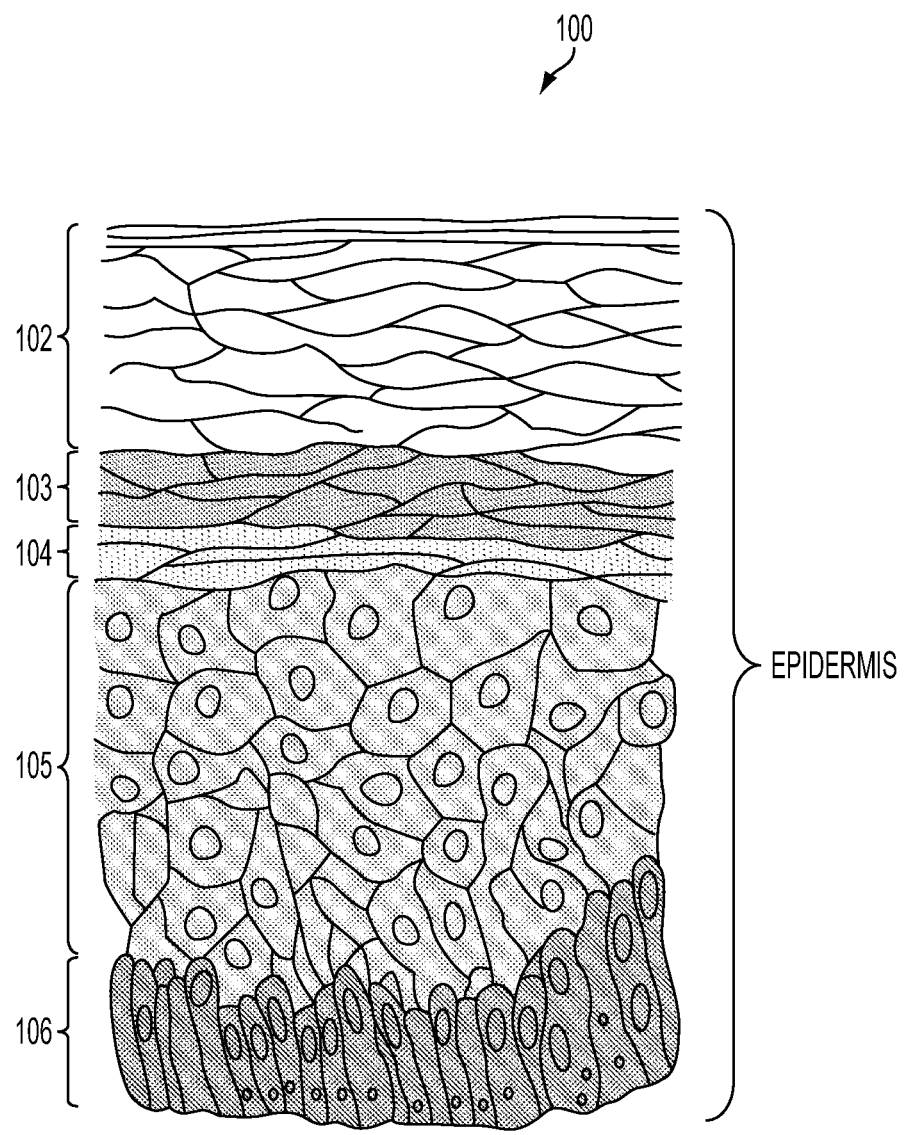
FIG. 1 illustrates a cross-sectional view of epithelium layer of human skin.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the disclosure or the claims. Alternate embodiments may be devised without departing from the scope of the disclosure. Additionally, well-known elements of the disclosure will not be described in detail or will be omitted so as not to obscure the relevant details of the disclosure.

The words "exemplary" and/or "example" are used herein to mean "serving as an example, instance, or illustration." Any embodiment described herein as "exemplary" and/or "example" is not necessarily to be construed as preferred or advantageous over other embodiments.

The word "approximately" as used herein with respect to certain dimensions means within ten percent of the dimension, including within five percent, within two percent and within one percent of the corresponding dimension.

Conventional methods for obtaining biological samples from a subject are invasive, uncomfortable, and painful. For example, conventional glucose biosensors require that diabetics obtain blood samples by puncturing or lacerating their skin using a sharp blade or pin. The blood sample may then collected and delivered to a biosensor which detects glucose levels of the sample blood. While such biosensors are often marketed as being "pain-free," users often experience some degree of discomfort that they may become inured to over repeated samplings. Regardless, conventional biosensors may cause discomfort, pain and may increase the chances of infection or bleeding.

Another disadvantage of the conventional biosensors is that they require several steps before they can analyze a biological sample. Conventional biosensors require breaching the skin, collecting the biological samples (e.g., blood), and delivering the obtained samples from the site of collection to the analyzing device. This multi-step process is time consuming and may cause contamination or loss of the biological sample during the collection and/or delivery. Additionally, if the sharp instruments that are used to breach the epithelium are not disposed of properly, cross-contamination of diseases, such as hepatitis, may result when other persons come in contact with the contaminated sharp instrument. A further disadvantage of the current biosensors is that they require relatively large sample volumes to provide accurate results.

Thus, various embodiment methods and apparatus are disclosed which provide for a safe and non-invasive transdermal sampling, and analysis of biological samples. The various embodiment methods and apparatus obtain and analyze transdermally extracted biological samples with minimal injury or sensation. In addition, the various embodiments obtain biological samples and deliver the samples to a biological sensor in a single step. Thus, potential risk of contamination may be minimized. In an embodiment, a voltage (or current) may be applied to a disruptor unit creating a localized heat that may be applied to the epithelium (i.e., skin) of a subject. The applied localized heat has been found to alter the permeability of the cells at a disruption site in the stratum corneum layer of the epithelium such that channels for fluid flow are created.

Interstitial fluid may permeate from these capillary-like channels and may be collected. The collected fluids may be tested for an analyte, such as glucose, by reacting the collected fluids with a biologically reactive element, such as an enzyme. The products of the biochemical reaction between the biological sample and the biologically reactive element may be analyzed electrochemically to deduce the concentration of the reactant from either a potential or an electrical current. The amount of potential or current that is detected may be mapped to determine levels of analytes or characteristics of the biological sample. Once the disruptor unit is removed from the skin, stratum corneum cells become impermeable again by returning to their original formation and closing the capillary-like channels.

The various embodiment methods and apparatus further allow for accurate real-time analysis of very small amounts of biological samples. In an embodiment, minute quantities of the interstitial fluid collected from the capillary-like channels of the stratum corneum may be used to determine various analyte levels.

The various embodiment methods and apparatus further enable the entire process of analyzing a biological sample including disrupting the skin cells, collecting biological samples, reacting the biological sample with a biologically reactive element, and sensing the signals generated by the reaction in singular device. By incorporating a sampling device and analyzing device in a singular package, a smaller biological sample may be required and the potential for contamination of the biological sample may be dramatically reduced. The time required to obtain a sample and perform an analysis of the sample may be also reduced.

Transdermal extraction of biological samples may require accessing body fluid that may be located under an intact skin surface. The skin is a soft outer covering of an animal, in particular a vertebrate. In mammals, the skin is the largest organ of the integumentary system made up of multiple layers of ectodermal tissue, and guards the underlying muscles, bones, ligaments and internal organs. Skin performs the following functions: protection, sensation, heat regulation, control of evaporation, storage and synthesis, absorption and water resistance.

Mammalian skin is composed of three primary layers: the epidermis, which provides waterproofing and serves as a barrier to infection; the dermis, which serves as a location for the appendages of skin; and the hypodermis (subcutaneous adipose layer).

Epidermis is the outermost layer of the skin. It forms the waterproof, protective wrap over the body's surface and is made up of stratified squamous epithelium with an underlying basal lamina. Epidermis is divided into several layers where cells are formed through mitosis at the innermost layers. They move up the strata changing shape and composition as they differentiate and become filled with keratin. They eventually reach the top layer called stratum corneum and are sloughed off, or desquamated. The thickness of the epidermis is about 0.5 to 1.5 mm.

As illustrated in FIG. 1, epidermis is divided into the following five sub-layers or strata: Stratum corneum 102 which consists of 25 to 30 layers of dead cells and has a thickness between 10 μm and 50 μm; Stratum lucidum 103, Stratum granulosum 104, Stratum spinosum 105, and Stratum germinativum 106 (also called "stratum basale").

The apparatus of the various embodiments may be placed in direct contact with the skin 100 and held in position by pressure or an adhesive. A precisely determined and controlled series of electrical pulses may be applied to one or more disruptor units disposed in or on the apparatus in order to produce localized heat and electrical fields that disrupt the cells of the stratum corneum layer 102 of the skin 100 without damaging the skin cells. The application of the precision controlled heat alters the permeability characteristic of the stratum corneum and produces capillary-like channels in the skin which allow interstitial fluid to flow out of the subject's body. The interstitial fluid may be collected and directed across the surface of the apparatus. On the surface of the apparatus, the interstitial fluid may come into contact with a sensor to determine composition or presence of a certain analyte(s). One such sensor may utilize a biologically reactive element, such as an enzyme. One or more pairs of electrochemical electrodes may be positioned in a manner to measure one or more biochemical analyte or physic-chemical properties of the interstitial fluid sample after the interstitial fluid reacts with the biologically reactive element. For sake of discussion, the dramatic increase in the permeability of the stratum corneum due to the localized application of heat may be referred to as a disruption process. The element which produces the localized heat may be referred to as a disruptor 202. During the disruption process the skin cells remain intact.

Figure 2:
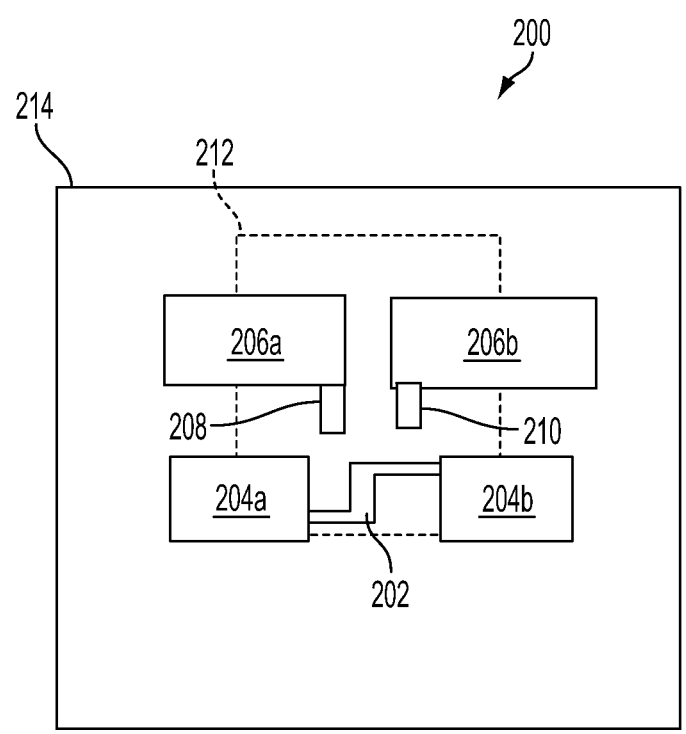
FIG. 2 illustrates a top view of an embodiment transdermal sampling and analysis device.

FIG. 2 illustrates the functional components of a transdermal sampling and analysis device 200 according to an embodiment. A transdermal sampling and analysis device 200 may include a disruptor 202 connected to the positive and negative electrical poles 204a, 204b of a signal generator. In an embodiment, the disruptor 202 may function as a resistive element. After a brief period of increased permeability due to the application of localized heat, the cells return to their normal function. In an embodiment, a disruptor 202 produces heat as electrical current is passed through it. When placed on the skin, the localized heat generated by the disruptor element may cause disruption to the skin cells facilitating the flow of interstitial fluid onto the surface of the transdermal sampling and analysis device 200. The disruptor 202 may be made from a variety of materials which exhibit the appropriate heating and control properties to provide the precise heating control properties required to disrupt the skin cells without damaging them. In addition, the materials used to create the disruptor 202 may be selected for relative ease of manufacture as well as cost considerations. Materials such as titanium, tungsten, stainless steel, platinum and gold may be preferably used to form the disruptor 202. In a preferred embodiment, gold may be used to form the disruptor 202.

A transdermal sampling and analysis device 200 may further include a sensing element comprised of counter electrode 208 and working (or sensing) electrode 210. The electrodes 208, 210 may be coated with a biologically reactive element and coupled to electrically conductive paths 206a, 206b. In an embodiment, the counter and working electrodes 208, 210 form anode and cathode of an electrolytic cell. The counter electrode 208 may be coated with a biologically reactive element to facilitate the conversion of signals generated by a chemical reaction between the biological sample and the biologically reactive element to electrical signals.

Many different analysis techniques may be incorporated into the transdermal sampling and analysis unit to determine the levels and concentrations of various analytes in a biological sample. For example, amperometric, coulometric, potentiometric techniques may be each alternative techniques which may be incorporated into the transdermal sampling and analysis device to determine levels or concentrations of analytes in a biological sample. In addition, electrochemical impedance analysis techniques may be incorporated to detect the presence of particular antibodies in a biological sample.

As an illustration, amperometric techniques may be employed to detect the level or concentration of glucose in a fluid sample. Two electrodes may be separated and insulated from each other and have a voltage potential applied across the electrodes. Because the electrodes are physically decoupled, no current flows from one electrode to the other. The electrodes may be treated with a reactive agent, which in the presence of a particular analyte produces ions through a chemical reaction. The produced ions facilitate the flow of electrical current between the electrodes as the biological sample containing the analyte may be allowed to flow over the surface of the both electrodes. The relative number of ions produced in the reaction may determine the relative ease in which electrical current may flow. In other words, as a higher concentration of the detected analyte is present in the biological sample, the relative current flowing between the electrodes will increase. Thus, the relative concentration of a particular analyte may be calculated based upon the magnitude of current or voltage drop detected between the two electrodes.

Similarly, coulometric methods use analytical chemistry techniques to determine the amount of matter transformed during an electrolysis reaction by measuring the amount of electricity (in coulombs) conducted or produced. Transdermal sampling and analysis devices incorporating potentiometic methods measure potential under the conditions of no or low current flow. The measured voltage potential may then be used to determine the analytical quantity of the analyte of interest. Transdermal sampling and analysis devices incorporating electrochemical impedance method measure the dielectric properties of a medium as a function of frequency.

In an exemplary embodiment, when analyzing concentrations of glucose in a biological sample, enzymatic conversion of glucose to gluconolactone may yield electrons which may be captured to generate anodic current between the counter and sensing electrodes 208, 210, also referred to as counter electrode 208 and working electrode 210. Electrical impedance sensing electrodes, such as electrodes 208, 210, may be configured to determine an electrical impedance spectroscopy across the sensing electrodes 208, 210. The magnitude of the electrical current generated as a result of the chemical reaction may be proportional to the amount or concentration of glucose contained in the obtained biological sample. In an embodiment, a voltage potential may be applied to the counter and working electrodes 208, 210 using a power generator (not shown). Once the biological sample reacts with the reactive biological element coating the electrodes 208, 210, the ions that may be released from the conversion of glucose to gluconolactone facilitate generation of a current across the working and counter electrodes. In such a scenario, the working electrode may function as an anode and the counter electrode may function as a cathode or vice versa. The level of the current may depend on the amount of glucose that is in the biological sample and is converted to gluconolactone. The current that may be generated may be measured by an ammeter, the measurement of which may directly correlate to the level of glucose in the collected biological sample.

The counter and working electrodes 208, 210 may be made from any of a variety of materials which exhibit satisfactory conductivity characteristics and appropriate to the specific measurement used. In addition, the materials used to create the electrodes may be selected for relative ease of manufacture as well as cost considerations. Examples of materials exhibiting satisfactory conductivity characteristics for use as the counter and working electrodes 208, 210 may include platinum, silver, gold, carbon or other materials.

A transdermal sampling and analysis device 200 may further include a reservoir 212 for collecting and containing biological samples such as interstitial fluids that flow from capillary-like channels in disrupted stratum corneum. As interstitial fluid may be released and begins to flow over the transdermal sampling and analysis device 200, the reservoir 212 provides a volume for the interstitial fluid to collect within. By collecting within the reservoir 212, the interstitial fluid may be contained while the analysis of the sample by the electrodes proceeds. The reservoir 212 may be formed under the disruptor 202 and electrodes 208, 210. When the transdermal sampling and analysis device 200 is place on the subject's skin with the disruptor 202 contacting the skin, the reservoir may effectively be positioned above the disruptor 202 and electrodes 208, 210 to contain the released fluid sample. The reservoir 212 may include a cover or lid to more effectively contain the fluid. A cover or lid is discussed in more detail below with respect to FIGS. 14A and 14B. A reservoir 212 may be created using conventional methods known in the art. For example, a reservoir 212 may be created by the buildup of material such as ceramic or polymer on the first side of a supporting base (e.g., substrate 214) in the non-reservoir area either by additive process or by a subtractive process such as photolithography. Alternatively, a spacer material, discussed in more detail below, may be disposed between the lid and substrate 214 to create a cavity for fluid to collect.

A substrate 214 may form the support on which other transdermal sampling and analysis device 200 components may be positioned or attached. The substrate may be formed of a flexible material such that the substrate and components built thereon may deform to conform to the contours of the user's skin. Alternatively, the substrate may be formed of a rigid material such that the user's skin may be forced to deform to conform to the shape of the substrate. The substrate 214 may include a first or top side and a second or back side. The transdermal sampling and analysis components may be attached to the first side of the substrate 214. The substrate 214 may include certain characteristics to accommodate all the functions of the transdermal sampling and analysis devices 200 of the various embodiments. For example, a substrate 214 may have to withstand various etching and or photo-lithography processes which deposit materials to form the disruptor 202 and electrodes 208, 210 without being damaged. In addition, the first side of the substrate 214 may undergo an etching process to create the reservoir 212. In addition, it may be desirable for the substrate 214 to exhibit certain thermal conductivity properties. For example, it may be desirable for the heat generated by the disruptor unit 202 to remain localized and concentrated. Accordingly it may be desirable for the substrate to have a high thermal resistivity such that heat generated by the disruptor is not conducted by the substrate 214 to areas other than those directly in contact with the disruptor unit 202. Additionally, it may be desirable for the substrate to possess a resistance to thermal expansion.

Different substrates 214 may be used as a base in a transdermal sampling and analysis device 200. Substrates 214 with high coefficient of thermal expansion may flex or buckle as voltage (or current) is applied to the disruptor 202 and heat is generated. The flexing or buckling action may displace the disruptor unit 202 away from the surface of the skin 100, resulting in an insufficient heating of the stratum corneum. Consequently, the permeability of the stratum corneum may not be altered sufficiently to allow for the flow of interstitial fluid. The end result being that the volume of the obtained biological sample is not sufficient to adequately analyze. The disruptor 202 may be required to continuously contact the skin 100 to create the capillary-like channels in the stratum corneum which may allow interstitial fluid to flow from the body of the subject onto the transdermal sampling and analysis device 200. Thus, a low thermal modulus substrate 214 may be selected that does not displace the disruptor 202 from the skin 100.

Further, repeated heating and cooling of the substrate 214 may damage components of the transdermal sampling and analysis device 200 that may be attached to the substrate 214. For example, differences in thermal expansion characteristics between the materials used for the disruptor 202 and the substrate 214 may result in separation of the disruptor 202 from the substrate 214. In other words, the disruptor may begin to peel away from the substrate after repeated heating and cooling cycles. Accordingly, in a preferred embodiment the substrate may exhibit high thermal resistivity (low thermal conductivity) properties while mirroring the low thermal expansion characteristics of the disruptor 202 material. Different substrates 214 may have different thermal expansion properties. For example, most metals substrates 214 have coefficient of thermal expansion of about 5~10 ppm/° C.; glass has a coefficient of thermal expansion of ~8 ppm/deg F.; common plastics have coefficient of thermal expansion of 20~30 ppm/° C.

However, in some alternative embodiments, the thermal expansion characteristics of the materials used in both the substrate 214 may be manipulated to advantageously result in a mechanical movement of the substrate. This mechanical movement of the substrate 214 may cause a break, disruption, or dislocation of bonds in the lipid barrier membrane, further enabling or assisting in the displacement of biological fluid out from the interstitial region, over and through the transdermal sampling an analysis device 200. For example, as electrical current is applied through the disruptor 202 heat may be generated. The heating of the disruptor 202 causes the substrate 214 housing the disruptor 202 to also heat. This heating results in an expansion of the substrate 214 material in accordance with coefficient of thermal expansion. As the current applied to the disruptor 202 is disengaged, both the disruptor 202 and the surrounding substrate 214 will cool. This cooling results in a contraction of the substrate 214 material. As discussed in more detail below, current to the disruptor 202 may be pulsed. The pulsing on and off of the applied current may cause in a rhythmic expansion and contraction cycle of the substrate 214 to result in a mechanical movement of the substrate, perpendicular to its plane to enhance flow of biological fluid out of the interstitial region. Materials having a sufficient coefficient of thermal expansion may result in a translation of the substrate 214, perpendicular to its plane, of between 0.05 μm and 3.0 μm. In a preferred embodiment, materials having a coefficient of thermal expansion are selected to result in a translation of the substrate 214, perpendicular to its plane, of between 0.1 μm and 0.6 μm.

In an embodiment, the substrates 214 may include physical and/or chemical properties to accommodate certain temperatures without being damaged or cause damage to the components of the transdermal sampling and analysis device 200. In an embodiment, a disruptor 202 generating temperatures as high as 200° C. may be attached to the substrate 214. Thus, the substrate 214 may have to withstand such high temperatures without melting, permanently deforming or conducting the heat to other components of the transdermal sampling and analysis device 200.

Even if a substrate 214 does not melt or permanently deform under high temperatures, the substrate 214 may expand or contract due to varying temperatures. Because components of the transdermal sampling and analysis device 200 may be fixedly attached to the substrate 214, expansion and contraction of the substrate 214 may cause the attached components to detach and cause damage to the configuration of the transdermal sampling and analysis device 200.

To reduce or eliminate the size variation of the substrate 214 under varying temperatures, different substrates 214 may be considered. In an embodiment, a substrate 214 made of a material with a coefficient of thermal expansion of about 10 to 20 ppm/deg F. may be used to reduce the expansion/contraction effects of the substrate 214 when exposed to high heats of about 100° C. to 200° C. In a further embodiment, a substrate 214 made of a material with a coefficient of thermal expansion of about 10 to 12 ppm/deg F. may be used. In a further embodiment, a substrate 214 may have a coefficient of thermal expansion that may be within a 20% deviation from the CTE of the disruptor 202 material.

To reduce or eliminate conduction of heat from the disruptor 202 attached to the substrate 214 to other components of the transdermal sampling and analysis device 200, alternative materials may be considered for the substrate 214. In an embodiment, the substrate 214 may be formed from a material having a coefficient of thermal conductivity of about 0.1 to 1.1 W/m*K to reduce the conduction of heat from the disruptor 202 to other components of the transdermal sampling and analysis device 200 or to other unintended areas of the skin of the subject beyond the portion directly in contact with the disruptor 202. In a further embodiment, the substrate 214 may be made from a material having a coefficient of thermal conductivity of about 0.1 to 0.2 W/m*K. In a further embodiment, a substrate 214 may be made from a material having a coefficient of thermal conductivity of about 0.13 W/m*K or lower.

In an embodiment, selection of a substrate 214 for the transdermal sampling and analysis device 200 may depend on the coefficient of thermal expansion and conductivity of the material used to make the disruptor 202 of the transdermal sampling and analysis device 200. For example, the substrate 214 may be made of a material which has a coefficient of thermal expansion that deviates from the CTE of the material used in the disruptor 202 by less than 50%, and preferably by less than 20%. In a further embodiment, the substrate 214 may be made of a material which has a coefficient of thermal conductivity (CTC) that is lower than 0.5 W/(m·K)

In an embodiment, the substrate 214 suitable for use in the transdermal sampling and analysis device 200 of the various embodiments may be made of a variety of materials such as glass, plastic, metal or silicon.

In an embodiment, the substrate 214 may be made of plastic. When heat is applied to plastics, the plastic material typically shrinks in size before expanding in size. Because of this unique characteristic of plastic, application of heat to a substrate 214 made of plastic may cause damage to the components of the transdermal sampling and analysis device 200 attached to the plastic substrate 214. To prevent the initial contractions, the plastic material used to make the substrate 214 may be annealed plastics (i.e., plastics which have been previously heated to remove or prevent the internal stress caused by the initial shrinkage). Annealed plastics are known in the art and may be produced by annealing a plastic material to cause a change in its properties.

In a further exemplary embodiment, the substrate 214 may be made of a polyimide such as Kapton™. Kapton™ is a polyimide film developed by DuPont™ which can remain stable in a wide range of temperatures, from −273 to +400° C. (0-673 K).

A biologically reactive element, such as an enzyme, may be applied to the first side of the substrate. For example, the biologically reactive element may be applied to the working electrode 210, the counter electrode 208 or both. As the stratum corneum is disrupted and interstitial fluid begins to flow through the stratum corneum into the reservoir 212 by capillary action of the structure. The interstitial fluid may be directed to flow into the reservoir 212 and specifically over the surface of the counter and working electrodes 208, 210. The obtained fluid may come into contact with the biologically reactive element on the surface of the counter and working electrodes 208, 210 causing a chemical reaction that releases energy in the form of electrons. The counter and working electrodes 208, 210 may form anode and cathode of an electrolytic cell, enabling current flow through a device which can measure the current at a controllable potential. Thus, the electrons (ions) released from the chemical reaction between the biological sample and biologically reactive element may be converted into electrical signals. The electrical signals generated by the chemical reaction may be measured to determine the amount of a target analyte in the obtained biological sample.

Excessive thickness of the biologically reactive elements on the first side of the substrate may cause certain problems during the manufacturing process or during the operation of the device. For example, greater thickness of the biologically active layer requires greater depth of channels to allow space for the biological sample to flow over the electrodes. If the applied biologically reactive element layer is too thick, greater than 10 micrometers for example, such as common in commercial glucose transdermal sampling and analysis devices, it may clog or fill the channels 222 that may be configured to guide the biological sample over the electrodes rendering the transdermal sampling and analysis device 200 dysfunctional, or causing the need for increased channel thickness at increased cost. Channels 222 are discussed in more detail below. In an exemplary embodiment, to avoid clogging the channels 222 and blocking the movement of the biological sample over the electrodes, the biologically reactive element may be applied in such a way as to result in a thickness of less than 5 micrometers, and preferably less than 1 micrometer. This can be accomplished by the use of a system such as described by Eugenii Katz, biochemistry and bioenergetics 42 (1997) 95-104 or other known method of thin sensor layer deposition. By reducing the thickness of the biologically reactive element, potential clogs to the channels 222 in the transdermal sampling and analysis device 200 may be prevented without the additional cost of increased channel depth.

One example of a commonly used biologically reactive element may be the enzyme Glucose Oxidase (GOD). Another example of a commonly used biologically reactive element may be the enzyme glucose dehydrogenase. In an exemplary embodiment, GOD may be applied to cover the surface of the working electrode 210. To determine a subject's glucose levels, a transdermal sampling and analysis device 200 with a disruptor 202 may be applied in direct contact with the skin cells. By applying a voltage (or current) across the terminals of the disruptor 202, a precision controlled heat may be produced and localized to the disruptor 202 site. The localized heat may be applied against the skin to alter the permeability of the skin cells and consequently creates capillary-like channels. Interstitial fluid may flow out of the capillary-like channels into the reservoir 212 and over the counter and working electrodes 208, 210. The glucose molecules in the interstitial fluid may react with GOD covering the surfaces of the working electrode 210. Glucose oxidase catalyzes a breakdown of glucose in the interstitial fluid to gluconolactone, releasing electrons to a mediator such as $K_3Fe[CN]_6$. The electron mediator (or electron shuttle) may transfer electrons to the working electrode 210, where anodic potential has been applied such that the mediator may be oxidized. The oxidized mediator may be then able to accept another electron from the glucose conversion reaction to repeat the process. The electrons released in this oxidation reaction may travel through the working electrode 210 towards the counter electrode, 208 generating a current. The magnitude of the sensed electrical current generated by this reaction may be proportionally related to the concentration levels of glucose in the interstitial fluid. Thus, by determining the magnitude of current generated across the working and counter electrode, one may determine the relative amount of glucose in the obtained sample.

Figure 3:
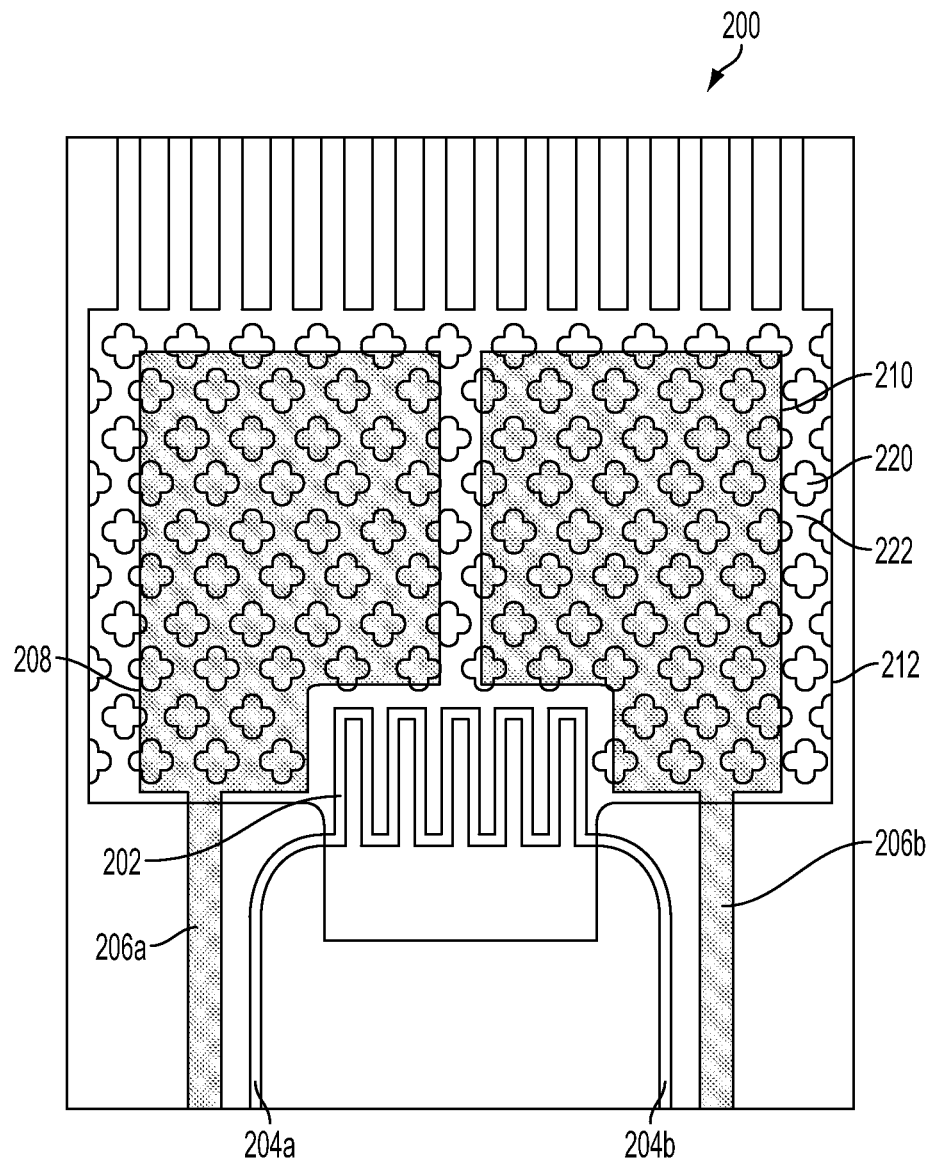
FIG. 3 illustrates a top view of an embodiment transdermal sampling and analysis device with a square reservoir.

FIG. 3 illustrates a top view of a transdermal sampling and analysis device 200 showing an embodiment orientation and configuration of the functional components of the transdermal sampling and analysis device 200. The transdermal sampling and analysis device 200 may include a disruptor 202 connected to two electrically conductive paths 204a, 204b. The conductive paths 204a, 204b may be coupled to the positive and negative nodes of a power source (not shown). The disruptor 202 may be placed adjacent to a working electrode 210 and counter electrode 208. The counter and working electrodes 208, 210 may be connected to electrical conductive paths 206a, 206b, respectively.

The surface of the counter and working electrodes 208, 210 may be patterned with support structures 220 which displace the electrodes 208, 210 from the surrounding skin of the subject. As the transdermal sampling and analysis device 200 may be pressed against the subject skin, it may be necessary to displace the electrodes 208, 210 from the surrounding skin in order to allow the free flow of obtained interstitial fluid over the surface of the electrodes 208, 210. The surrounding skin 100 may deform across the surface of the electrodes 208, 210, effectively preventing the biological sample from coming into contact with the electrode surfaces. By placing support structures 220 over the electrodes, the surrounding skin may be effectively lifted off the surface of the electrode. The various patterns of support structure 220 may also create channels 222 which direct the biological samples over the entire surface working and counter electrodes 208, 210 due to capillary action. These patterns may be of any shape or arrangement. For example, the counter and working electrodes 208, 210 may be configured to include star shaped channel supports 220 to manipulate the movement of biological sample over the entire surface of the counter and working electrodes 208, 210.

Because the amount of biological sample required is minute and the surface area of the counter and working electrodes 208, 210 may be relatively small, a uniform coverage of the counter and working electrodes 208, 210 by the biological sample may enhance the accuracy of the final analysis of analytes. Results obtained from a transdermal sampling and analysis device 200 in which the entire surface of a counter and working electrodes 208, 210 are covered require less time and volume of biological sample for analysis and may be more accurate.

Figure 4:
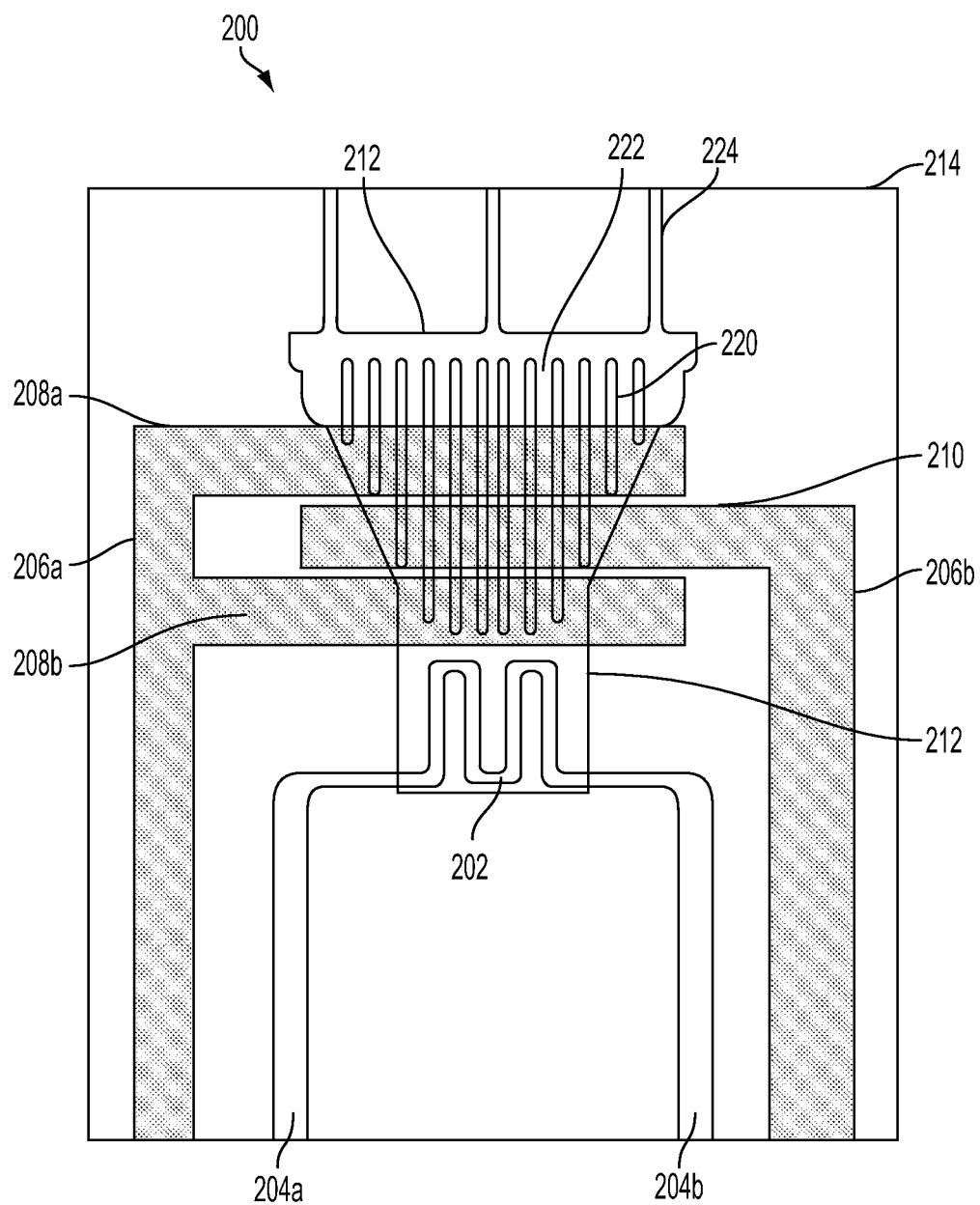
FIG. 4 illustrates a top view of an embodiment transdermal sampling and analysis device with a trapezoidal shaped reservoir.

FIG. 4 illustrates a top view of another embodiment transdermal sampling and analysis device 200. The functional elements of the transdermal sampling and analysis device 200 may be disposed upon the surface of a substrate 214 and may be configured to include counter and working electrodes 208, 210 that may be inter-digitated. In such a configuration, more than one counter and working electrodes 208, 210 may be used to create the inter-digitated configuration. For example, a total of three electrodes may be used to create the inter-digitations; two counter electrodes 208a and 208b as well as one working electrode 210. The counter and working electrodes 208, 210 may be coupled to a current or sensing unit via electrically conductive paths 206a, 206b. Elongated channels 222 may be formed using long channel supports 220. The channels 222 may cover the entire surface of the counter and working electrodes 208a, 208b, 210. A disruptor 202 configured in a serpentine shape may be positioned adjacent to the counter and working electrodes 208a, 208b, 210. A reservoir 212 may be created to surround the disruptor 202 and the counter and working electrodes 208a, 208b, 210. The disruptor 202 may be connected to the positive and negative electrical poles 204a, 204b of a signal generator.

A biological sample, such as interstitial fluid, may flow from capillary-like channels created by the disruptor 202 into the reservoir 212 through capillary action. As the biological sample flows into the reservoir 212, the channels 222 and channel supports 220 may assist the movement and direction of the biological samples in the reservoir 212 to disperse the biological sample over the entire surface of the counter and working electrodes 208a, 208b, 210 through further capillary action caused by the relative hydrophilic properties of the selected channel support 220 material, as described in more detail below.

Exhaust ports or vents 224 may be present on the side of the reservoir 212 towards which the biological sample may move. The exhaust ports/vents 224 may relieve any air pressure that would otherwise be caused by air trapped within the reservoir 212 and prevent the biological sample from moving towards the far side of the reservoir 212. In the embodiment shown in FIG. 4, the reservoir 212 may be in a shape of a trapezoid to allow biological samples to flow from the disruptor 202 over the working and counter electrodes 208, 210 using the channels 222 and the channel supports 220. In alternative embodiments, the exhaust vent 224 may be configured to direct the vented gases back toward the disruptor 202 so that the gases may be recirculated back through a hole in a lid 1302 (see FIG. 14B and discussion below regarding lid). Embodiments utilizing exhaust ports 224 may be referred to as vented embodiments, whereas embodiments that do not utilize exhaust ports may be referred to as unvented or non-vented embodiments.

FIGS. 5A-5D illustrate top views of various embodiment transdermal sampling and analysis devices 421-424 each having a different configuration of the functional components. The embodiments shown in each of FIGS. 5A-5D possess different disruptor 202(5A)-202(5D) configurations, but assume for purposes of this discussion that disruptors 202(5A)-202(5D) may be formed of the same material. Moreover, for purposes of this discussion it may be assumed that the same voltage (or current) may be applied across each of disruptors 202(5A)-202(5D).

Figure 5A:
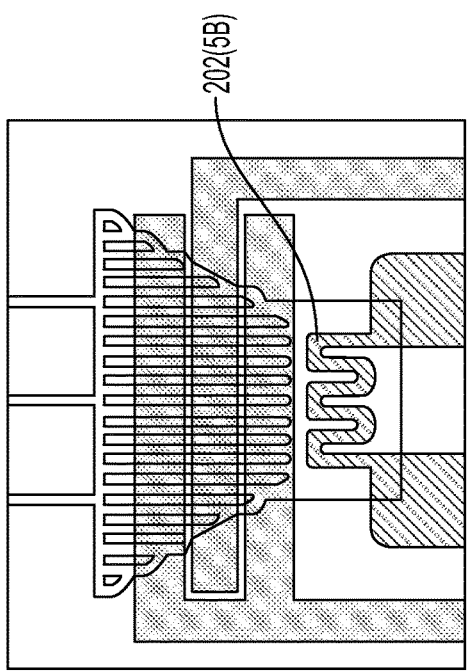
FIGS. 5A-5D illustrate top views of embodiment transdermal sampling and analysis devices having different disruptor and reservoir configurations.

Similar to the transdermal sampling and analysis device shown in FIG. 4, FIG. 5A illustrates a transdermal sampling and analysis device 421 including interdigitated counter and working electrodes 208a, 208b, 210 and a disruptor 202(5A) with a serpentine configuration. In the embodiment shown in FIG. 5A the cross section of disruptor 202(5A) has a relatively small wire gauge (i.e., larger cross section diameter). The smaller gauge may result in a disruptor 202(5A) having a relative lower resistive value and thus a lower localized heat as compared to a disruptor 202 having a higher resistive value where the same voltage may be applied.

Figure 5B:
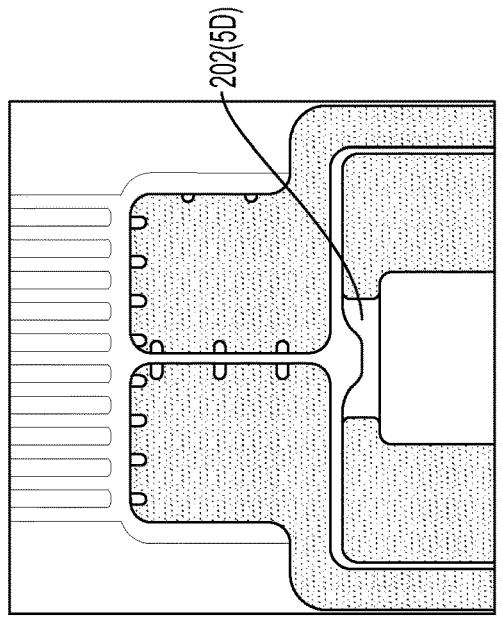

FIG. 5B illustrates a top view of another embodiment transdermal sampling and analysis device 422. The functional components of the embodiment shown in FIG. 5B are similar to those shown in FIG. 5A. In particular, the total length of the disruptor 202(5B) shown in FIG. 5B may be the same disruptor 202(5A) shown in FIG. 5A. In addition, the total area covered by the disruptor 202(5B) shown in FIG. 5B may be the same as disruptor 202(5A) shown in FIG. 5A. However, the gauge of the serpentine coils of disruptor 202(5B) shown in FIG. 5B may be shown to be larger (i.e., smaller cross sectional dimension) than the disruptor 202 (5A) shown in FIG. 5A. Consequently, when the same voltage (or current) applied to the disruptor 202(5A) in FIG. 5A may be applied to the disruptor 202(5B) in FIG. 5B, a higher temperature localized heat may be generated due to the increased resistive value. Since the higher temperature produced by the disruptor 202(5B) shown in FIG. 5B may be distributed over the same relative area as that produced by the disruptor 202(5A) shown in FIG. 5A, the power density of the disruptor 202(5B) shown in the embodiment of FIG. 5B may be much higher relative to the disruptor 202(5A) shown in FIG. 5A.

Figure 5C:
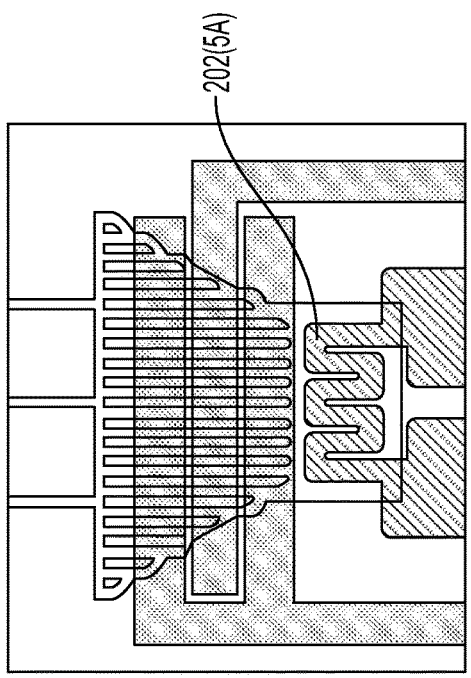

FIG. 5C illustrates a top view of another embodiment transdermal sampling and analysis device 423. In contrast to disruptor 202(5A) shown in FIG. 5A, disruptor 202(5C) shown in FIG. 5C has a larger gauge than disruptor 202(5A), but has fewer windings and covers a smaller total area than disruptors 202(5A) and/or 202(5B). As compared to disruptor 202(5A), because disruptor 202(5C) has a smaller gauge than disruptor 202(5A), disruptor 202(5C) will typically have a higher resistive value than disruptor 202(5A). However, because disruptor 202(5C) also has fewer windings than disruptor 202(5A), the total length of disruptor 202(5C) may be shorter than disruptor 202(5A). As a result, the increase in resistive value of disruptor 202(5C) over disruptor 202(5A) due to the larger gauge may be effectively negated and the resistive value of disruptor 202(5C) may be the same as disruptor 202(5A). However, because disruptor 202(5C) covers a significantly smaller total area as compared to disruptor 202(5A), the power density of disruptor 202(5C) may be significantly greater relative to that of disruptor 202(5A). As compared to disruptor 202(5B), disruptor 202(5C) has the same gauge value as disruptor 202(5B) but has fewer windings. As a result, the total length of disruptor 202(5C) may be less than disruptor 202(5B). Consequently, disruptor 202(5C) will have a lower resistive value relative to that of disruptor 202(5B). However, since disruptor 202(5C) covers a significantly smaller total area as compared to disruptor 202(5B), the power density of disruptor 202(5C) may effectively be the same relative to that of disruptor 202(5B).

Figure 5D:
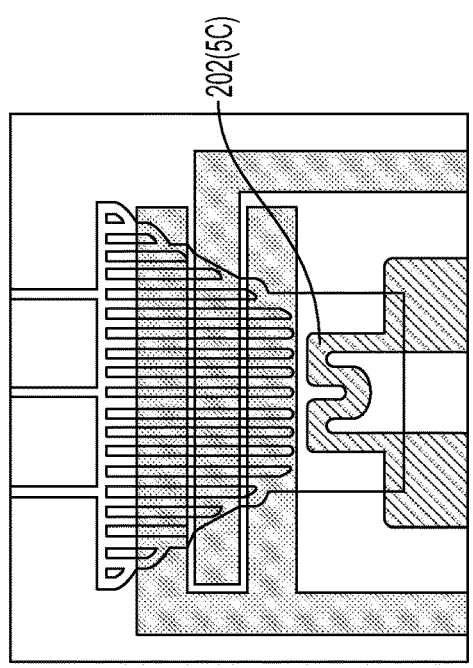

FIG. 5D illustrates an embodiment transdermal sampling and analysis device 424 including counter and working electrodes 208, 210 with large smooth surfaces. In contrast to the configurations shown in FIGS. 5A-5C, the reservoir 212 and the disruptor 202(5D) may be rectangular in shape as opposed to serpentine. In addition, the electrodes 208, 210 may be shown as rectangular electrodes that are not interdigitated. The relative resistive value of disruptor 202(5D) may be much lower than that of disruptors 202(5A)-202(5C) as its gauge may be nearly that of disruptor 202(5A) but total length may be nearly that of 202(5C). In addition, because disruptor 202(5D) covers approximately the same total area as disruptor 202(5C), the power density of disruptor 202 (5D) may be less relative to that of disruptor 202(5A), disruptor 202(5B) and disruptor 202(5C). The various embodiments may be designed to deliver heat to the subject's skin with a power density of 1-10 W per $mm^2$. In a preferred embodiment the disruptor delivers heat to the subject's skin with a power density of 2-5 W per $mm^2$.

As shown in FIGS. 5A-5D, the transdermal sampling and analysis devices 421-424 of the various embodiments may be made using a variety of different disruptor 202(5A)-202 (5D) configurations. As discussed above, the size and shape of the disruptor may affect its resistive characteristics and consequently, its ability to generate a localized heat. In addition, the material selected to form the disruptor may also affect its resistive characteristics and consequently, its ability to generate a localized heat. As with electrode material selection, disruptor materials may be selected from a wide variety of materials exhibiting satisfactory electrical conductance/resistive properties such that sufficient heat may be generated when specific voltages are applied to the disruptor leads. In addition, thermal conduction and resistance characteristics should be observed in an optimal disruptor material. Finally, ease of manufacturing processing and cost may determine the final selection of disruptor material. For example, a disruptor 202 may be made of nichrome, titanium, tungsten, or gold. In a preferred embodiment, the disruptor 202 may be made from gold.

As discussed above with reference to FIGS. 5A-5D, the disruptor 202 may be formed in a variety of configurations. FIGS. 6A-6E illustrate additional shapes that the disruptor 202 may be formed. For example, a disruptor 202 may be formed in serpentine, circular, crescent, semi-circular, linear, square, rectangular, trapezoidal, hexagonal and triangular shapes. Each unique shape may impact the manner in which the generated heat may be localized. Studies have shown that that the resulting sensation experienced by the subject induced by the varying disruptor shape also varies. By varying the shape of the disruptor 202, the sensation or discomfort experienced by the subject may be increased or decreased.

Figure 6A:
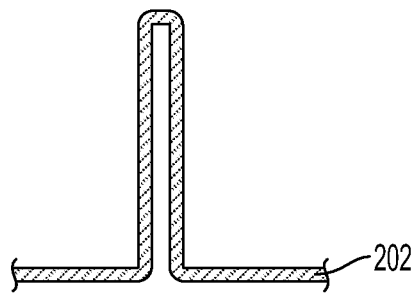
FIGS. 6A-6D illustrate top views of embodiment disruptors having different configurations.
Figure 6B:
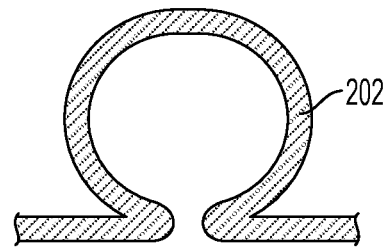
Figure 6C:
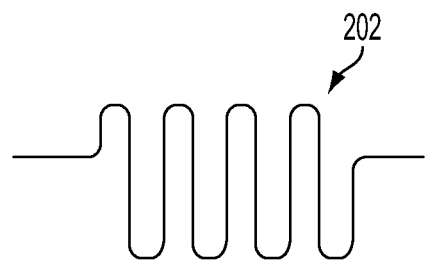
Figure 6D:
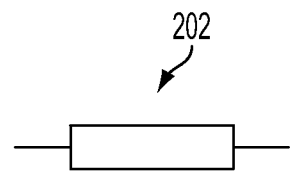

FIG. 6A illustrates a top view of an embodiment disruptor 202 with a linear shape. FIG. 6B illustrates a top view of an embodiment disruptor 202 formed in the shape of the Greek letter omega. FIG. 6C illustrates a top view of an embodiment disruptor 202 formed in a serpentine shape. FIG. 6D illustrates a top view of an embodiment disruptor 202 formed in a rectangular shape. Disruptor shape configuration may affect the relative sensation or discomfort experienced by the subject from which the biological sample may be drawn. In a preferred embodiment, the disruptor unit may be formed such that the perimeter of the disruptor preferably forms a rectangle. Such preferred disruptor units may be formed from solid disruptors 202 such as that shown in FIG. 6D or in alternative serpentine configurations such as shown in FIG. 6C. The serpentine configuration has some advantages. For example, because the serpentine disruptor may be formed by a long, thin coil (as compared to a solid rectangle), the resistive characteristic of the disruptor may be much larger (assuming similar or same material). In addition, the thinner cross section of each coil also contributes to a higher overall resistive value of the disruptor unit. In this manner, the serpentine shaped disruptor may occupy a generally rectangular area, while providing sufficiently high resistance to produce the required localized heating levels to obtain a transdermal biological sample with minimal sensation and discomfort to the subject.

In an embodiment, the area determined by the perimeter surrounding a disruptor 202 may affect the amount of biological sample that may be collected or the amount of sensation or sensation that may be experienced by the subject. In addition to absolute area, the aspect ratio of the disruptor 202 may impact sensation versus fluid generation level. Aspect ratio is a ratio of the area of the skin 100 that a disruptor 202 may cover as compared to the parameters of the disruptor 202, such as the disruptor's length and cross-sectional area. Different aspect ratios may affect the process of disruption of the skin cells and levels of sensation differently. For example, if the skin area that the disruptor 202 may cover is of excessive aspect ratio (e.g., a long and thin disruptor such as shown in FIG. 6A), the use of the disruptor 202 may cause high levels of sensation without obtaining a sufficient amount of biological sample. A preferred aspect ratio has been found to be about 2:1. A more preferred aspect ratio may be 1:1 (i.e., a square or circular) +/−50%. At such preferred aspect ratios, subjects have exhibited the least sensation or discomfort while obtaining a sufficient amount of biological sample.

Figure 7:
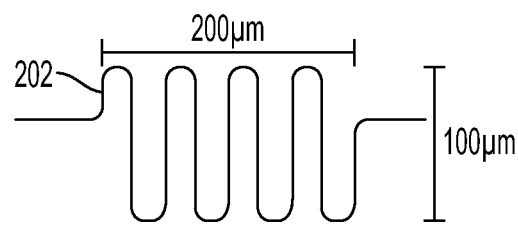
FIG. 7 illustrates the measurement of an aspect ratio of a serpentine disruptor.

In an embodiment, where the aspect ratio may be about 2:1, the disruptor 202 may cover a rectangular area with a length of about 150 μm-400 μm and width of 50 μm-200 μm. In a further embodiment, the disruptor 202 may have a length of about 200 μm-400 μm and a width of 100 μm-200 μm. FIG. 7 illustrates an exemplary serpentine disruptor 202 with a length of 200 μm and a width of 100 μm. In a preferred embodiment, the dimensions of the disruptor 202 may include a length of 120 μm and width of 60 μm. By minimizing the size of the disruptor unit, the relative sensation and discomfort may be likewise minimized. However, limits on manufacturing processes as well as the need to disrupt a large enough area of stratum corneum to obtain a sufficiently large enough sample of biological material may dictate the minimal effective size of the disruptor unit. The disruptor 202 with dimensions of 120 μm×60 μm may obtain a sufficient amount of biological sample while causing a negligible sensation or discomfort to the subject.

In a further embodiment, other aspect ratios less than 2:1 may also be used. For example, a disruptor 202 may have a length of 100 μm and a width of 60 μm. In a further embodiment, where the aspect ratio may be about 1:1, the disruptor 202 may cover a square area with a length and width of about 50 μm-400 μm. In a further embodiment, the disruptor 202 may have a length and width of about 100 μm-400 μm. In an exemplary embodiment, a serpentine disruptor 202 with a length and width of 200 μm may be used. In a preferred embodiment, the dimensions of the disruptor 202 may have a length and width of about 120 μm. In a preferred embodiment, the disruptor 202 may have the dimensions of 200 μm×200 μm. In a more preferred embodiment a disruptor 202 may have the dimensions of 60 μm×60 μm.

Electrical resistance of a disruptor may be calculated using the following equation:

$$R=\rho L/A$$

where,

R is the electrical resistance of a uniform specimen of the material (measured in ohms, Ω)

$\rho$ is electrical resistivity of the material (measured in ohm-meters, Ω-m)

L is the length of the piece of material (measured in meters, m); and

A is the cross-sectional area of the specimen (measured in square meters, $m^2$).

By varying the value of each of these parameters, different electrical resistances may be achieved. For example, the thinner the cross-section of the specimen used in the disruptor, the greater the electrical resistance of the disruptor. Similarly, the longer the length of the material used in the disruptor 202, the greater the electrical resistance of the disruptor. Conversely, a wider cross section or shorter disruptor may result in a lower electrical resistance of the disruptor.

The higher the electrical resistance, the greater the heat generated given a constant current applied through the disruptor 202. Thus, to obtain a desired heat level, the material used in the disruptor 202 should achieve a desired electrical resistance. Because electrical resistivity of a material may be constant, the length and cross-sectional area of the material may be adjusted to achieve a desired electrical resistance which in turn may generate a desired heat level. For example, to achieve high electrical resistance in a disruptor 202 which employs a short piece of gold material, the cross-section area of the gold material may be reduced. Likewise, to achieve high electrical resistance in disruptor 202 which uses a gold material with a large cross-section area, the length of the gold material may be increased.

Figure 8:
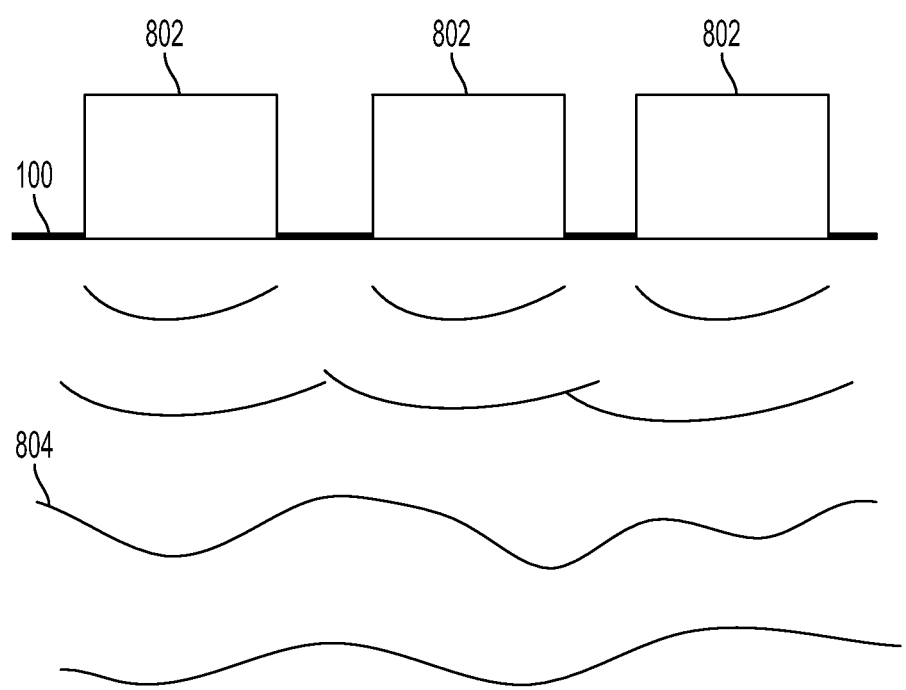
FIG. 8 illustrates a cross-sectional view of an embodiment disruptor having a serpentine configuration placed on the skin.

While the serpentine configuration of the disruptor creates multiple sites for heat production on the skin, the constructive interference of the heating generated effectively applies a singular source of heating to the subject skin. FIG. 8 illustrates a cross-sectional view of an embodiment serpentine disruptor 202 positioned next to the skin 100. For example, each coil 802 may generate heat resulting from the resistance to electrical current applied to the leads of the disruptor 202. The generated heat may be conducted through the layers of the skin. The discrete heating from each coil 802 may constructively interfere with the heating generated from other neighboring coils 802 to create a uniform heat gradient 804. A uniform, continuous heating gradient 804 may cause uniform and effective disruption to the skin cells. In this manner, the serpentine configuration of the disruptor provides the same uniform heating as can be achieved through use of a solid rectangular configuration for the disruptor. Moreover, the serpentine configuration may provide a disruptor with greater electrical resistance as compared to a solid rectangular disruptor confined to the same area.

In a serpentine disruptor 202, the distances of the coils 802 from one another may determine whether uniform heating gradient 804 may form as discrete heat sources as they travel through the stratum corneum. If the distances between the coils 802 are too large, a uniform and continuous heating gradient 804 may not form at all or may form at a skin level below the stratum corneum, thus, failing to effectively and uniformly disrupt the cells of the stratum corneum. In an embodiment, the coils 802 of the serpentine disruptor 202 may be about 5 μm to 40 μm apart. In a preferred embodiment, the coils 802—of the serpentine disruptor 202 may be about 15 μm apart.

Given the variety of disruptor properties that may be varied (e.g., size, shape, gauge, material, current applied, etc.) a disruptor may be formed and implemented that exhibits the desired electrical characteristics to generate a sufficient fluid sample while imparting negligible sensation and/or discomfort to the patient. For example, assuming no other changes, as the size (area) of the disruptor increases so does the amount of fluid extracted. However, again assuming no other changes, as the size (area) of the disruptor increases so does the amount of sensation and discomfort experienced by the patient. Thus, certain proportional relationships may be known. The amount of sensation or discomfort a patient may experience may be proportionally related to the area of the disruptor, the aspect ratio of the disruptor, and the power density that applied. Likewise, the amount of fluid that can be extracted may be proportionally related to the area of the disruptor and the power density that applied. Tests have indicated that an applied power density of 1 W per $mm^2$ may be the minimum amount of power required to disrupt a patient's stratum corneum.

In practice a disruptor may be constrained by a number of other factors. For example, in a portable application there may be voltage/current constraints resulting from the use of a particular battery, thus, dramatically impacting the power density requirements. Economic or manufacturing constraints may limit the materials from which the disruptor may be manufactured. When faced with any of these constraints, a disruptor may still be designed by varying the combination of disruptor properties so that each of the constraints is met.

As previously discussed, the disruptor 202 may essentially operate as a resistor which, when a voltage (or current) is applied to the leads of the disruptor 202 creates a localized heat source. The amount of heat required to disrupt the skin cells to obtain sufficient amounts of biological samples and cause the least discomfort or sensation may depend on different variables, such as the thickness of the skin 100 and the concentration of nerve endings on the skin 100. Furthermore, sensation and discomfort are subjective to each individual subject. However, the stratum corneum is generally about 50 μm in thickness. It may be thicker or thinner at various locations of the subject. For example, it is thicker at the palm of the hands and soles of the feet and thinner on the eyelids. In an embodiment, the heat generated by the disruptor may result in a heater temperature of about 100° C. to 200° C. The lower temperatures may cause less sensation while higher temperatures may produce larger amounts of biological sample. A desired location for applying the heat to disrupt the skin cells may be on the medial surfaces of the forearm. Given the relative thickness of the stratum corneum at this location as well as the relative number of nerve endings at this location, it may be preferable to apply at 50° C. to 150° C. from the disruptor to cause the disruption in the stratum corneum. In a more preferred embodiment, the temperature of the disruptor may be about 90° C. to 110° C.

In an embodiment, since different subjects may have different skin thickness levels, calibration of the transdermal sampling and analysis device 200 of the various embodiments may be required to generate sufficient heat for obtaining the most amounts of biological samples with the least amount of sensation. Thus, the level and duration of the temperature of the disruptor 202 may be adjusted for different subjects.

In an embodiment, the disruption of the skin 100 may occur when heat of about 85° C. to 140° C. from the disruptor 202 may be applied to the skin surface for durations of about 100 ms to 200 ms. In a further embodiment, the disruption of the skin may occur when heat of 140° C. from the disruptor 202 may be supplied to the skin 100 surface for durations of about 120 ms to 160 ms. In a preferred embodiment, the disruption of the skin 100 may occur when heat of 140° C. from the disruptor 202 may be supplied to the skin 100 surface for duration of about 140 ms.

In order to safely operate on and around the subject, lower voltages and currents may be desirable. Voltages of 10 V or higher may be detected by the body and have been observed in encephalograms. Thus, to reduce the effects of the voltage on the body, it may be preferable to use voltages lower than 10 V. Since there may be a limit on the amount of voltage that may be safely applied to a subject, the electrical resistance of the disruptor 202 may be adjusted based on the desired voltage. Likewise, there may be a limit on the amount of current that may be safely applied to a subject, the electrical resistance of the disruptor 202 may be adjusted based on the desired current. In an embodiment, the voltage supplied to the disruptor 202 may be about 1 V to 10 V. In a preferred embodiment, the voltage supplied to the disruptor 202 whose area is about $2\times10^{-8}$ $m^2$ may be about 2 V. In another embodiment where a current source applies a current, the current supplied to the disruptor 202 may be about 35 mA to 145 mA. In another embodiment where a current source applies a current, the current supplied to the disruptor 202 may be about 20 mA to 120 mA. In a preferred embodiment, the current supplied to the disruptor 202 may be about 100 mA, preferably about 70 mA. For this preferred embodiment, the corresponding power density per unit area of the disruptor on the skin may be about $5\times10^6$ $W/m^2$, the energy per pulse may be about 65 mJ, and the energy per unit area of the disrupter on the skin may be about $3\times10^6$ $J/m^2$. Since the amount of heat generated by a resistive element is dependent upon the resistive value of the resistive element and the amount of voltage (or current) applied across (through) the resistive element, the disruptor 202 suitable for use in the various embodiments may include an electrical resistance of about 1 Ohm to 100 Ohm. In a preferred embodiment, the electrical resistance may be about 5 Ohm to 50 Ohm. In a preferred embodiment, the disruptor may have an electrical resistance of about 15 Ohm. In another embodiment, the disruptor may have an electrical resistance of about 22 Ohm. One of skill in the art would recognize that voltage and current may be proportionally related to one another by Ohm's law. Much of the discussion herein may discuss the application of voltages to the disruptor 202. One of skill in the art would recognize that analogous current source limitations may apply.

To generate the desired heat at the disruptor 202, electrical current may be applied to the conductive paths 204a, 204b having a duty cycle that may vary from 0 to 100 percent. The electrical current applied to a disruptor 202 may be a direct or alternate current. A duty cycle is the fraction of time that the electrical current is being applied to the disruptor 202 and may be static (100%) or pulsed (<100%). It has been found that by pulsing the electrical current effective heating of the stratum corneum may be achieved while mitigating any sensation or discomfort experienced by the subject. In a preferred embodiment, a pulsed direct current may be applied to the disruptor 202. The pulsed direct current may be applied to the conductive paths 204a, 204b of a disruptor 202 using a duty cycle of about 80 percent.

In an exemplary embodiment, current may be applied for a period of 200 ms. If the duty cycle is about 80 percent, the direct current may be turned on to apply electrical current to the disruptor 202 for about 160 ms and turned off for 40 ms during the 200 ms period.

In an embodiment, the frequency of a pulsed duty cycle may be about 1 Hz to about 1 kHz. In a preferred embodiment, the frequency of the pulsed duty cycle may be about 1 Hz to about 10 Hz. In a more preferred embodiment, the frequency of the pulsed duty cycle may be about 5 Hz.

For example, the frequency of the pulsed duty cycle may be 5 Hz for a duty cycle at 80 percent with a period of 200 ms. The pulsed duty cycle may have period of about 0.5 second to 5 seconds. In a preferred embodiment, the pulsed duty cycle may have a period of about 3 seconds to collect a sufficient amount of biological sample for testing. In a preferred embodiment, the voltage may be applied for a duration of 1 to 20 seconds.

In an exemplary embodiment, an electrical voltage of 2.2 V may be applied to the disruptor 202 with pulsed duty cycle of 80% for 3 seconds to generate temperature of 140° C. If disruptor 202 has the dimensions of about 100 μm×200 μm and electrical resistance of 22 Ohm, the power (P) over Area required to generate the required heat may be 5 W/mm² which may be calculated using the following equations:

$$P=I^2R=V^2/R=2.2V/22\ Ohm=0.1\ W$$

where
R=V/I and where,
Power P is in Watts;
Voltage V is in volts; and
Resistance R is Ohms.

$$A=100\ \mu m \times 200\ \mu m=0.02\ mm^2$$

$$P/A=0.1\ W/0.02\ mm2=5\ W/mm^2$$

where,
P is power; and
A is area of the disruptor.

The energy (E) per unit area required to generate 140° C. of heat in the disruptor 202 may be measured by the following equations:

$$E/A=Pt/A=1\ J/mm^2$$

where,
Energy is measured in Joules,
t is time at 0.2 s of one pulse; and
A is the area of disruptor.

The amount of biological sample required to be obtained by the transdermal sampling and analysis device 200 to accurately determine levels of an analyte may be about less than 40 nl. In a preferred embodiment, the amount of biological sample obtained by the transdermal sampling and analysis device 200 may be about less than 10 nl. In a more preferred embodiment, the amount of biological sample obtained by the transdermal sampling and analysis device 200 may be about 5 nl.

In an embodiment method, voltage may be applied to the disruptor 202 in a manner to reduce the amount of sensation felt by the subject. One method of reducing sensation may be to gradually and in a stepwise manner raise the level of the voltage applied to the disruptor 202 until it reaches a desired voltage. For example, if 1.8 V produces the most amount of fluid, to reduce sensation the voltage may be pulsed at different intervals before reaching 1.8 V. For instance, the voltage may be pulsed five times at 1.2 V, five times at 1.4 V, and five times at 1.6 V before applying 1.8 V to the disruptor 202. In this embodiment method, the pulses at lower voltages may cause some biological sample fluid to flow from the skin 100. Even though this small amounts of the biological sample obtained at the lower voltages may not be enough to determine the levels of an analyte, the small amount of the biological sample may act as a thermal conductor to render the disruptor 202 more efficient and reduce the level of sensation felt by the subject at higher volts (i.e., 1.8 V). Thus, by increasing the voltage in a stepwise manner over a period of time, instead of applying the maximum voltage immediately, the same amount of biological samples may be obtained in the same amount of time while the amount of sensation may be reduced.

In addition, it may be noted that the application of electrical energy to the disruptor 202 may result in the formation of electrical fields surrounding the disruptor 202. The formed electrical fields may also alter the permeability characteristics of the stratum corneum. By increasing the localized electrical field formed by applying electrical energy to the disruptor 202, the permeability of the stratum corneum may also be increased. The increase in the permeability of the stratum corneum may require less heat imparted upon the stratum corneum to release a sufficient amount of biological fluid needed for an accurate analysis. Consequently, a lessening of the sensation or discomfort may be experienced by the subject.

Figure 9:
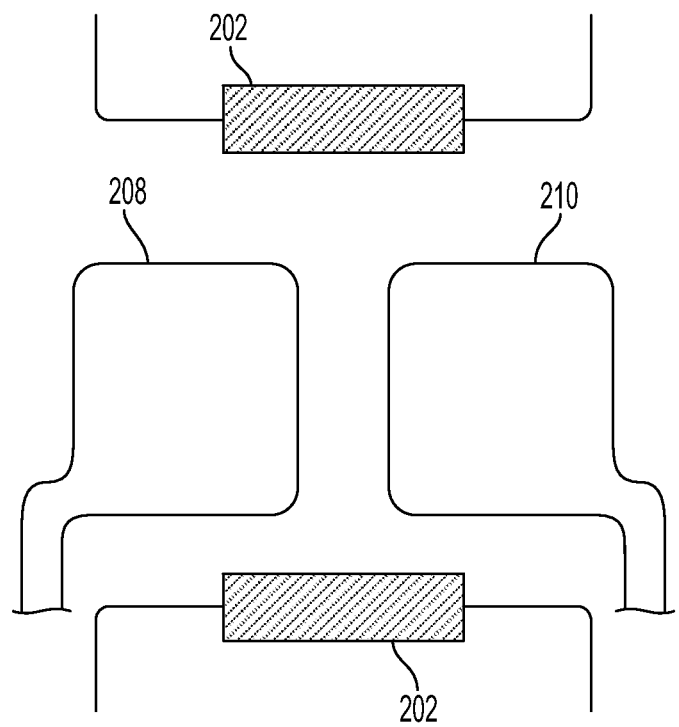
FIG. 9 illustrates a top view of a portion of an embodiment transdermal sampling and analysis device including two disruptors.

FIG. 9 illustrates a top view of an embodiment transdermal sampling and analysis device 200 using more than one disruptor 202. To increase the amount of disruption to the skin 100, a transdermal sampling and analysis device 200 may employ more than one disruptor 202. The disruptors 202 may be configured in a way to disrupt the skin cells and allow the flow of biological samples over the counter and working electrodes 208, 210 of the transdermal sampling and analysis device 200. By increasing the number of disruptor 202 sites, a larger volume of biological sample may be obtained in a shorter amount of time. This may result in a lessening of the experienced sensation or discomfort experienced by the subject. Additional biological samples obtained from the subject may enable a transdermal sampling and analysis device 200 to more accurately analyze the biological samples.

In the various embodiments, the transdermal sampling and analysis device 200 may include a reservoir 212 used to collect the biological samples that flow from the capillary-like channels of the skin. The reservoir 212 may be created by using processes and methods know in the art, such as by etching or arranging the transdermal sampling and analysis device 200 components in a manner to create a reservoir 212. For example, to create the reservoir 212, photoresist material may be applied to the first surface of the substrates 214 and patterns may be etched into the photoresist material to form the reservoir 212. Photoresists and their uses are well known in the art.

In an embodiment, the reservoir 212 may have a depth of about 20 μm to 100 μm. In a further embodiment, the reservoir 212 may have a depth of about 50 μm to 100 μm. In a preferred embodiment, the reservoir 212 may have a depth of about 30 μm. In a more preferred embodiment, the reservoir 212 may have a depth of about 60 μm.

The reservoir 212 may be created in a location where it can collect the biological samples that flow out of the capillary-like channels of the disrupted skin 100. Since the disruptor 202 creates the capillary-like channels in the skin 100 from where biological samples flow, the reservoir 212 may be positioned under or near the disruptor 202 to enable the transdermal sampling and analysis device 200 to collect the flowing biological samples. The reservoir 212 may comprise a collection reservoir 212a formed generally to surround the disruptor 202 and a sensing chamber 212b formed generally to contain the biological sample around the sensing elements such as counter and working electrodes 208, 210. The sensing chamber 212b portion of the reservoir 212 may contain the biological samples at one location where the samples may be analyzed by reacting with a biologically reactive element and interacting with the electrodes 208, 210. The reservoir 212 may further prevent the biological samples from flowing to other components of the transdermal sampling and analysis device 200 not configured to analyze the obtained samples.

To further guide the movement of the biological samples in the reservoir 212 and over the counter and working electrodes 208, 210, channels 222 may be created. In an embodiment, channels 222 may be formed using channel support structures 220 positioned in the reservoir 212 to facilitate and optimize the movement of the biological sample and the interactions of the sensors with the collected biological samples. The reservoir 212 and channels 222 may be created in a variety of shapes. For example, the reservoir 212 may be square, triangle, trapezoid, rectangle or circle and the channels 222 may be linear or circular.

Figure 10A:
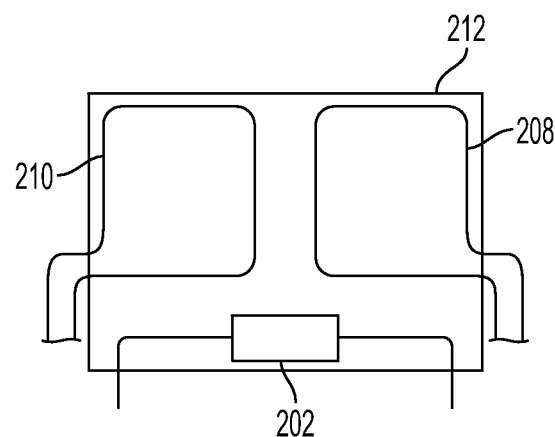
FIGS. 10A-10E illustrate top views of embodiment transdermal sampling and analysis devices having varying disruptor and reservoir configurations.
Figure 10B:
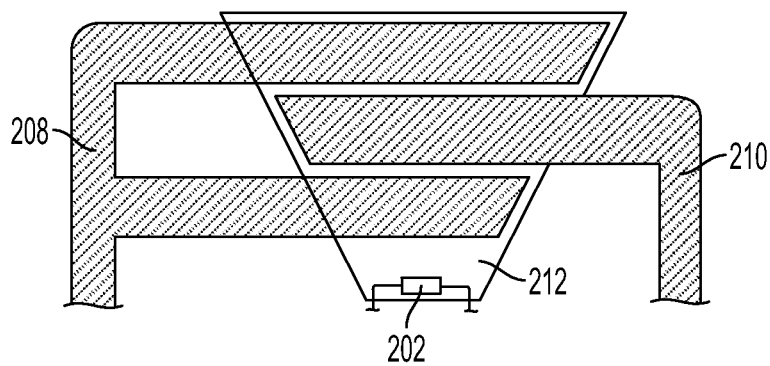
Figure 10C:
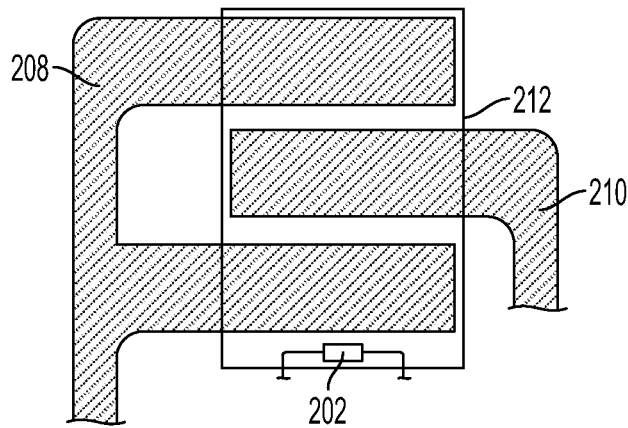
Figure 10D:
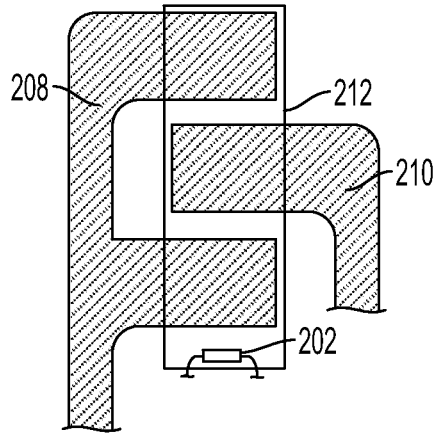

FIGS. 10A-10E illustrate top views of embodiment transdermal sampling and analysis devices 200 with different reservoir 212 and channel 222 shapes and configurations. FIG. 10A illustrates a top view of an embodiment transdermal sampling and analysis device 200 with a square shaped reservoir 212, wherein the counter and working electrodes 208, 210 may be positioned within reservoir 212 and one disruptor 202 may be also positioned within reservoir 212. FIG. 10B illustrates a top view of an embodiment transdermal sampling and analysis device 200 with a trapezoid shaped reservoir 212, the inter-digitated counter and working electrodes 208, 210 and disruptor 202 may be all positioned within the trapezoidal shaped reservoir 212. FIG. 10C illustrates a top view of an embodiment transdermal sampling and analysis device 200 with a rectangular shaped reservoir 212, the inter-digitated counter and working electrodes 208, 210 and disruptor 202 may be all positioned within the rectangular shaped reservoir 212. FIG. 10D illustrates a top view of an embodiment transdermal sampling and analysis device 200 with a narrow rectangle shaped reservoir 212, the inter-digitated counter and working electrodes 208, 210 and disruptor 202 may be all positioned within the narrow rectangular shaped reservoir 212.

Figure 10E:
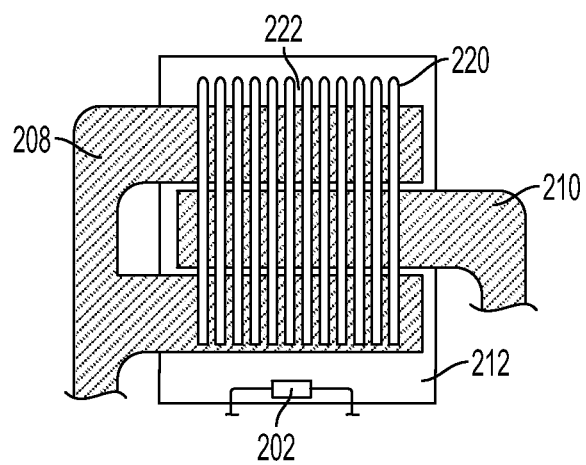

FIG. 10E illustrates a top view of an embodiment transdermal sampling and analysis device 200 with a rectangular shaped reservoir 212, two counter electrodes 208 and one working electrode 210 with inter-digitations and positioned in the reservoir 212 and a disruptor 202 also located in the reservoir 212. Long narrow channels 222 may be formed using several long channel supports 220 arranged in a parallel orientation with one another. The long channels 222 may function to facilitate the flow from where the biological samples away from the disruptor 202 and over the counter and working electrodes 208, 210 via capillary action.

Channel supports 220 may be employed for different purposes. For example, since a subject's skin comes into contact with the side of the transdermal sampling and analysis device 200 on which biological samples may be collected, the skin 100 may flex and dip in to the reservoir 212 and prevent the flow of the biological samples to the counter and working electrodes 208, 210. Channel supports 220 may be used to prevent the skin from blocking the flow of the biological sample to the counter and working electrodes 208, 210 by physically lifting the subject's skin 100 off of the transdermal sampling and analysis device 200 surface. Channel supports 220 may further facilitate an even flow of the biological sample over the entire surfaces of the working and the counter electrodes 208, 210.

In addition, the capillary force imparted by the channel supports 220 may be adjusted by varying the shape, structure, and hydrophilicity of the constituent materials of the channel supports. By selecting different materials from which to form the channel supports 220, the rate of flow of biological sample across the reservoir and surface of the counter and working electrodes 208, 210 may be altered. By selecting materials having greater hydrophilic characteristics the rate of flow across the reservoir may be augmented by the increase in surface tension between the biological sample and the supports of the hydrophilic channel supports 220. Thus, by choosing a material with a greater hydrophilic property from which to form the channel support 220, the flow rate of the biological sample to cover the counter and working electrodes 208, 210 may be increased, which in turn minimizes the volume of biological sample needed to complete an accurate analysis. The relative hydrophilic characteristic of a material is measured by its wetting angle. Materials suitable for the channel support 220 may have a wetting angle of less than 40° and more preferably less than 20°. By using materials having such hydrophilic characteristics, the sampled fluid may be drawn by capillary action and hydrophilicity along the channel supports 220 and to the back of the sensing chamber. Consequently, any trapped air within the sensing chamber or along the channels 222 formed between channel supports 220 may be directed back toward the disruptor 202.

Moreover, alternative configurations of the channel supports may increase the surface area of the channel support 220 support that comes into contact with the biological sample. By increasing the surface area of the channel support 220 support, an increase on the hydrophilic action may be realized.

In still further alternative configurations, by reducing the space between channel supports 220 at a desired location within the sensing chamber, capillary action may be increased. Consequently, the sampled fluid preferentially fills the sensing chamber. Capillary forces between structures within the remainder of the sensing chamber subsequently draw fluid from the first reservoir until the remainder of the sensing chamber is filled.

Figure 11A:
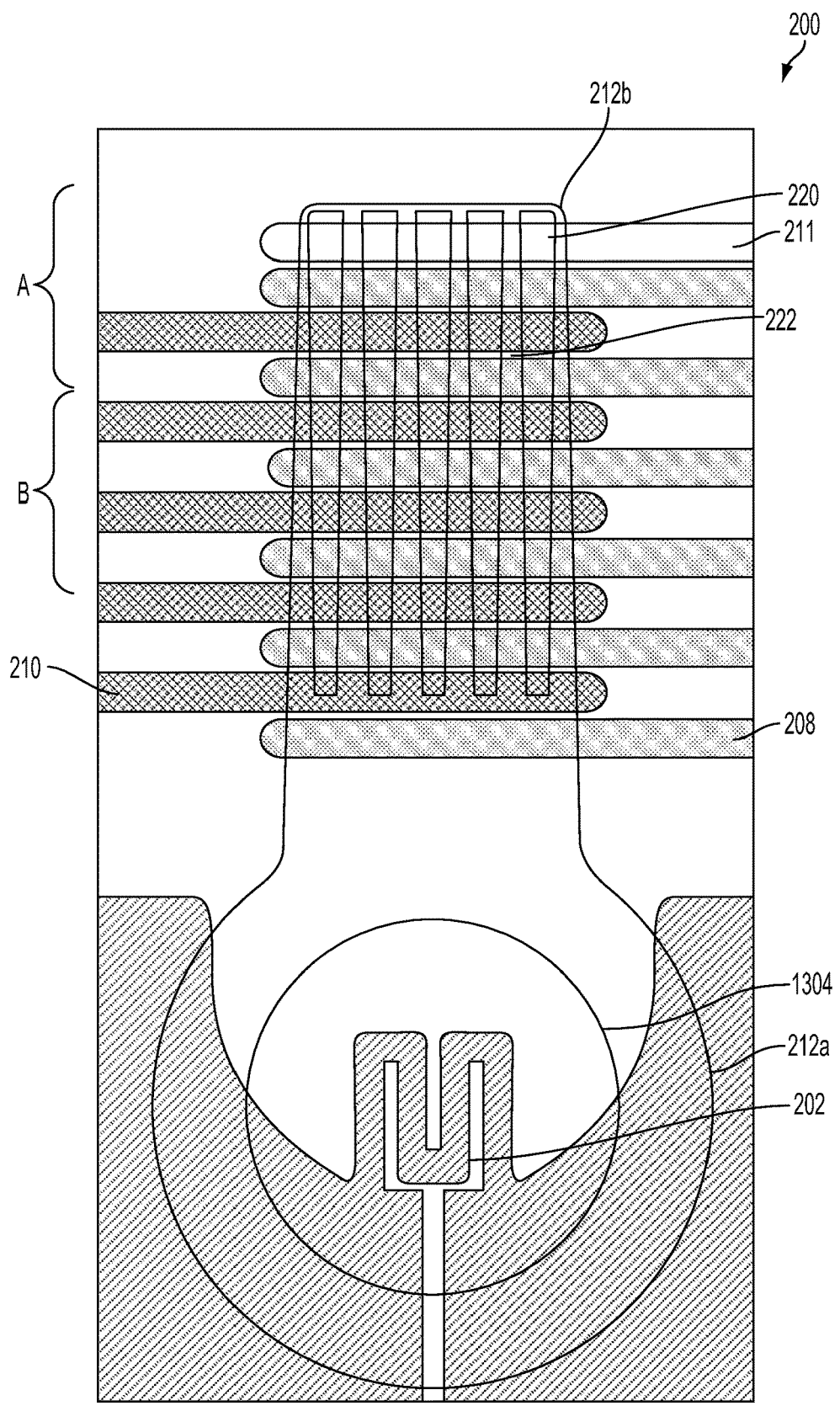
FIGS. 11A and 11B illustrate top views of embodiment transdermal sampling and analysis devices having varying channel support configurations.

FIG. 11A illustrates an alternative embodiment of the transdermal sampling and analysis device 200. Similar to the embodiment shown in FIGS. 10A-10E, the embodiment transdermal sampling and analysis device 200 shown in FIG. 11A includes a disruptor 202 having a serpentine configuration. The disruptor 202 may be positioned within a collection reservoir 212a. Leads capable of coupling the disruptor 202 to a voltage/current source may be extended to the corners of the transdermal sampling and analysis device 200. The disruptor 202 may be also positioned within an opening 1304 in a lid layer so that the disruptor 202 may be exposed to and may directly contact the subject's skin for disruption of the stratum corneum and the production of a biological fluid sample. The collection reservoir 212a portion of reservoir 212 may be interconnected with a sensing chamber 212b portion of reservoir 212. The sensing chamber 212b portion contains the produced biological fluid sample over counter and working electrodes 208, 210. The produced biological fluid sample may be directed over the entire surface of counter and working electrodes 208, 210 via channels 222 formed between channel supports 220. An optional reference electrode 211 may be also shown in FIG. 11A. The disruptor 202, counter and working electrodes 208, 210 and optional reference electrode 211 may be all formed on a substrate layer 214 (not shown in FIG. 11A). Channel supports 220 may be formed above the counter and working electrodes 208, 210 and optional reference electrode 211 in a spacer layer. The lid layer may be then adhered to the space layer above the channel supports 220.

As discussed above, the channel supports may be formed of hydrophilic materials having a wetting angle of less than 40° and more preferably less than 20° to induce a capillary action force and draw the generated fluid sample to the upper regions of the sensing chamber 212b portion. In addition, by varying the dimensions along the vertical axis of the channels 222, the capillary action may be increased, further forcing the generated fluid sample to the upper regions of the sensing chamber 212b portion. As shown in FIG. 11A, the dimension of channels 222 may be smaller in section A as compared to the dimension of channels 222 in section B. Consequently, a greater capillary action force may be imparted on the generated fluid sample due in large part to the increased contact with the constituent hydrophilic material of channel supports 220. Optimal channel 222 widths have been found to range from 70 µm to less than 50 µm, and most preferably less than 30 µm.

Figure 11B:
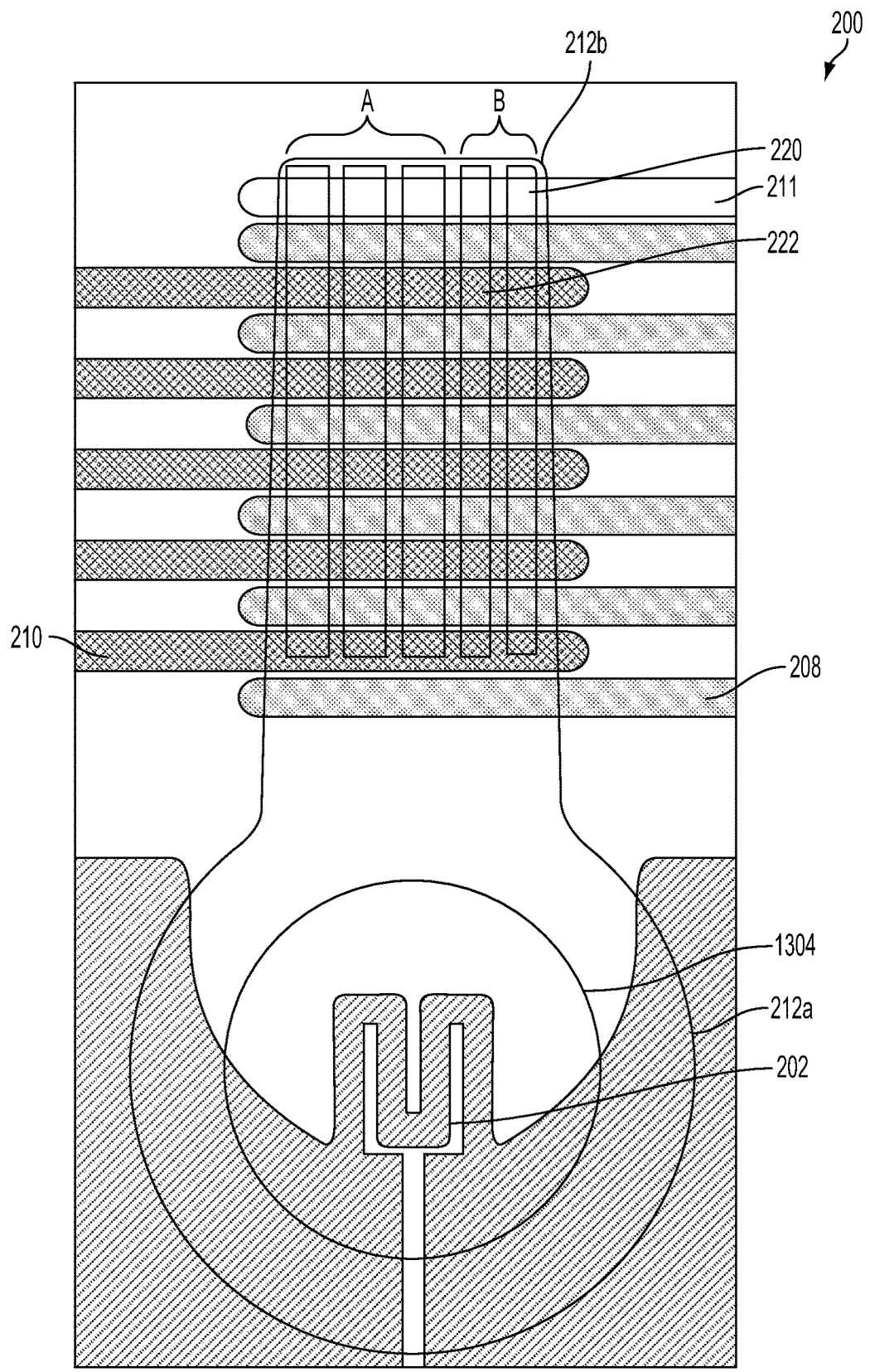

FIG. 11B illustrates another alternative embodiment of the transdermal sampling and analysis device 200, wherein the dimensions of each of the channels 222 along the horizontal axis may be varied. As shown in FIG. 11B, the channels 222 shown between channel supports 220 in region A may be narrower than the channels 222 shown between channel supports 220 in region B. In doing so, the generated fluid sample may be directed up through the channels 222 in region A on the left of the device 200 faster than the channels in region B on the right of the device 200. Thus, any trapped air in the channels 222 that might prevent the generated fluid sample from completely covering the electrodes 208, 210 in sensing chamber 212b may be effectively systematically pushed from one side of the sensing chamber 212b portion to the other so as to avoid trapping the air. Since a larger volume sensing chamber 212b portion requires a relatively large fluid sample to completely fill the sensing chamber 212b portion and insure complete coverage across counter and working electrodes 208, 210, the volume of the sensing chamber 212b portion may be varied. Moreover, larger volumes of fluid samples require more time to generate. Thus, optimal volumes for the sensing chamber 212b portion have been determined to be approximately less than 100 nanoliters (nl), and more preferably less than 20 nl, and most preferably 1 nl. Sensing chamber 212b portion widths may be smaller than 500 µm wide×1 mm long. Preferable dimensions may be below 250 µm wide, 500 µm long. Similarly, the size of the collection reservoir 212a portion may also impact the ability to obtain a viable fluid sample. The diameter of the collection reservoir 212a may be less than 1 mm and preferably between 500 and 800 µm.

Figure 12A:
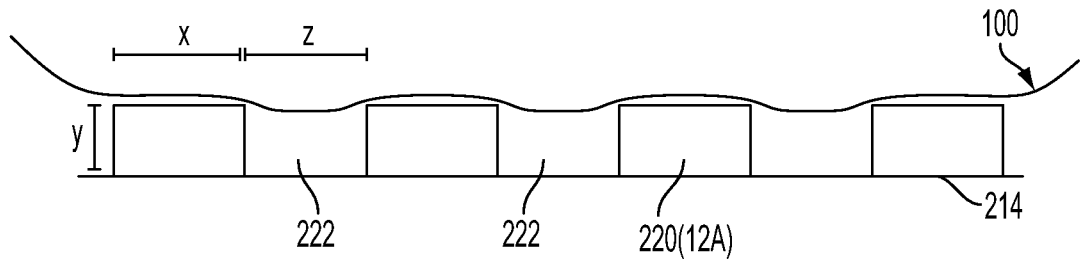
FIGS. 12A-12C illustrate cross-sectional views of channel supports of embodiment transdermal sampling and analysis devices.
Figure 12B:
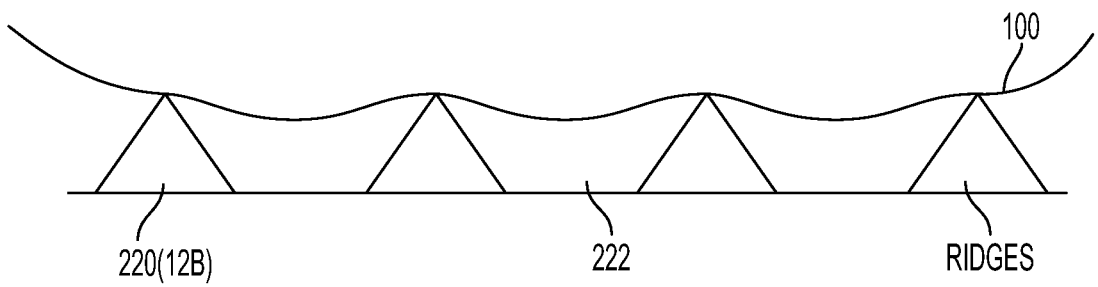
Figure 12C:
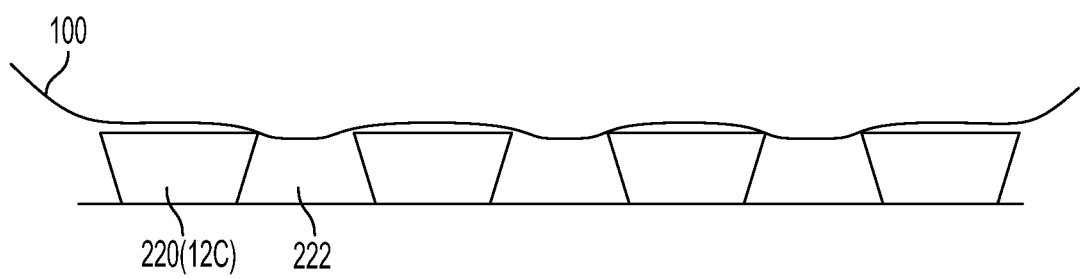

FIGS. 12A-12C illustrate different embodiment channel support 220 support configurations which offer varying amounts of surface area. FIG. 12A illustrates a cross-sectional view of several channel supports 220(12A) arranged in parallel orientation. The channels supports 220 (12A) may form a contact angle of 90° with the substrate 214. The space between two channel supports 220(12A) may create the channels 222. As the transdermal sampling and analysis device 200 comes into contact with the skin 100, the skin may rest on top of the channel supports 220(12A) and dip into the channels 222. If the distance between the two channel supports 220(12A) is too large, skin 100 may block the channel 222 by dipping far into it and touching the surface of the reservoir 212. If the distance of the channel supports 220(12A) is too small, the channel supports 220(12A) may effectively block a sufficient flow of the biological sample to the counter and working electrodes 208, 210.

FIG. 12B illustrates a cross-sectional view of several channel supports 220(12B) arranged in parallel orientation. The channels supports 220(12B) may form a contact angle greater than 90° with the substrate 214. The angled nature of the channel support 220(12B) supports increases the surface area channel support 220(12B) support, relative to channel supports 220(12A) shown in FIG. 12A. As discussed above, the increased surface area increases the amount of interaction between the channel support 220(12B) hydrophilic material and the biological sample. As a result, the flow of biological sample may be increased through the channels 222 relative to the configuration shown in FIG. 12A.

FIG. 12C illustrates an alternative cross-sectional view of several channel supports 220(12C) which increases, relative to channel supports 220(12A) shown in FIG. 12A, the surface area of the channel support 220(12C) material that may come into contact with the biological sample, which providing increased support to prevent the subject's surrounding skin from occluding the flow of the biological sample from the counter and working electrodes 208, 210. However, the configuration shown in FIG. 12C may decrease the volume of biological sample allowed to flow in each channel 222(12C), unless the distance between channel supports 220 may be increased as the volume of the channels 222(12C) may be decreased relative to the volume of the channels 222(12A) shown in FIG. 12A.

Another parameter of the channel supports 220 that may affect the functionality of the transdermal sampling and analysis device 200 may be the height of the channel supports 220 as compared to the distance the channel supports 220 may be positioned from the disruptor 202. If long channel supports 220 may be positioned too close to the disruptor 202, the height of the channel support 220 may prevent the skin 100 from coming into contact with the disruptor 202 when the transdermal sampling and analysis device 200 may be placed next to the skin 100. If short channel supports are positioned too far from the disruptor 202, the deformable subject's skin 100 may dip into a gap 1202 created between the channel support 220 and disruptor 202 and block the flow of the biological samples to the sensor electrodes.

Figure 13:
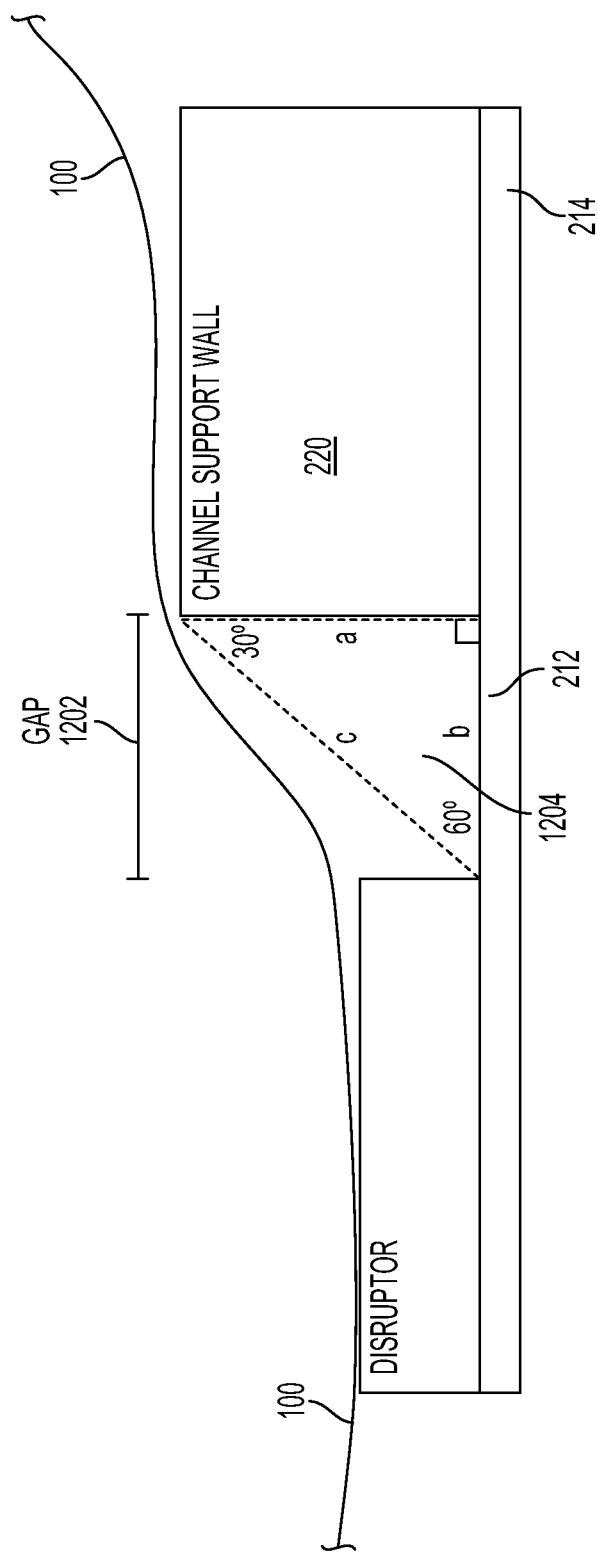
FIG. 13 illustrates a cross-sectional view of the relationship between the disruptor, reservoir and channel support of an embodiment transdermal sampling and analysis device.

FIG. 13 illustrates a cross-sectional view of an embodiment transdermal sampling and analysis device 200, showing a preferred method of determining the ratio between the height of a channel support 220 and its distance from the disruptor 202. The preferred distance to height ratio between the disruptor 202 and the channel supports 220 may be determined by using the ratio of the sides of a 30°-60°-90° triangle 1204. The 30°-60°-90° triangle 1204 side "a" may be used to determine the height of the channel support 220. The 30°-60°-90° triangle 1204 side "b" may be used to determine the distance of the channel support 220 to the disruptor 202. In an embodiment, the side "b" (i.e., the distance of the channel supports from the disruptor 202) may be about 0 µm to 30 µm. In a preferred embodiment, the side "b" may be about 30 µm and side "a" may be about 50 µm.

The biological sample collected by an embodiment transdermal sampling and analysis device 200 may escape from the reservoir 212 before it comes into contact with the counter and working electrodes. To ensure that the transdermal sampling and analysis device 200 has sufficient sample to perform the required analysis, different methods may be employed. For example, channels 222 may be used to facilitate the movement of the biological sample over the counter and sensing electrodes; hydrophilic channel support 220 material may be used to hold the biological samples attached to the channel supports 220 for a longer period of time; the disruptor 202 may apply heat to the skin for a longer period of time to keep the capillary-like opening of the skin open longer to obtain a larger amount of the biological sample; and/or a lid may be placed over the reservoir 212 to keep the biological sample from evaporating.

Figure 14A:
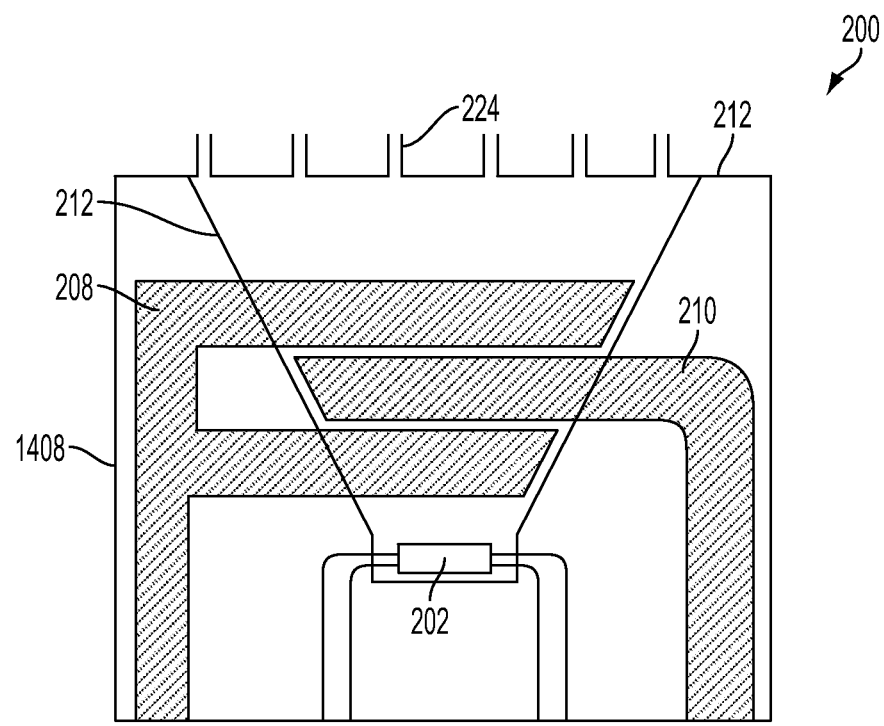
FIG. 14A illustrates a top view of a reservoir, sensors and disruptor of an embodiment transdermal sampling and analysis device.

In an embodiment, to more efficiently collect and maintain the biological fluid from the subject, a lid may be placed on the exposed side of the transdermal sampling and analysis device 200. FIG. 14A illustrates a top view of an embodiment transdermal sampling and analysis device 200 before a lid 1302 may be placed over the transdermal sampling and analysis device 200. The transdermal sampling and analysis device 200 includes counter and working electrodes 208, 210, a disruptor 202, and a reservoir 212 encompassing the disruptor 202 and counter and working electrodes 208, 210. Air vents 224 may be shown coupled to the reservoir 212 to allow air to escape as the biological sample flows to fill the reservoir from the disruptor 202 site to the top of the reservoir 212. A spacer layer 1408 may be formed over portions of the counter and working electrodes 208, 210. The spacer layer 1408 may effectively form the walls of reservoir 212.

Figure 14B:
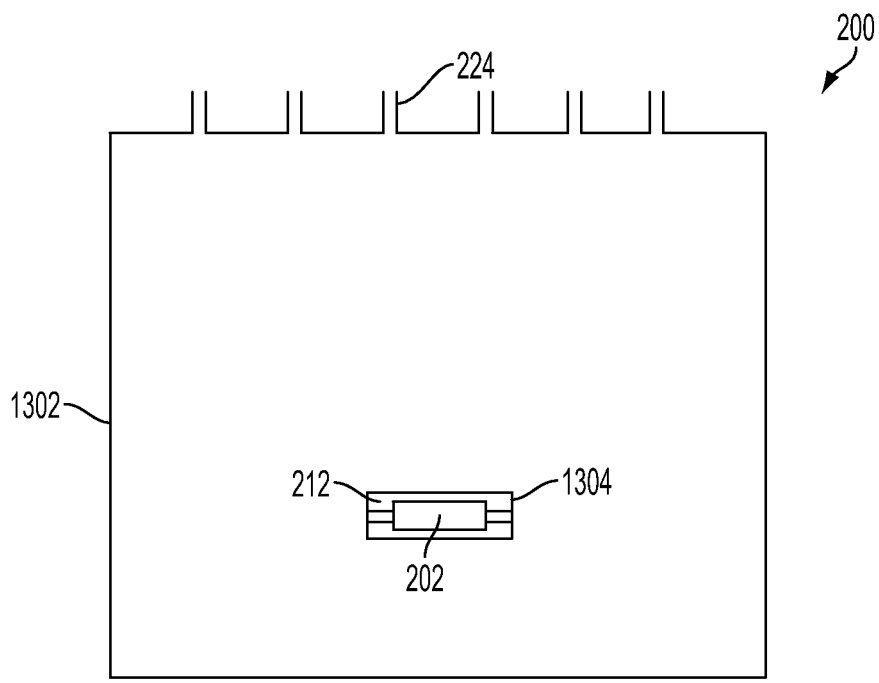
FIG. 14B illustrates a top view of a transdermal sampling and analysis device with the lid according to an embodiment.

FIG. 14B illustrates the same transdermal sampling and analysis device 200 after a lid 1302 may be placed over the elements of the transdermal sampling and analysis device 200 and spacer layer 1408. The lid 1302 partially covers the reservoir 212 to encapsulate the obtained biological sample. The lid effectively creates a closed volume defined by the reservoir 212 and the lid 1302. Without the use of a lid, the biological sample may be contained within the reservoir 212 by applying sufficient pressure to the transdermal sampling and analysis device 200 against the subject skin. In effect the subject skin acts as a lid to contain the biological sample within the reservoir 212. When a lid 1302 is placed over the reservoir 212, it may be necessary to include air vents 224 to allow air from escaping as the biological sample flows from one side of the reservoir 212 to another.

The lid 1302 may cover the entire surface of the transdermal sampling and analysis device 200 with the exception of the disruptor 202. In an embodiment, a hole 1304 may be carved in the lid 1302 to allow the disruptor 202 to be exposed while the other parts of the transdermal sampling and analysis device 200 may be covered. The hole may allow the disruptor 202 to come into contact with the skin 100 thus effecting adequate heating of the stratum corneum to cause disruption. The hole 1304 may also guide the biological fluid to flow into the reservoir 212. In a preferred embodiment, the hole 1304 has a diameter (or width) dimension of about 500 µm.

The lid 1302 that may be placed over the reservoir 212 may be made of a material such as plastic, metal, ceramic, or polymer. In a preferred embodiment, the lid 1302 may be made from a polymer. The lid 1302 thickness should be minimal to enable contact between the user's skin and the disruptor 202 with a minimal first reservoir 212a diameter. However, the lid 1302 should be thick enough to maintain chamber integrity in the presence of the pressure required to achieve intimate contact between the user's skin and disruptor. The lid 1302 (and adhesive layer adhering the lid 1302 to the spacer layer 1408 discussed in more detail below with respect to FIGS. 15A-15C) may have a thickness of about 10 µm to 75 µm. Preferably, the lid 1302 may have thickness of about 15-30 µm. The inner surface of the lid 1302 may be hydrophilic, preferably having a wetting angle of less than 50°, and more preferably less than 20°.

In an embodiment, instead of creating the channels 222 in the reservoir 212, channels 222 may be formed on the side of the lid 1302 that may be closer to the substrate when the lid 1302 is placed on the transdermal sampling and analysis device 200. In such a configuration, the reservoir 212 may be constructed without channels 222. The lid 1302 may include channel supports 220 and channels 222. Once the lid 1302 is positioned on the transdermal sampling and analysis device 200, the channels supports 220 of the lid 1302 may create channels 222 in the reservoir 212. This may be useful in the manufacturing process, where channels 222 created in the reservoir 212 may clog when the biologically reactive element is applied to the surface of the electrodes 208, 210. By including the channel supports 220 in the lid 1302, the biologically reactive element may be applied to the surface of the reservoir 212. The channels 222 may then be formed on top of the biologically reactive elements in the reservoir 212 once the lid 1302 is positioned on the transdermal sampling and analysis device 200.

Figure 15A:
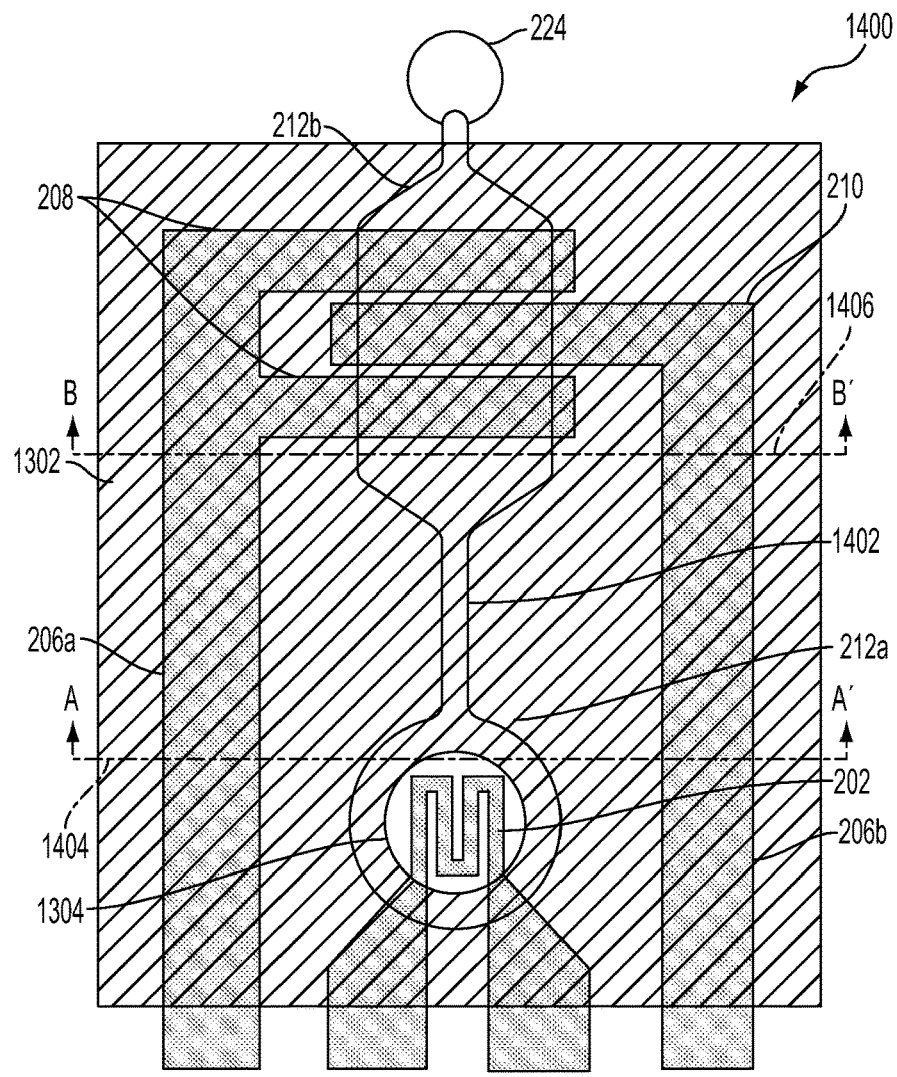
FIG. 15A illustrates a top view of a transdermal sampling and analysis device according to an embodiment.

FIG. 15A illustrates a top view of an embodiment transdermal sampling and analysis device 200. The transdermal sampling and analysis device may include a substrate 214 (shown in FIGS. 15B and 15C), a disruptor 202 located within a collection reservoir 212a portion, a reservoir connector channel 1402 which connects the collection reservoir 212a portion to a sensing chamber 212b portion. The sensing chamber 212b may be disposed over (or under) one working electrode 210 and two counter electrodes 208. The sensing chamber 212b may allow the biological sample to collect over the counter and working electrodes 208, 210, respectively. A biologically reactive element (not shown) may also be applied in the sensing chamber and over the counter and working electrodes 208, 210. The counter and working electrodes 208, 210 may be connected to electrical conductive paths 206a, 206b, respectively. A vent hole 224 may be present at the distal end of the sensing chamber 212b to allow air to escape as the biological sample moves from the collection reservoir 212a to the sensing chamber 212b through the reservoir connector channel 1402.

The width of the reservoir connector channel 1402 may affect the distance between the disruptor 202 and the counter and working electrodes 208, 210. For example, a narrow reservoir connector channel 1402 may allow small amounts of fluid to be directed from the collection reservoir 212a to the sensing chamber 212b. A wide reservoir connector channel 1402 may be used for directing larger amounts of biological sample from the collection reservoir 212a to the sensing chamber 212b. Thus, to direct small amounts of fluid from the first to sensing chamber in a transdermal sampling and analysis device 200 with a wide reservoir connector channel 1402, the distance between the disruptor 202 and the counter and working electrodes 208, 210 may be minimized as compared to a transdermal sampling and analysis device 200 with a narrow reservoir connector channel 1402. In a preferred embodiment, the reservoir connector channel 1402 may be 30-100 µm wide and 200-500 µm long.

As mentioned above, the transdermal sampling and analysis device 200 may further include a lid 1302 with a lid opening 1304. The lid opening 1304 may be located over the disruptor 202 to allow the disruptor 202 to come into direct contact with the subject's skin and as well as provide an open path for interstitial fluid to flow out of the stratum corneum and into the collection reservoir 212a. The disruptor 202 may be coupled to a signal generator (not shown). The opening 1304 in the lid 1302 exposes the disruptor 202 and allow contact between the disruptor 202 and the users' skin should be smaller in diameter than the collection reservoir 212a to enhance the collection of the fluid sample. For a 750 µm collection reservoir 212a diameter, the lid opening 1304 should be between 200 μm and 1 mm, preferably between 300-700 μm, and most preferably 500 μm.

Figure 15B:
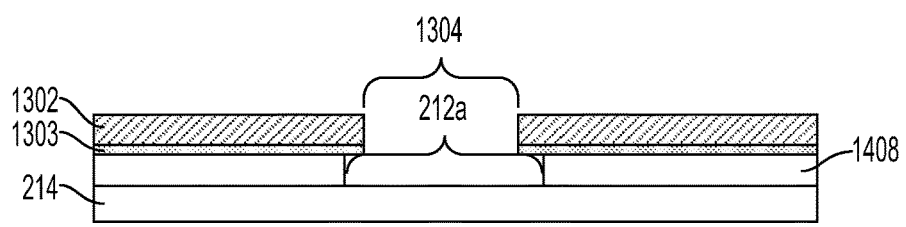
FIGS. 15B and 15C illustrate cross-sectional views of the relationship of different layers the transdermal sampling and analysis device of FIG. 15A.

FIG. 15B illustrates a cross-sectional view of the transdermal sampling and analysis device 200 along reference points AA' and reference line 1404. The arrows on the cross-section reference line 1404 shows the direction of the cross-sectional view. The transdermal sampling and analysis device 200 may be comprised of several layers including a substrate layer 214, a spacer layer 1408 and a lid layer 1302. Referring to FIG. 15B. the lid 1302 may be adhered to the spacer layer 1408 using an adhesive layer 1303. The total thickness of the lid 1302 with adhesive layer 1303 should be between 10-75 μm, and preferably between 15-30 μm. The lid adhesive layer 1303 may itself have a thickness of between 5-20 μm, and preferably between 3-10 μm. If the thickness of the adhesive layer is too thick, the adhesive may flow into the first reservoir 212a and sensing chamber 212b, as well as reservoir connector channel 1402 when applied. However, if the thickness of the adhesive layer 1303 is insufficient, it may not flow and completely seal the lid 1302 to the spacer 1408. In addition, the adhesive layer 1303 should be sufficiently flat when applied so as to seal the surface of the spacer layer 1408 with minimal flow upon application. The surface of the adhesive layer should have an RMS roughness value of Ra below 3 μm, and preferably below 1 μm. The adhesive layer 1303 should exhibit hydrophilicity, having a wetting angle below 40° and preferably below 20°. The adhesive layer 1303 material should exhibit flow characteristics having Tg between 0 and 50° C., preferably between 0 and 30° C., and most preferably between 10 and 20° C.

The spacer layer 1408 may separate the substrate layer 214 and the lid layer 1302. The first reservoirs 212a and sensing chamber 212b and the reservoir connector channel 1402 may be created by the spacer layer 1302 using methods as described above. The spacer layer 1408 may be 10 and 70 μm thick and may be selected from a material such as polymer or ceramic. It should be noted that if the thickness of the spacer layer 1408 is too thick, the user's skin will be effectively spaced away from the disruptor 202 formed on a substrate 214. As the diameter of the first reservoir 212a may be decreased, it becomes increasingly difficult for the user's skin to deflect into the first reservoir 212a and come into contact with the disruptor 202. Accordingly, as the diameter of the first reservoir 212a may be decreased, the thickness of the spacer layer 1408 must also be decreased. The thickness of the spacer layer 1408 may be between 10 and 50 μm, and most preferably between 15 and 30 μm for a first reservoir having a diameter of 750 μm.

The collection reservoir 212a may be located within the hole 1304 and surrounding the disruptor 202 to allow the biological sample to collect in the collection reservoir 212a. As shown in FIG. 15B, the width of the collection reservoir 212a may be slightly larger than the width of the hole 1304 in the lid 1302. Electrically conductive paths 206a, 206b may be located between the substrate layer 214 and spacer layer 1302. The electrically conductive path 206a connects to the counter electrode 208 and the electrically conductive path 206b connects to the working electrodes 210. It may be noted that the thickness of the electrically conductive paths 206a and 206b may be such that in comparison to the thickness of the substrate 214, spacer 1408 and lid 1302 layers, the conductive path layers may not be seen in the cross sectional view.

Figure 15C:
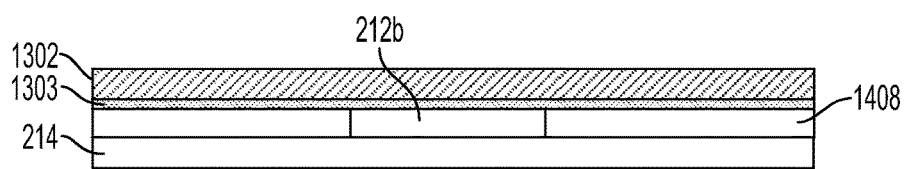

FIG. 15C illustrates a cross-sectional view of the transdermal sampling and analysis device 200 along reference points BB' and reference line 1406. The arrows on the cross-section line 1404 shows the direction of the cross-sectional view. At this cross-section, the transdermal sampling and analysis device 200 may include a substrate layer 214, a spacer layer 1408 and a lid layer 1302. The spacer layer 1408 may form the boundaries of the sensing chamber 212b. By adhering the lid 1302 fully over the sensing chamber 212b, the biological sample may be prevented from evaporating or pouring out of the transdermal sampling and analysis device 200 and adequately react with the biologically reactive element in the sensing chamber 212b.

Figure 16:
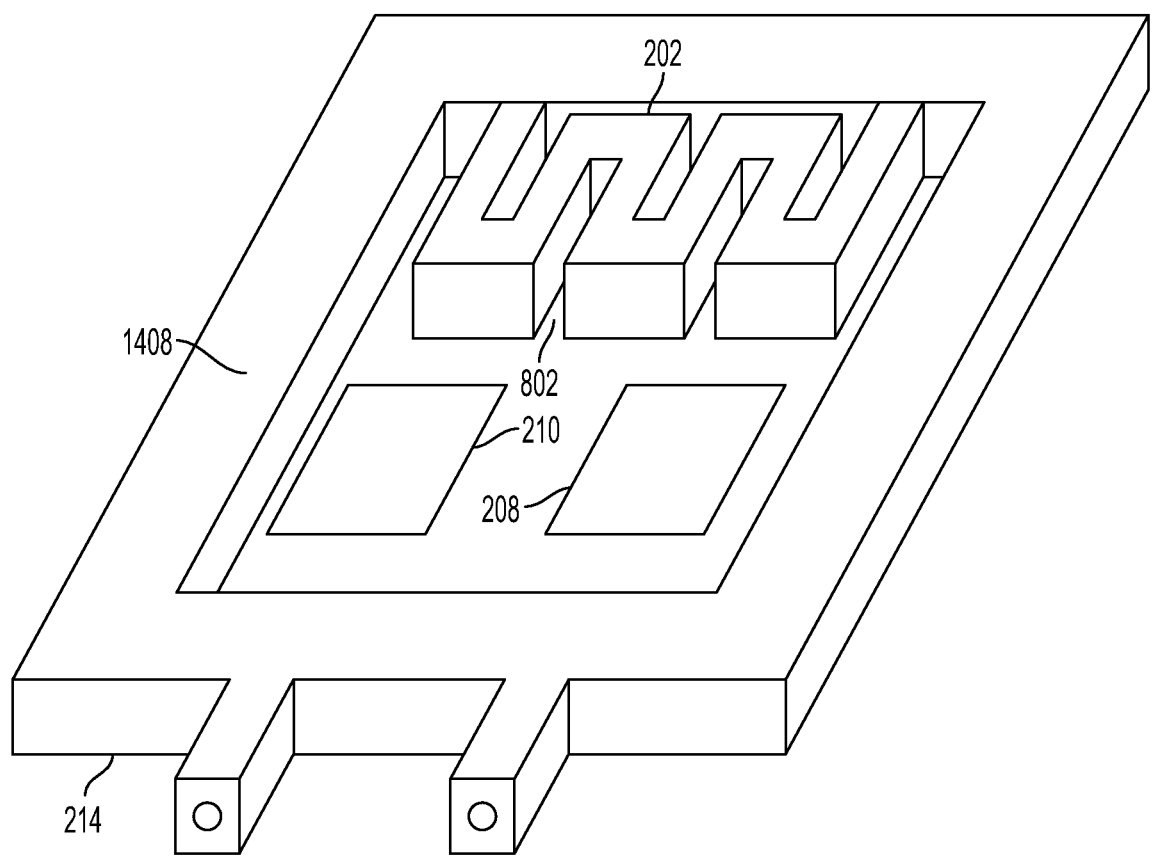
FIG. 16 illustrates a perspective view of the raised disruptor of an embodiment transdermal sampling and analysis device.

FIG. 16 is a perspective view of an embodiment transdermal sampling and analysis device 200 using a raised disruptor 202. The transdermal sampling and analysis device 200 shown in FIG. 16 is shown without a lid. The transdermal sampling and analysis device 200 is shown to have a raised disruptor 202. Raising the disruptor 202 may assure good contact of the disruptor 202 to the skin 100, which may be advantageous with increasing channel support 220 height. Another advantage of using a raised disruptor 202 may be that it acts much like the channel supports which displace the skin 100 from the surface of the electrodes so that the biological sample may flow freely over the surface of the electrodes. This configuration may also allow for creation of channels in the gap between the coils 802 of serpentine disruptors 202 which assist in increasing the flow of the obtained biological sample. A spacer layer 1408 may disposed on the substrate 214 to form a reservoir 212 encompassing the counter and working electrodes 208, 210 so that a biological fluid sample generated when the disruptor 202 disrupts the subject's skin may be contained within the reservoir 212 and over the counter and working electrodes 208, 210. Any of a variety of manufacturing techniques may be employed to form the raised disruptor surface. For example, the layer of material used to form the disrupter may be deposited in a series of deposition steps to build up a sufficient layer before excess material may be etched away in a photolithography process. Alternatively, the deposition process itself may be used to continuous deposit material in the form of the disruptor to build up the raised disruptor structure. As discussed above, a biological sample may be tested for presence of an analyte (e.g., glucose) by applying a biologically reactive element to the sample (e.g., an enzyme). In the various embodiments, the biological sample (e.g., interstitial fluid) may react with a biologically reactive element on the surface of the counter electrodes 208 and working electrodes 210. When interstitial fluid contacts a biologically reactive element on the surface of the counter and working electrodes 208, 210, it causes a chemical reaction that releases electrons. The products of the biochemical reaction between the biological sample and the biologically reactive element may be analyzed by the magnitude of the current that may be generated when the released electrons are transferred to the sensing electrode by the electron mediator.

Example biologically reactive elements may include, but are not limited to, glucose oxidase (GOD), glucose dehydrogenase, etc. In addition, in order to transfer released electrons to the one or both of the working and counter electrodes 208, 210, an electron mediator may be deposited in conjunction with the biologically reactive element. The electron mediator and biologically reactive element may be linked with a polymer to form a matrix, and the three materials together may constitute a sensing reagent. Example mediators that may be used include ferrocene, i.e., "Fc" ($Fe(C_5H_5)_2$), potassium ferrocyanide ($K_3Fe(CN)_6$), ferrocenecarboxaldehyde ($C_{11}H_{10}FeO$), etc. Thus, in an embodiment device that uses interstitial fluid to test for glucose, the biologically reactive element glucose oxidase (GOD) may be applied to at least one sensing electrode in a matrix with the electron mediator ferrocene (Fc) and a polymer linear polyethyleneimine (I-PEI) to form the sensing reagent (I-PEI-Fc/GOD matrix).

As discussed above, various embodiments may implement narrow channels formed in the sensing chamber between several channel supports aligned in a parallel block. The channels may facilitate flow of the biological sample away from the disruptor 202 and collection reservoir 212a and over the counter and working electrodes 208, 210.

In the various embodiments discussed above, channel supports 220 may be tapered such that the channels 222 formed between the channel supports 220 are narrower at the end of the sensing chamber that is farthest from the collection reservoir 212a. The channel supports 220 may be formed using hydrophilic materials, which promote adhesion forces between the biological fluid and the channel supports 220. The adhesion forces may increase as the taper of the channel supports 220 increases such that the channel supports 220 get thicker. Coupled with the fact that surface tension of the biological sample (i.e., cohesive forces of the fluid) increases with narrower channels, the farthest end of the sensing chamber 212b may exert strong capillary force on the biological sample. The capillary action may force the interstitial fluid to fill the sensing chamber 212b from the farthest end of the sensing chamber 212b toward the collection reservoir 212a to avoid trapping bubbles.

The various embodiments shown in FIGS. 10F and 10G have exhibited excellent characteristics in directing the flow of generated biological fluid samples in the collection reservoir 212a across the entirety of the counter and working electrodes 208, 210 in the sensing chamber 212b. However, in some instances it has been observed that when the sensing reagent is applied to the counter and working electrodes 208, 210, the addition of the sensing reagent causes the formation and collection of air bubbles in the sensing chamber 212b. These air bubbles prevent the generated biological fluid from completely covering the counter and working electrodes 208, 210 in the sensing chamber 212b. One reason for this result may be that the sensing reagent causes a greater hydrophilic environment in the sensing chamber 212b. Consequently, the generated biologic fluid may tend to bridge across the channel support members 220 instead of following the edge of the sensing chamber 212b and up each of the channels 222. The bridging of the fluid over channel support members 220 may permit an air bubble(s) to form, thereby blocking the flow of biological fluid across the entirety of the counter and working electrodes 208, 210 and signal therefrom.

Multiple design configurations, illustrated in FIGS. 17A-17G may be used in the various embodiment transdermal sampling and analysis devices to mitigate against the formation of air bubbles in the sensing chamber 212b when a sensing reagent is employed. By measuring parameters such as fill rate, sensation, and bubble formation for each embodiment design, it may be determined that shortening the height of each channel 222 relative to its width may mitigate bubble formation. For example, the six channels 222 shown in FIGS. 11A and 11B may each have a height of about 500 µm, and may each have an average width of about 30 µm. In order to prevent bubble formation, the aspect ratio of channel height to width may be decreased in various embodiments by shortening the heights of the channels 222 to about 250 µm. Thus, in an embodiment, the aspect ratio of each channel 222 may be less than 10:1. In a preferred embodiment, the aspect ratio of each channel 222 may be about 5:1, and more preferably 2:1. In this manner bridging of biological fluid may be prevented, since the distance the biological fluid travels in the sensing chamber 212b (i.e., down channels 222) may be a much shorter path as compared to previously described embodiments. Embodiment designs configured using these aspect ratios of channel 222 height to width may therefore significantly lower the formation of air bubbles that prevent the biological fluid sample from flowing over the entirety of the sensing chamber 212b.

Figure 17A:
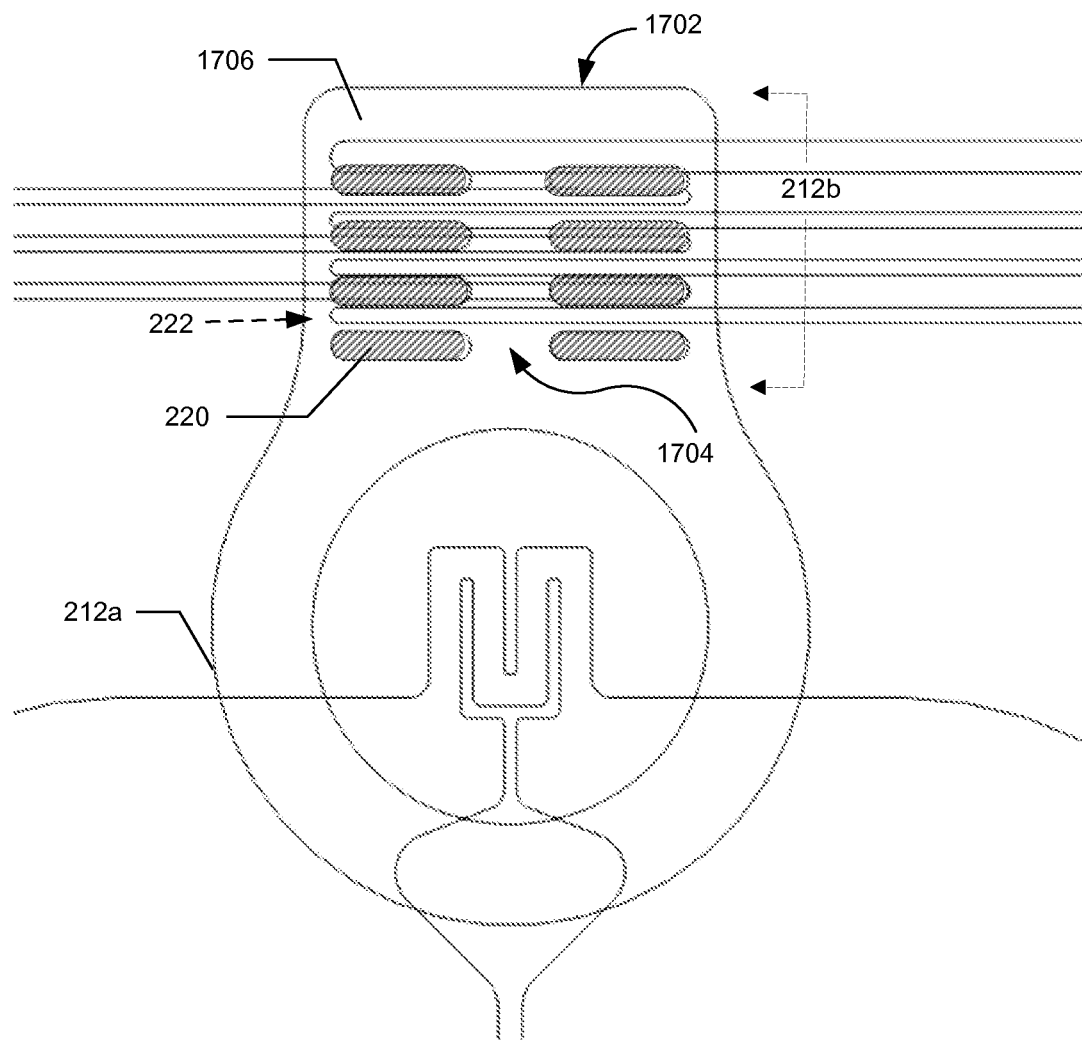
FIGS. 17A-17G illustrate top views of various embodiment transdermal sampling and analysis devices.

FIG. 17A illustrates an embodiment transdermal sampling and analysis device wherein the aspect ratio of the height of each channel to the width of each channel is less than 10:1. As shown in FIG. 17A, the sensing chamber 212b may contain parallel channel supports 220 a horizontal configuration. Consequently, the sensing chamber may include a central channel 222c, and edge channels 222a and 222b. In addition, due to the horizontal configuration of the channel supports 220, additional horizontal channels 1704 may be formed between the channel supports 220. Each of the central channel 222c and edge channels 222a and 222b may be configured with an aspect ratio that is less than or equal to approximately 10:1. For example, the height of edge channels 222a and 222b may be about 250 µm, and the width of each channel may be about 30 µm. The height of the central channel 222c may be about 250 µm, and the width of the central channel 222c may be about 90 µm. Thus, the aspect ratio of the central channel 222c may be about 3:1 (i.e., less than 10:1). As with other embodiments, the channel supports 220 may prevent a lid 1302 from being deformed and encroaching into the sensing chamber 212b. The channel supports 220 may further possess hydrophilic properties which aid in the dispersion of the generated biological fluid across the entire surface of the sensing chamber 212b.

Figure 17B:
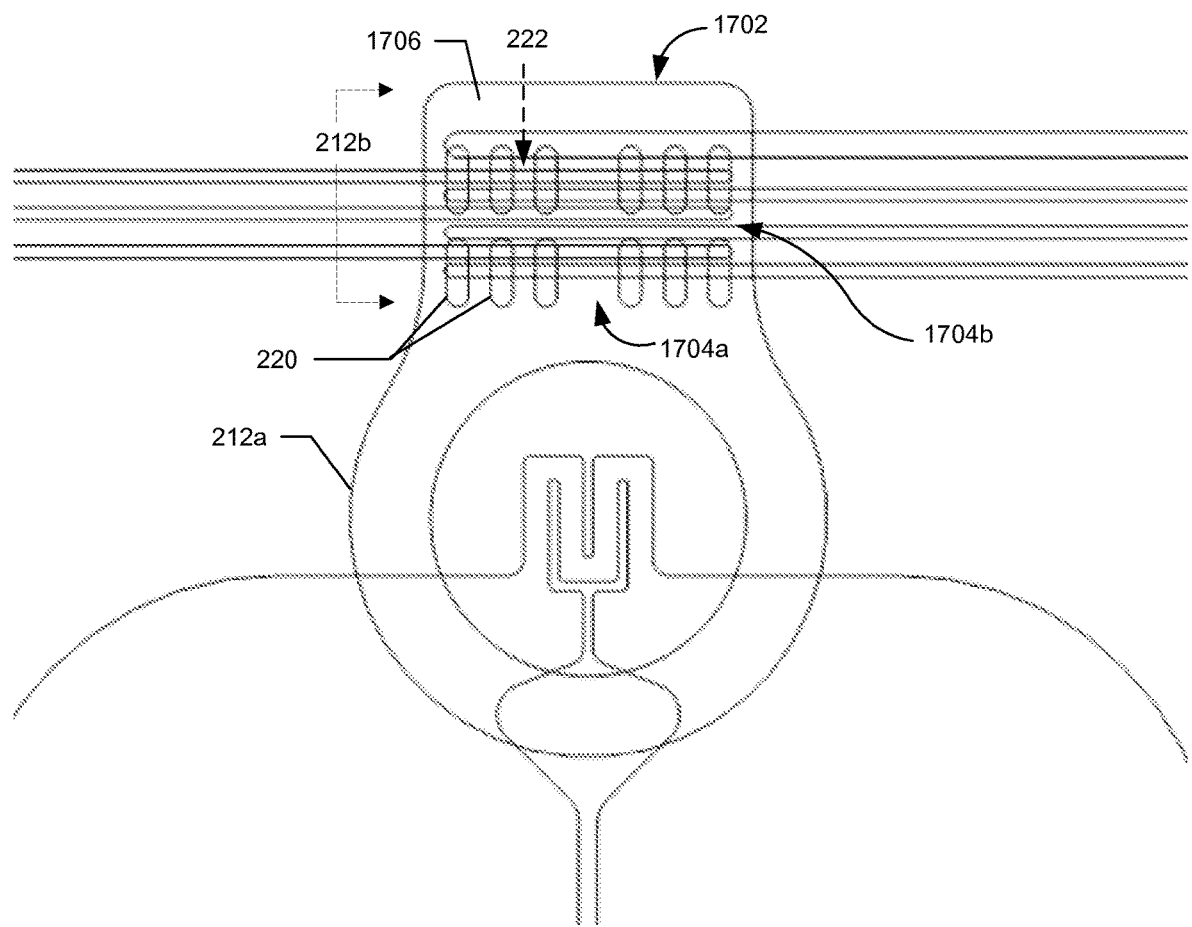

FIG. 17B illustrates another embodiment transdermal sampling and analysis device wherein the aspect ratio of the height of each channel to the width of each channel is less than 10:1. As shown in FIG. 17B, the sensing chamber 212b may contain channel supports 220, with channels 222 between adjacent channel supports 220. As shown in FIG. 17B, the channel supports 220 may be configured in a vertical formation with the channel supports 220 largely parallel to one another. The channel supports 220 may be divided into four groups configured to form a central channel 222c and vertical channels 222 between the channel supports 220. The channel supports 220 may also be configured to define edge channels 222a and 222b. Each of the channels 222, central channel 222c and edge channels 222a and 222b may be configured with an aspect ratio that is less than or equal to approximately 10:1. For example, the height of channels 222 as well as edge channels 222a and 222b may be about 250 µm, and the width of each channel may be about 30 µm. Thus, the aspect ratio of the channels 222 as well as edge channels 222a and 222b may be about 10:1. The height of the central channel 222c may be about 250 µm, and the width of the central channel 222c may be about 90 µm. Thus, the aspect ratio of the central channel 222c may be about 3:1 (i.e., less than 10:1). The configuration of channel supports 220 being divided into four groups may also provide the sensing chamber 212b with a horizontal channel 1704. The embodiment shown in FIG. 17B may also include a space 1706 between the channel supports 220 and end 1702.

Figure 17C:
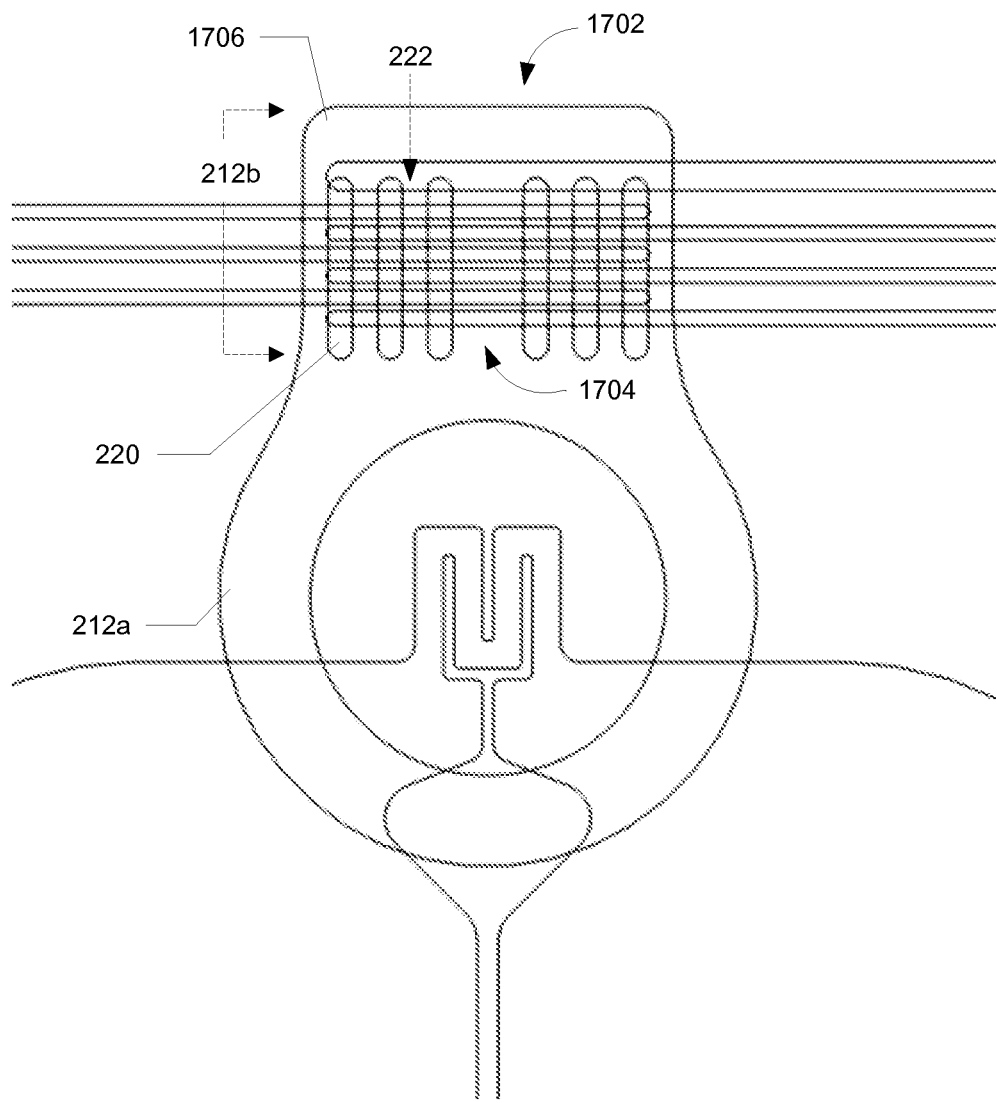

FIG. 17C illustrates another embodiment transdermal sampling and analysis device wherein the aspect ratio of the height of each channel to the width of each channel is less than 10:1. The sensing chamber 212b may contain channel supports 220, with channels 222 between adjacent channel supports 220, with a central channel 222c and edge channels 222a and 222b. As shown in FIG. 17C, the channel supports 220 may be configured in a vertical formation with the channel supports 220 largely parallel to one another. The channel supports 220 may be divided into two groups forming a central channel 222c between a group on the left side of the sensing chamber and a group on the right side. Each of the channels 222, central channel 222c and edge channels 222a and 222b may be configured with an aspect ratio that is less than or equal to approximately 10:1. For example, the height of channels 222 as well as edge channels 222a and 222b may be about 250 µm, and the width of each channel may be about 30 µm. Thus, the aspect ratio of the channels 222 as well as edge channels 222a and 222b may be about 10:1. The height of the central channel 222c may be about 250 µm, and the width of the central channel 222c may be about 90 µm. Thus, the aspect ratio of the central channel 222c may be about 3:1 (i.e., less than 10:1). The configuration of channel supports 220 being divided into four groups may also provide the sensing chamber 212b with a horizontal channel 1704. The embodiment shown in FIG. 17C may also include a space 1706 between the channel supports 220 and end 1702.

Figure 17D:
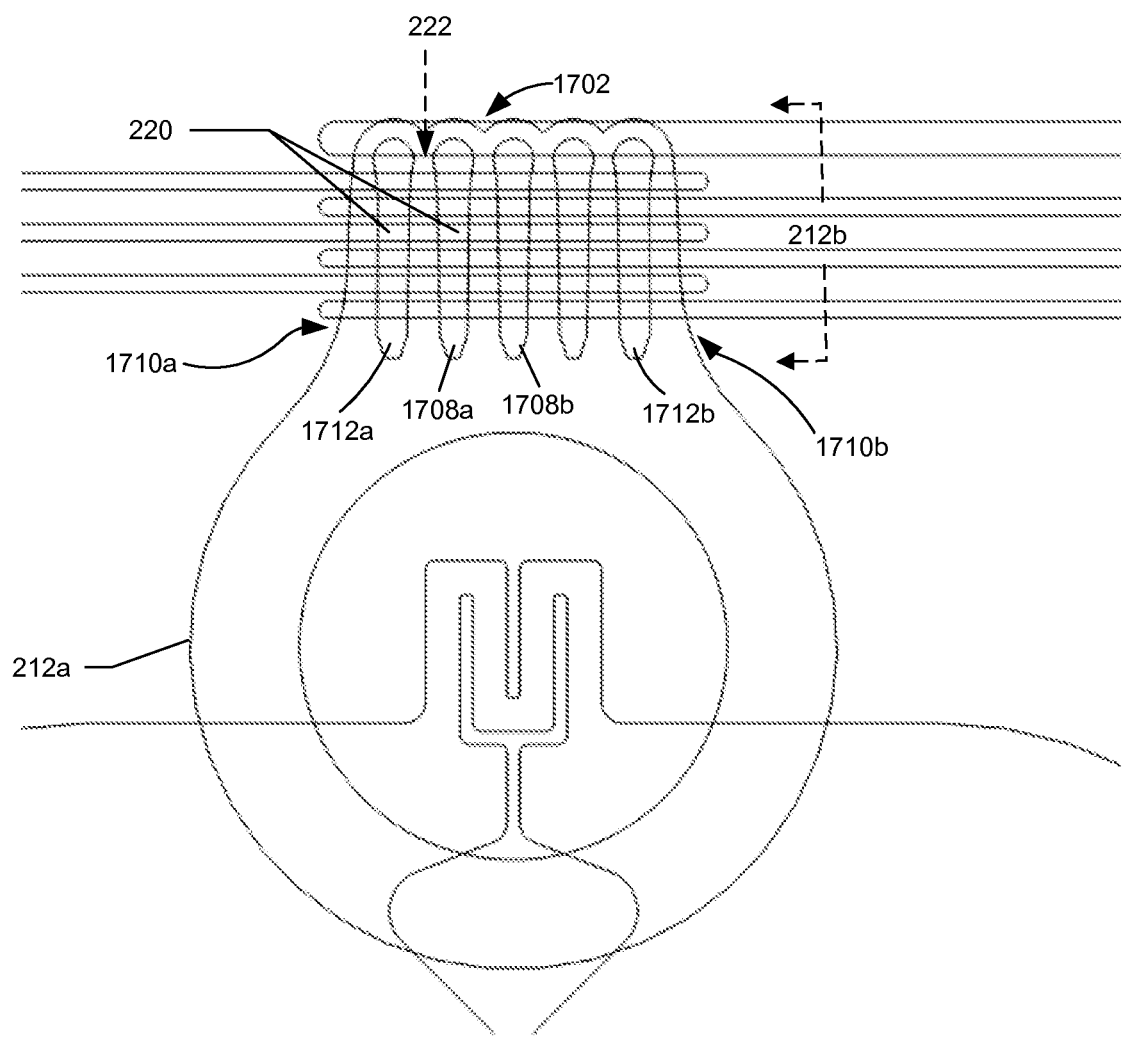

FIG. 17D illustrates another embodiment transdermal sampling and analysis device wherein the aspect ratio of the height of each channel to the width of each channel is less than 10:1. The sensing chamber 212b may contain channel supports 220, with channels 222 between adjacent channel supports 220. As shown in FIG. 17D, the channel supports 220 may be configured in a vertical formation with the channel supports 220 largely parallel to one another. In contrast to embodiments illustrated in FIGS. 17A-17C, the channel supports 220 may be tapered such that the width of each channel support 220 may be wider at the top and narrower at the bottom. Consequently, the channels 222 formed between the channel supports 220 are wider at the bottom and narrower at the top. Each of the channel supports 220 may be configured with a bulbous shape at the wider end at the top. In an example embodiment, the height of each channel 222 may be about 250 µm, while the distance between inner channel supports 1708a, 1708b may be about 23 µm near end 1702, and may be about 33 µm near the end closest to the collection reservoir 212a. Thus, the aspect ratio of each channel 222 may be less than or equal to 10:1. The sensing chamber 212b in this configuration may also have edges 1710a, 1710b that taper, and form a smooth surfaces at the intersection of the sensing chamber 212b and the collection reservoir 212a. As a result, the distance between the two outer channel supports 1712a, 1712b and edges 1710a, [1712b] 1710b may be greater at the lower end nearest the collection reservoir 212a and less at the top end nearest end 1702 of the sensing chamber 212b. In one example, the distance between outer channel supports 1712a, 1712b and edges 1710a, 1710b, respectively, may be about 38 µm.

Figure 17E:
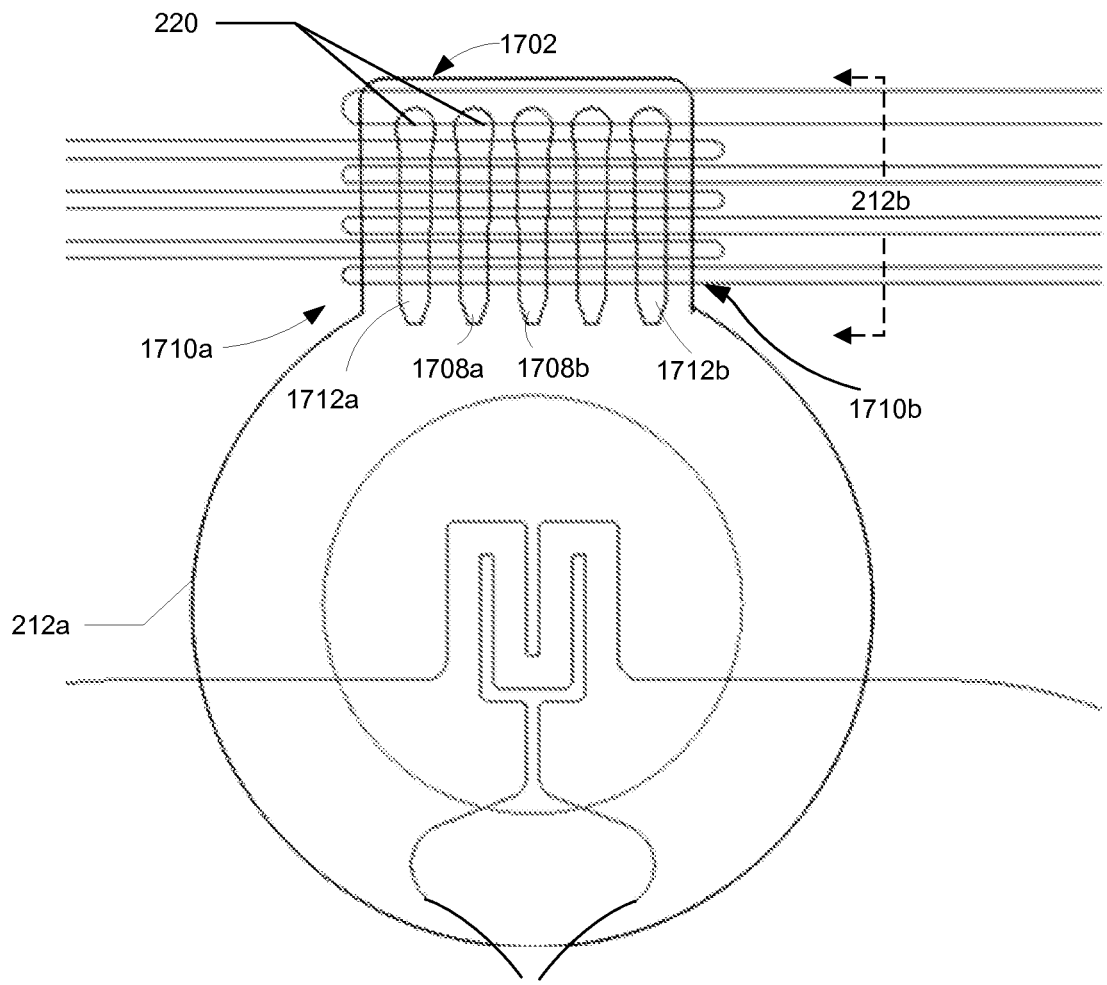

FIG. 17E illustrates an alternative embodiment transdermal sampling and analysis device wherein the aspect ratio of the height of each channel to the width of each channel is less than 10:1. The embodiment illustrated in FIG. 17E may be significantly similar to the embodiment illustrated in FIG. 17D. However, in the embodiment illustrated in FIG. 17E, the sensing chamber 212b in this configuration may also have edges 1710a, 1710b that do not taper. Thus, the edges 1710a, 1710b may form a sharp corner at the intersection of the sensing chamber 212b and the collection reservoir 212a. As a result, the distance between the two outer channel supports 1712a, 1712b and edges 1710a, 1710b may be consistent throughout the edges.

Figure 17F:
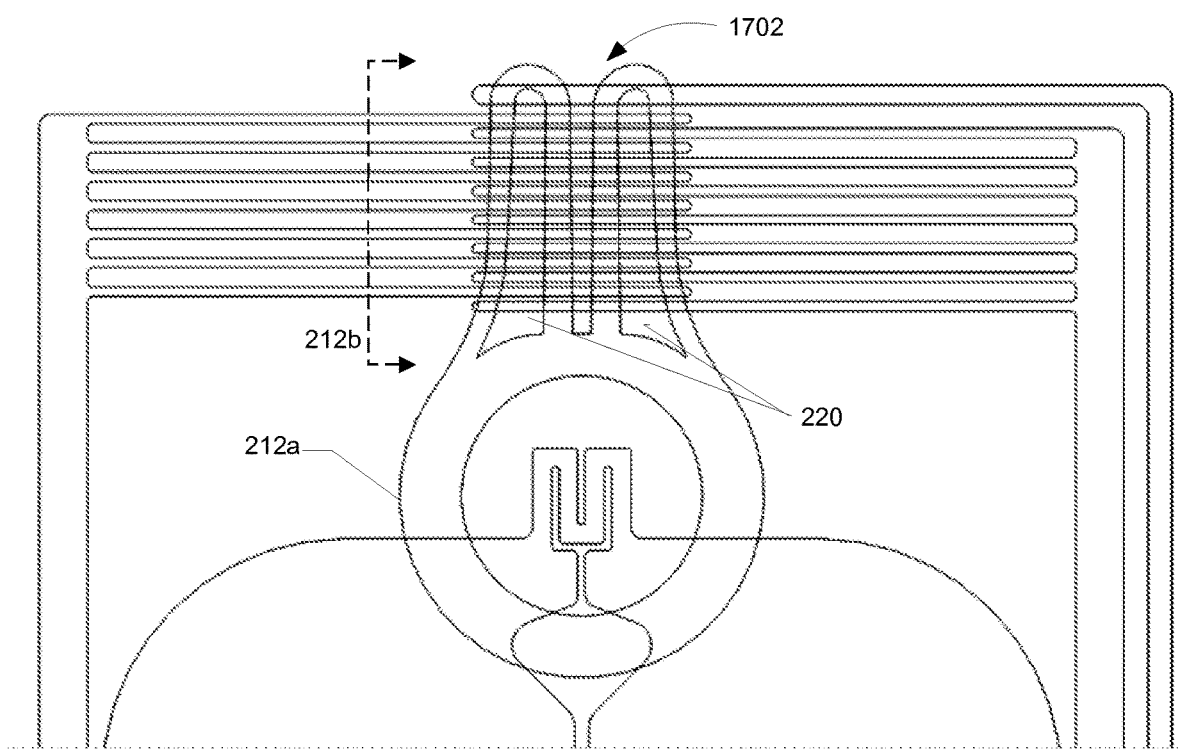

FIG. 17F illustrates an alternative embodiment transdermal sampling and analysis device that may have a long sensing chamber 212b that may be divided into two areas, and long channels 222. In the embodiment shown in FIG. 17F the aspect ratio of channel height to channel width may be less than 20:1. For example, each channel 222 may be approximately 500 µm in height and approximately 30 µm in width. Each of the sensing chamber 212b areas may be formed with tapered outer edges 1710. In addition, each of the sensing chamber 212b areas may contain a singular channel support 220. The singular channel support contained in each of the sensing chamber 212b areas may be configured in a similar shape as the sensing chamber 212b areas in which it may be contained.

Figure 17G:
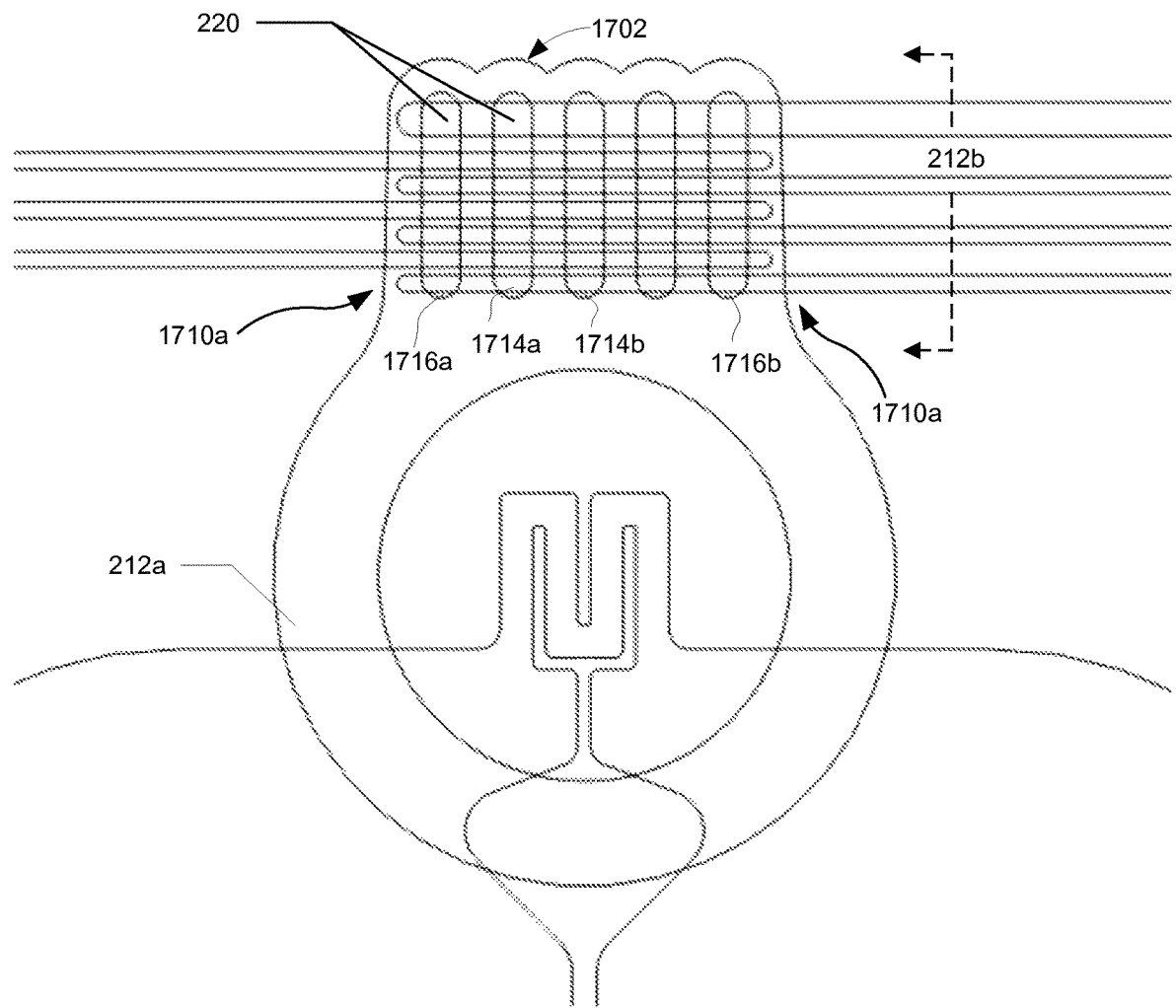

FIG. 17G illustrates an alternative embodiment transdermal sampling and analysis device wherein the aspect ratio of the height of each channel to the width of each channel is less than 10:1. The embodiment illustrated in FIG. 17G may be significantly similar to the embodiment illustrated in FIG. 17D. However, as shown in FIG. 17G, the channel supports 220 may be configured without the taper or bulbous shape at the top of the channel supports 220. In the configuration, the width of the channel support 220 and the channels 222 formed between the channel supports 220 may be constant. In an example, the width of the channels 222 formed between inner channel supports 1708a, 1708b may be about 35 µm. The width of the channels 222 formed between outer channel supports 1716a, 1716b and edges 1710a, 1710b may be about 40 µm. The height of all channels 222 may be about 250 µm. Thus, the aspect ratio of each of the channels 222 in FIG. 17G is less than or equal to 10:1.

Each of the embodiment configurations shown in FIGS. 17A-17G have been observed to provide satisfactory fill rates as well as sensation levels experienced by the subjects. In addition, each of the embodiment configurations shown in FIGS. 17A-17G have been observed to mitigate bubble formation even in the presence of a biologically reactive element applied to the counter and working electrodes. While the fill rates vary among the embodiment configurations, embodiments wherein the edges of the sensing chamber may be tapered and intersect the collection reservoir with a smooth surface may be observed to be the most successful in mitigating the formation of air bubbles.

In some embodiments, various compounds in the biological sample in the sensing chamber 212b and/or collection reservoir 212a may create interference by directly reacting with the mediator of the sensing reagent. For example, when a mediator with ferrocene is applied in the sensing chamber 212b, various reducing species in interstitial fluid may transfer their electrons to the mediator, thereby significantly reducing the effectiveness of the sensing reagent. To address this issue, a barrier layer may be applied over the sensing reagent film so that interaction between the extraneous redox species and the sensing reagent is substantially decreased. Example barriers may include, but are not limited to, I-PEI, bovine serum, poly(carboxybetaine methacrylate) (pCBMA), GOD, etc. The barrier may be a monolayer of a suitable material, and may effectively reduce the undesirably interactions between ISF and glucose, and improve signal to noise ratio.

Despite the benefit of using a barrier layer to solve the issue of interference, when used in the embodiments discussed above with respect to FIGS. 17A-17G, the barrier layer may impede the flow of the biological sample throughout the entirety of the sensing chamber 212b. Consequently, interstitial fluid may remain in the collection reservoir 212a instead of being drawn by capillary force to flow over the counter and working electrodes.

Figure 18A:
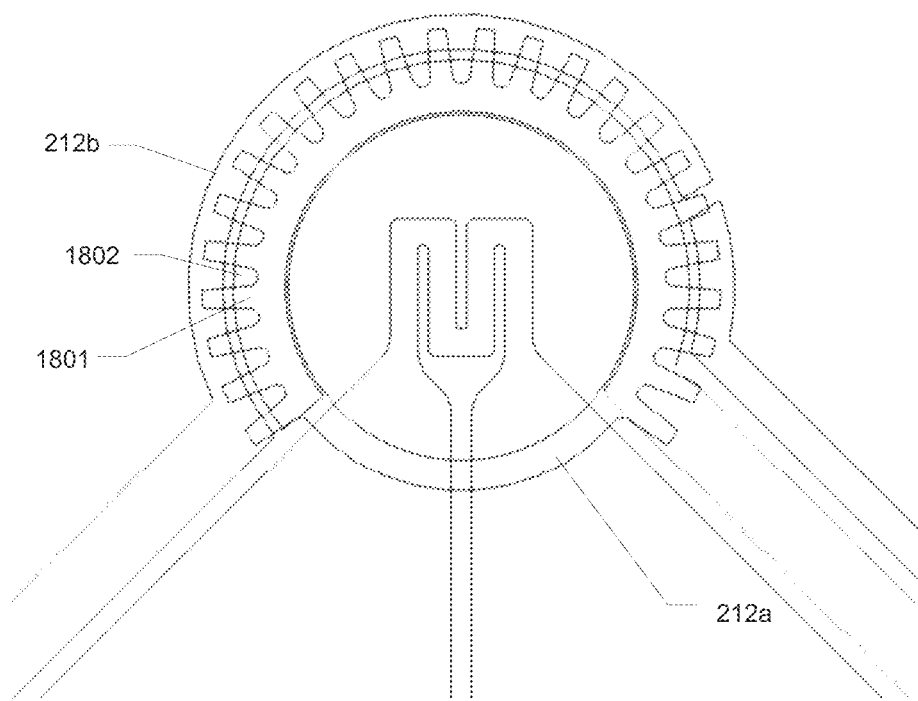
FIG. 18A illustrates a top view of a transdermal sampling and analysis device according to another embodiment.
Figure 18B:
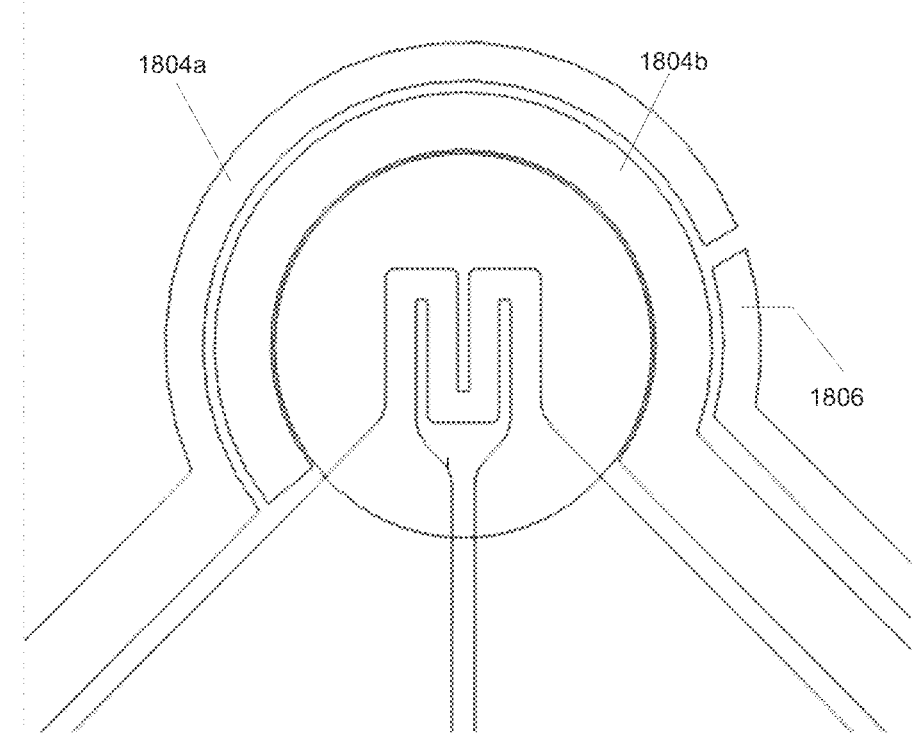
FIG. 18B illustrates a top view of the transdermal sampling and analysis device of FIG. 18A without the sensing channels.

In exemplary embodiments shown in FIGS. 18A-18D, the configuration of the sensing chamber 212b may prevent bubble formation while allowing proper flow of the interstitial fluid even when a barrier is used over the sensing reagent. FIGS. 18A and 18B illustrate an embodiment transdermal sampling and analysis device. In FIG. 18A, the sensing chamber 212b may form a circular shape surrounding the periphery of the collection reservoir 212a. The sensing chamber 212b may contain circular channel supports 1801 which may form circular sensing channels 1802. The circular channel supports 1801 and circular sensing channels 1802 may guide the flow of a biological sample through the circular-shaped sensing chamber 212b. FIG. 18B illustrates a view of the embodiment shown in FIG. 18A without the circular channel supports 1801 and circular sensing channels 1802. Working electrode 1804a, counter electrode 1804b and reference electrode 1806, may be provided in various configurations around the periphery of the collection reservoir 212a such that the sensing chamber 212b directs the flow of interstitial fluid over the entirety of the working and counter electrodes, 1804a, 1804b.

Figure 18C:
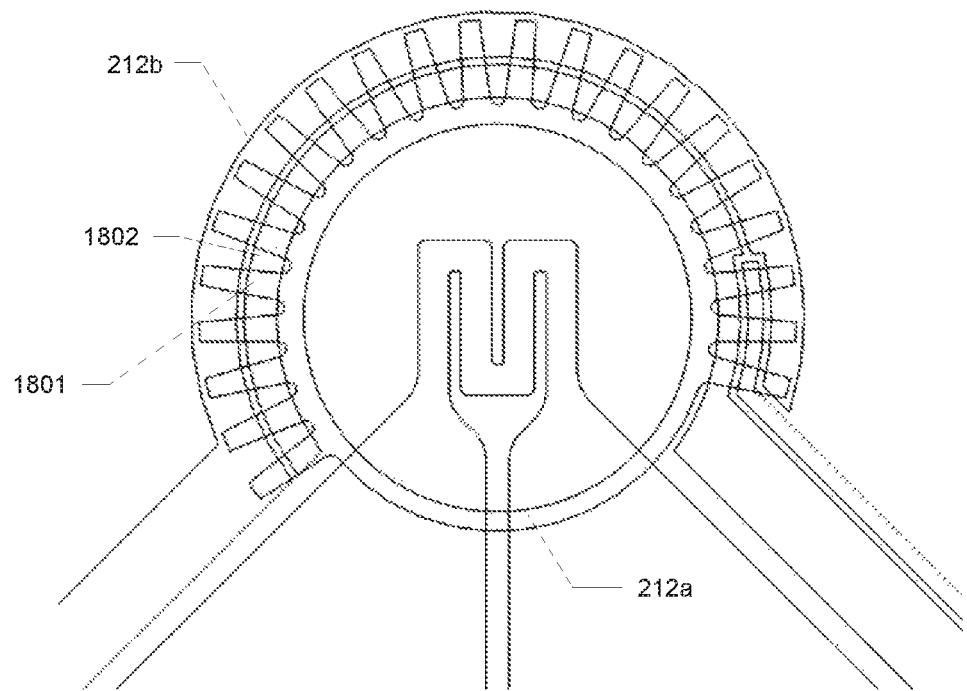
FIG. 18C illustrates a top view of a transdermal sampling and analysis device according to another embodiment.
Figure 18D:
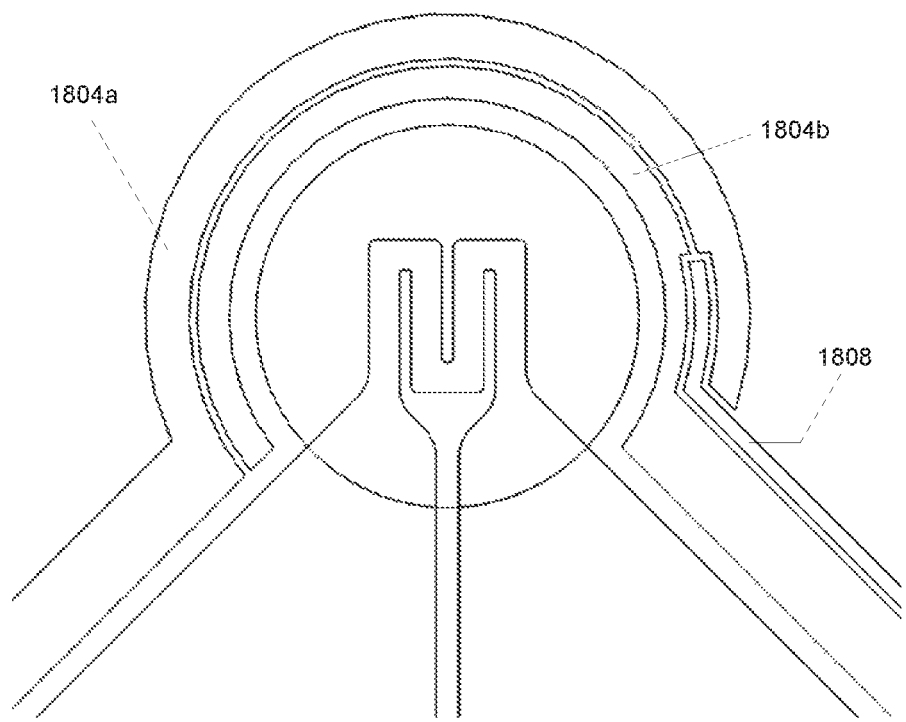
FIG. 18D illustrates a top view of the transdermal sampling and analysis device of FIG. 18C without the sensing channels.

FIGS. 18C and 18D illustrate an alternative embodiment transdermal sampling and analysis device that is substantially the same as the embodiment shown in FIGS. 18A and 18B. However the embodiment illustrated in FIGS. 18C and 18D may implement a reference electrode 1808 in a slightly different configuration as compared to reference electrode 1806 in FIGS. 18A and 18B.

The circular sensing chamber 212b configuration shown in FIGS. 18A-18D provide a sensing chamber 212b with an increased circumference surrounding the collection reservoir 212a. In contrast to the embodiment configurations shown in FIGS. 11A, 11B, 17B-17E and FIG. 17G which may contain six channels 222 that may each be approximately 30 μm wide and 250 μm to 500 μm high, the circular sensing chamber configuration shown in FIGS. 18A-18D may contain, for example, twenty-four circular sensing channels 1802 formed between circular channel supports 1801. Each of the circular sensing channels 1802 may be approximately 80 μm in height, while still retaining a width of approximately 30 μm. Thus, the aspect ratio of height to width of the embodiment circular sensing channels 1801 may be less than 3:1. In a preferred embodiment the aspect ratio of height to width of the embodiment circular sensing channels 1801 may be approximately 1:1. Because the overall width (circumference) of the circular sensing chamber may be increased, the height (radius extending from the center of the collection reservoir 212a) of the circular sensing chamber 212b may be decreased while keeping the overall area of the sensing chamber 212b constant. Thus, the same amount of biological fluid may be directed to cover the counter and working electrodes 1804a, 1804b while requiring the biological fluid to travel a shorter distance from the collection reservoir 212a. In addition, the circular shape of the sensing chamber 212b may allow the biological fluid that is generated by the disruption of the stratum corneum to more evenly disperse radially outward in manner which further mitigates the creation of air bubbles or zones of fluid bridging across channel supports 1801 contained within the sensing chamber 212b. Embodiment transdermal sampling and analysis devices implementing the circular sensing chamber configuration as shown in FIGS. 18A-18D have been observed with satisfactory fill rates and sensation levels as well as the absence of air bubble formation even when biologically reactive elements and barrier layer elements have been applied.

The transdermal sampling and analysis devices 200 of the various embodiments may be manufactured using different methods and materials. Manufacturing methods for an embodiment transdermal sampling and analysis device 200 may be disclosed in the related International Application Number PCT/US2006/023194, filed Jun. 14, 2006, entitled "Flexible Apparatus and Method for Monitoring and Delivery," which claims priority to the International Application Number PCT/US2005/044287, entitled "Apparatus and Method for Continuous Real-Time Trace Bimolecular Sampling, Analysis and Deliver," filed on Dec. 9, 2005, which are attached hereto as Appendices A and B. The manufacturing of an embodiment transdermal sampling and analysis device 200 is also disclosed in the publication entitled "Novel Non-Intrusive Trans-Dermal Remote Wireless Micro-Fluidic Monitoring System Applied to Continuous Glucose and Lactate Assays for Casualty and Combat Readiness Assessment" by John F. Currie, Michael M. Bodo and Frederick J. Pearce, RTO-MP-HFM-109:24-1, Aug. 16, 2004. A copy of the publication is attached hereto as Appendix C. The entire contents of all of the related applications and publication are incorporated by reference herein.

An embodiment device may be manufactured using materials and equipment commonly used in the micro-fabrication and bio-sensing industries. Formation of the conductive material layer on the substrate may be accomplished using any of the various deposition techniques known in the art. For example, thin film deposition (e.g., evaporation) may be used to form a conductive material layer on the substrate.

Figure 19:
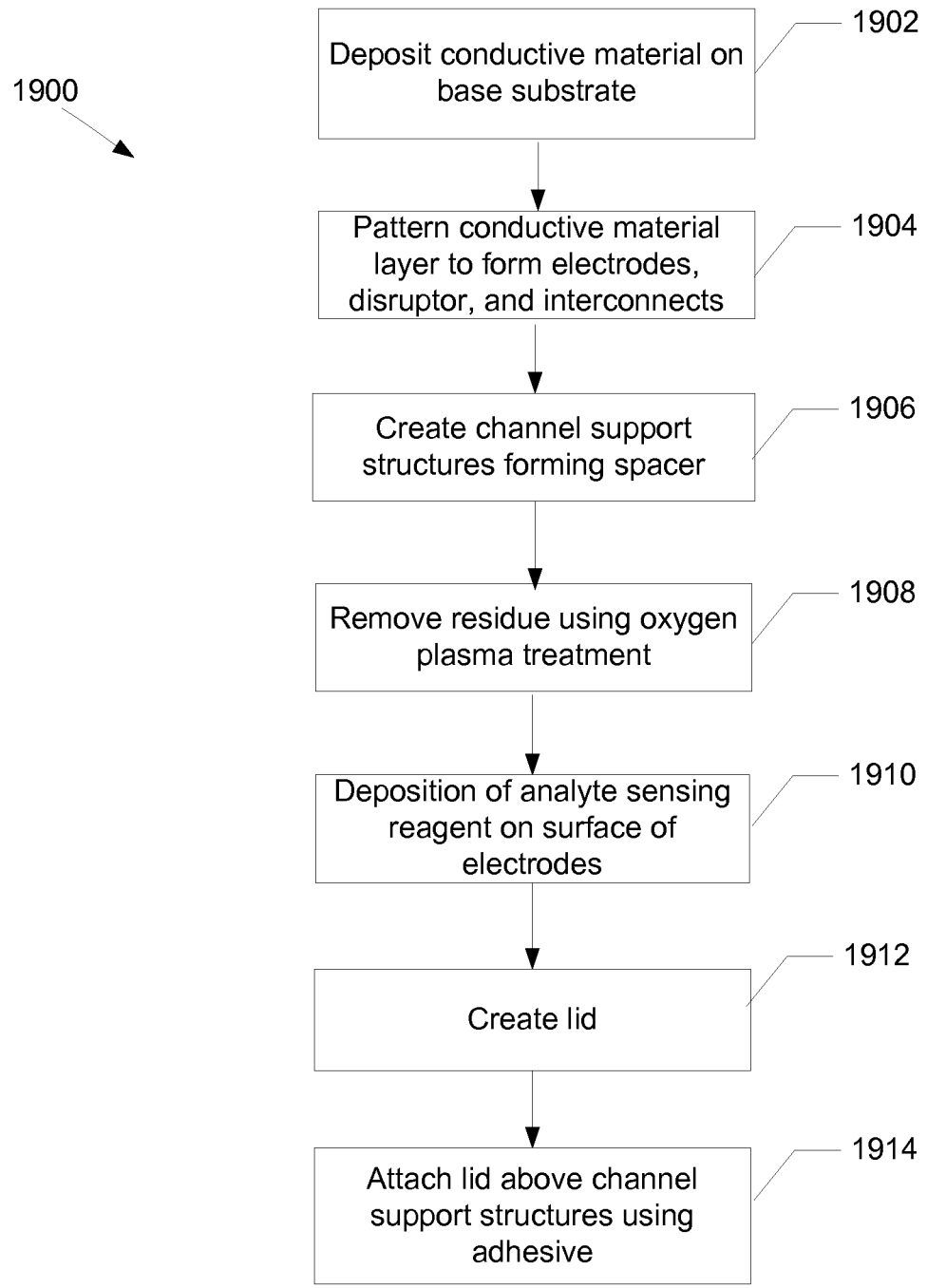
FIG. 19 is a process flow diagram illustrating an embodiment method of making a transdermal sampling and analysis device.

FIG. 19 is a process flow diagram illustrating an example method 1900 for manufacturing a transdermal sampling and analysis device. In step 1902, a conductive material, from which the disruptor, at least two electrodes, and the interconnects may be formed, may be deposited on a base substrate. The substrate layer may be made of a variety of materials such as glass, plastic, metal or silicon. In an embodiment, the substrate may be made of a polyimide such as Kapton™. Kapton™ is a polyimide film developed by DuPont™.

In an embodiment, the conductive material may be gold. In alternative embodiments, the conductive material may be one or more other metals, such as one or more of nichrome, titanium, and tungsten. Deposition of the conductive material layer on the substrate may be accomplished, for example, by evaporating a thin layer of conductive material on the substrate. In other embodiments, deposition of the conductive material may be performed using any of a variety of other techniques known in the art. Such techniques may include, but are not limited to, sputter deposition, vacuum deposition, ion plating, ion beam assisted deposition (IBAD), pulsed laser deposition, etc. In alternative embodiments, the conductive material may be applied by other coating techniques, such as spin coating, electroplating, spraying, etc.

In step 1904, the conductive material layer may be patterned to create the disruptor, at least two electrodes (e.g., a counter electrode and a working electrode), and interconnects of the device. Patterning may be performed according to a basic photolithographic process known in the art, the steps of which may include applying a photoresist, drying, exposing and patterning in the photoresist, developing the photoresist, etching the conductive material (e.g., metal), and stripping the photoresist.

In step 1906, a photo-sensitive polymer may be applied onto the surfaces of the counter and working electrodes. The photo-sensitive polymer may be patterned using photolithographic techniques known the art to create channel support structures forming a spacer. In one embodiment, photolithographic techniques may include steps such as applying a photo-sensitive polymer coating to an underside of the lid, applying a positive resist pattern to the photo-sensitive polymer coating, exposing the photo-sensitive polymer coating to a light source, and using developer solution to remove any photo-sensitive polymer that was exposed to the light source.

The photo-sensitive polymer may be, for example, a material with a low wetting angle (e.g., less than 40 degrees) in order to promote capillary action by the channels that are formed between the channel support structures. In an embodiment, the photo-sensitive polymer may include a ceramic.

In step 1908, any residue of the photo-sensitive polymer remaining on electrodes between the channel support structures may be removed by oxygen plasma treatment well known in the art. In step 1910, an analyte sensing layer, for example may be selectively deposited on the conductive material layer in conjunction with an electron mediator. In an embodiment, the analyte sensing layer may be a film disposed on the surface of the sensing electrode(s), forming a solid state mediated sensor. In an embodiment, the film may be formed by a polymer (e.g., linear poly(ethyleneimine)), a mediator (e.g., ferrocene) covalently bonded to the polymer, and a biologically reactive element such as an enzyme (e.g., (e.g., glucose oxidase, glucose dehydrogenase, etc.) that is immobilized by the polymer with covalently-bonded mediator.

In step 1912, a lid for the device may be created by applying a thin layer of adhesive to a polymeric substrate such as polyester, polycarbonate, acetate, or the like, then cutting to size and shape by IR or excimer laser as well known in the art. The lid may be positioned and attached to the device on top of the spacer (i.e., above the channel support structures).

While method 1900 may be an effective way to manufacture a transdermal sampling and analysis device, it has also been observed that the analyte sensing reagent deposited in step 1910 may tend to form a non-uniform layer over the counter and working electrodes due to the presence of channel support structures in the spacer. For example, using method 1900 to create a device with a desired glucose oxidase layer on the electrodes of around 1 µm, the actual resulting layer may measure around 15 µm toward the edges and around 0.1 µm near the center of the reservoir. Since interstitial fluid collected for analysis may be blocked from channels by an excess of glucose oxidase toward the edges, overall performance of the device may be significantly decreased due to this non-uniform distribution.

As discussed above, and as shown in FIGS. 21A-21C (discussed in further detail below), an alternative process for manufacturing a transdermal sampling and analysis device may involve constructing the reservoir without attached channel supports (and therefore without channels), and instead forming channel support structures of the spacer as part of the lid (i.e., attached to a first side of the lid). Thus, once the lid is attached onto the transdermal sampling and analysis device, the channels supports of the lid may create channels in the reservoir. This alternative embodiment may substantially decrease or even prevent uneven distribution of the analyte sensing reagent due to clogging of the channels in the reservoir. Consequently a more uniform layer of analyte sensing reagent may be formed.

Figure 20A:
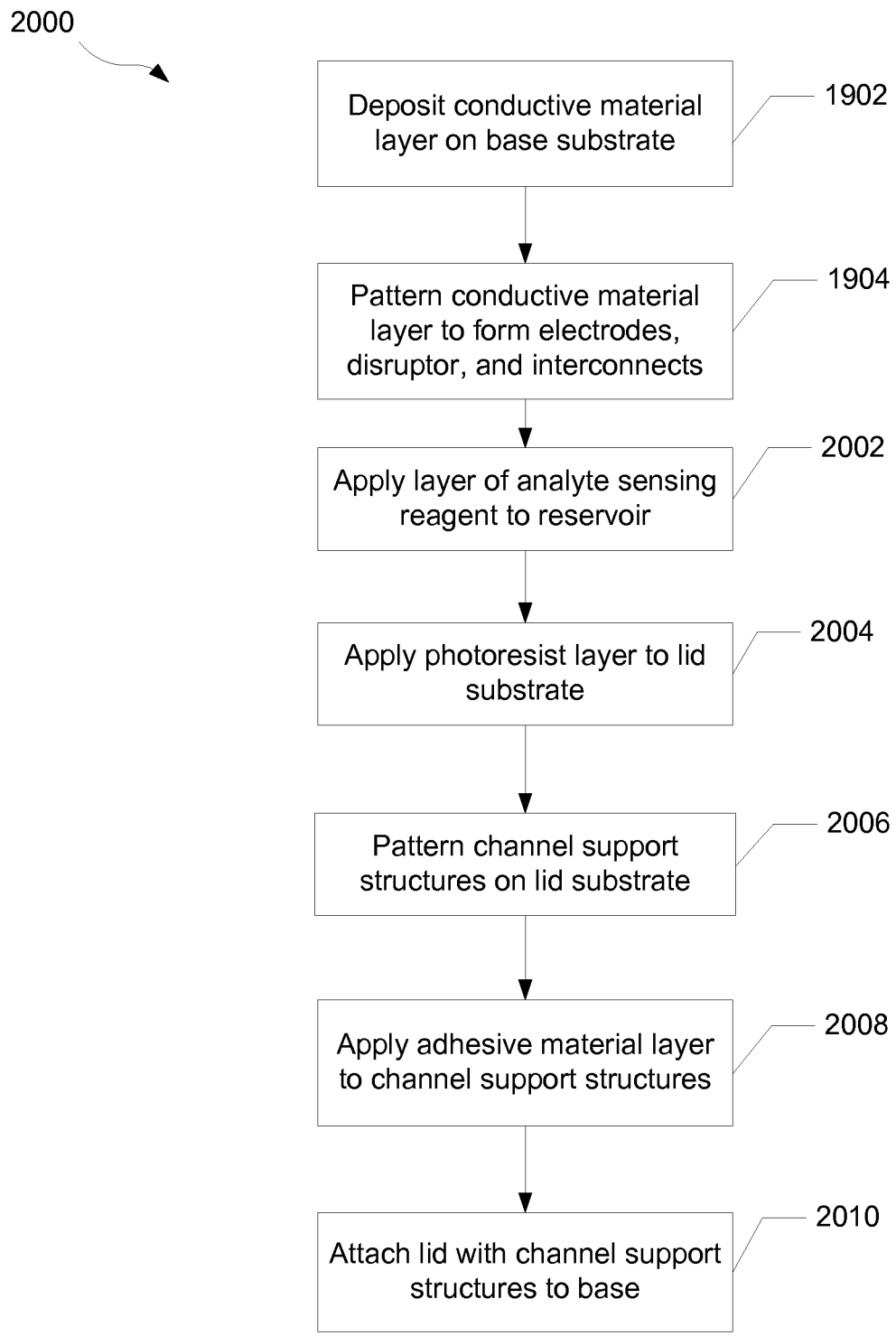
FIGS. 20A and 20B are process flow diagrams illustrating another embodiment method of making a transdermal sampling and analysis device.

FIG. 20A is a process flow diagram illustrating an alternative method 2000 for manufacturing a transdermal sampling and analysis device. In the alternative embodiment method 2000, steps 1902 and 1904 of method 1900 may be performed in the same manner as discussed above. In step 2002, an analyte sensing layer (i.e., a layer of the analyte sensing reagent) may be applied to the surface of the reservoir (e.g., by deposition, coating, etc.).

In steps 2004-2008, a lid for the device may be created with a spacer layer of integrated channel support structures. Specifically, in step 2004, a photoresist coating material may applied to the surface of the lid substrate, and in step 2006 the photoresist coating material may be patterned to form the channel support structures In step 2008, an adhesive material layer may be applied to the top surfaces of the channel support structures. The formation of the adhesive layer is described in further detail below with respect to FIG. 20B. In this manner, channels may be created over the counter and working electrodes and the analyte sensing reagent in the reservoir once the lid with the channel support structures is attached to the base, step 2010.

While FIG. 20A illustrates the lid formation steps (steps 2004-2008) as occurring after the conductive material layer is patterned (step 1904) and after the analyte sensing reagent is applied to the reservoir (step 2002), in alternative embodiments the lid may be formed with the channel support structures (steps 2004-2008) at any time before the lid is attached on the device to form channels in the reservoir (step 2010). Thus, in some embodiments, a supply of lids with integrated channel support structures may be pre-formed. In other embodiments, the lid with integrated channel support structures may be formed in parallel with some or all of steps 1902-2002 of method 2000. An adhesive layer, formed by applying a layer of adhesive material in step 2008, may provide a way of attaching the spacer on the lid to the base. In an embodiment, such attachment may require selectively applying a layer of an adhesive material to the tops of the channel support structures, preventing adhesive material from getting in the channels between the support structures. Therefore, selection of an appropriate adhesive material may be important for proper operation of the device.

Figure 20B:
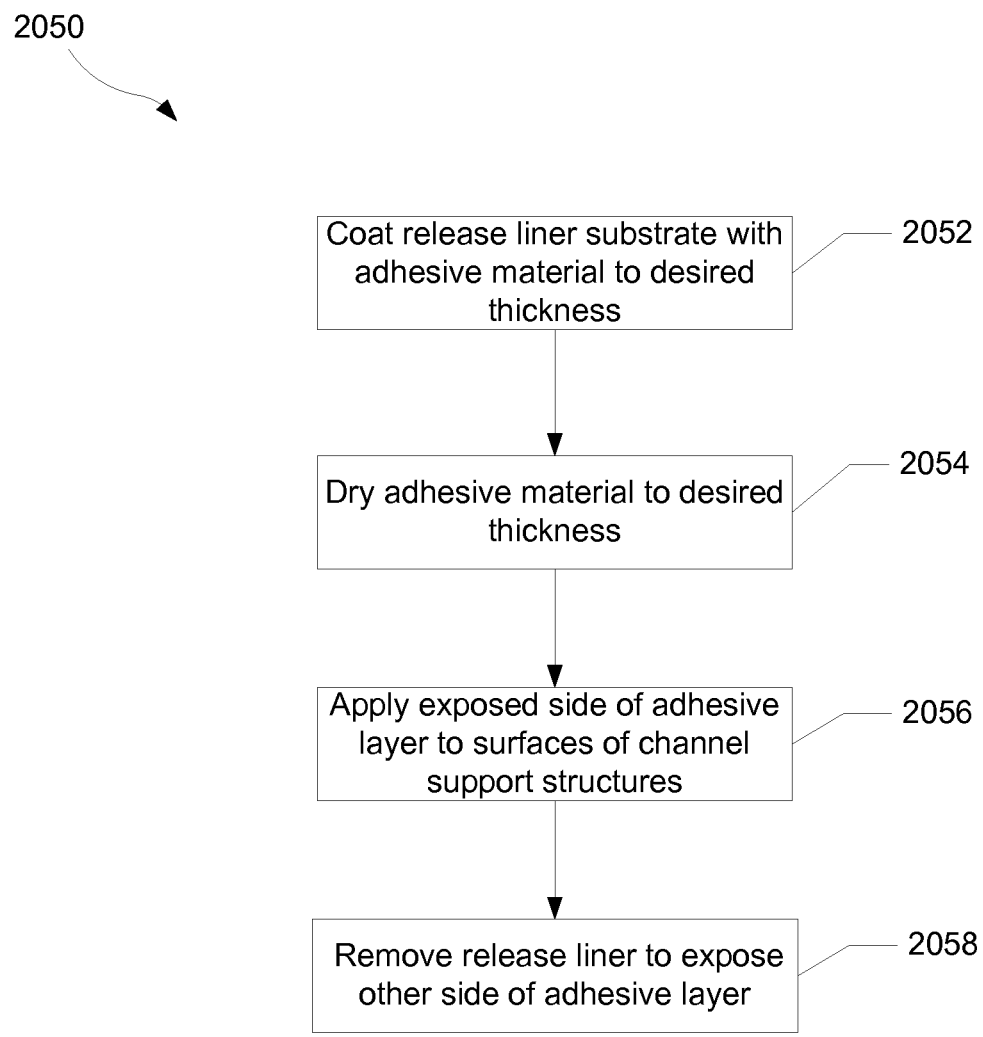

FIG. 20B is a process flow diagram illustrating a method of applying the adhesive material layer in step 2008 of FIG. 20A according to an embodiment. In method 2050, a release liner substrate may be coated with an adhesive material to a desired thickness, step 2052. In step 2054, the adhesive material may be applied as a liquid, and allowed to dry on the release liner substrate to a desired thickness. In step 2056, the exposed side of the adhesive layer may be applied to the surfaces of the channel support structures. In step 2058, the release liner may be removed to expose the opposite side of the adhesive layer, which may adhere to the base upon attaching the lid to the base to form the device. Notably, the adhesive material may be selected such that the adhesive forces between the material and the channel support structures is stronger than the adhesive forces between the material and the release liner substrate. This may ensure that the release liner is removable from the adhesive layer without pulling it off of the channel support structures. However, the adhesive material selected should also have properties such that the adhesive forces between the material and the release liner substrate are stronger than the cohesive forces of molecules of the adhesive material itself. This may ensure that, in areas between the channel support structures (i.e., in the channels), adhesive material will remain on the release liner and will not adhere to the space between the channels formed between the channel support structures.

Figure 21A:
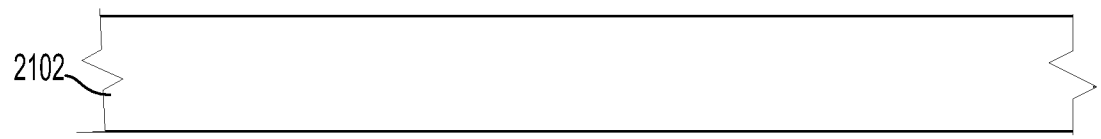
FIGS. 21A-21C illustrate cross-sectional views of a transdermal sampling and analysis device in stages of manufacture according to the process in FIG. 20.
Figure 21B:
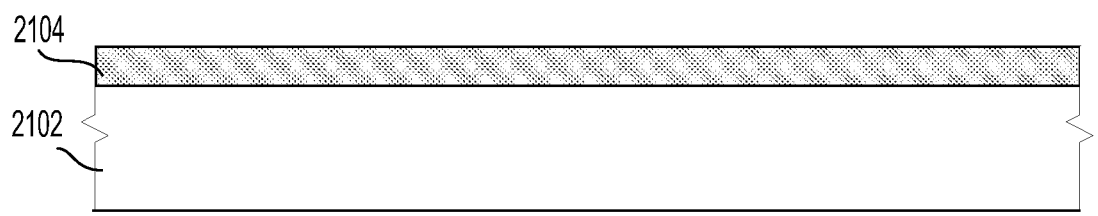
Figure 21C:
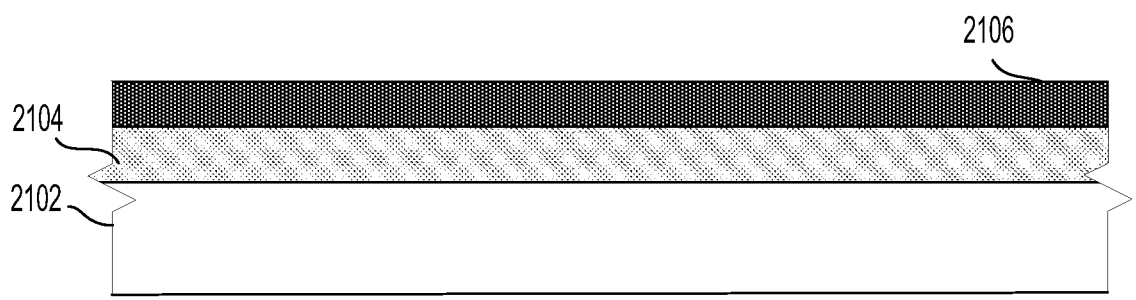

Example structures that may be formed in steps 1902-2002 of method 2000 are further shown by the progression illustrated in FIGS. 21A-21C. FIG. 21A illustrates a clean base substrate layer 2102. FIG. 21B illustrates the substrate layer 2102 with a conductive material layer 2104, such as a thin metal layer, deposited on the substrate layer 2102, corresponding to step 1902 of method 2000. FIG. 21C illustrates the substrate layer 2102, with the conductive material layer 2104, and a layer 2106 of an analyte sampling reagent that has been deposited on the conductive material layer 2104, corresponding to step 2002 of method 2000. In various embodiments, the layer 2106 may have an electron mediator in addition to the analyte sampling reagent, and may be further covered with an optional anti-interferent barrier layer (not shown).

Figure 22:
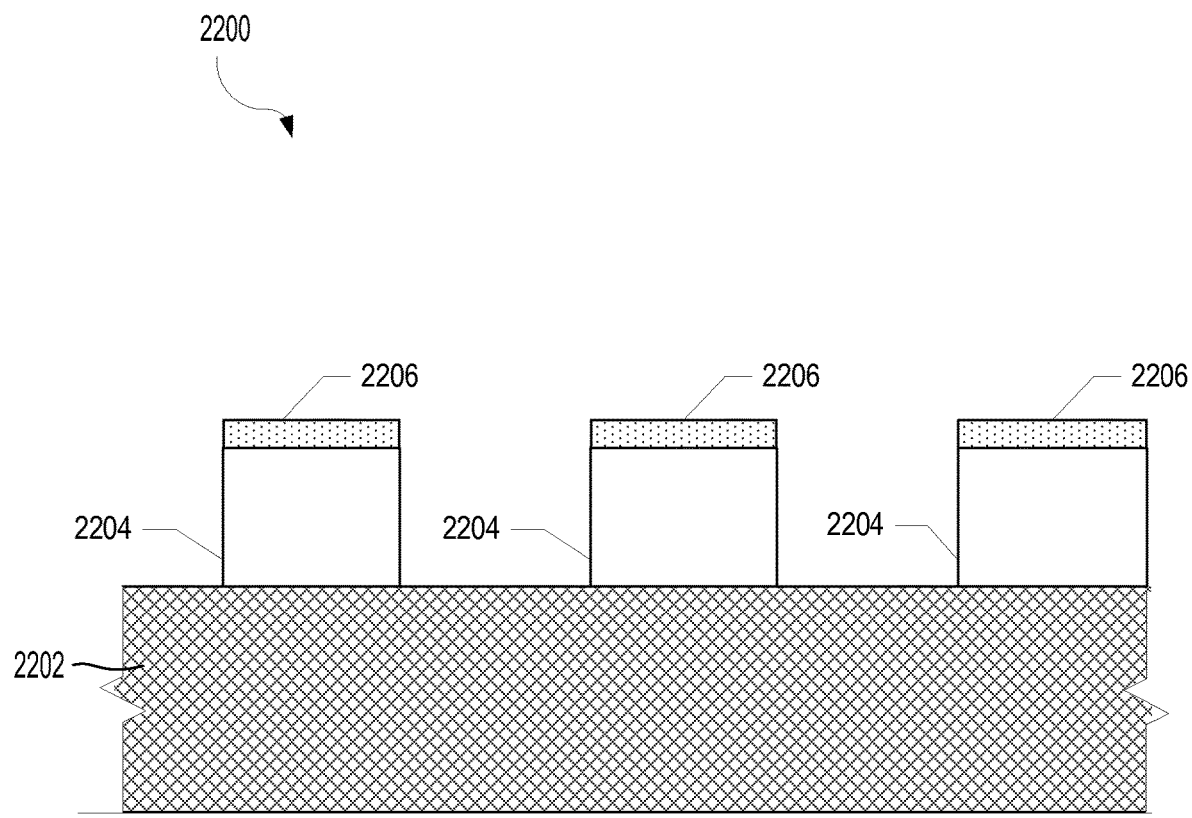
FIG. 22 illustrates a cross-sectional view of a lid structure for a transdermal sampling and analysis device shown in FIGS. 21A-21C.
Figure 23:
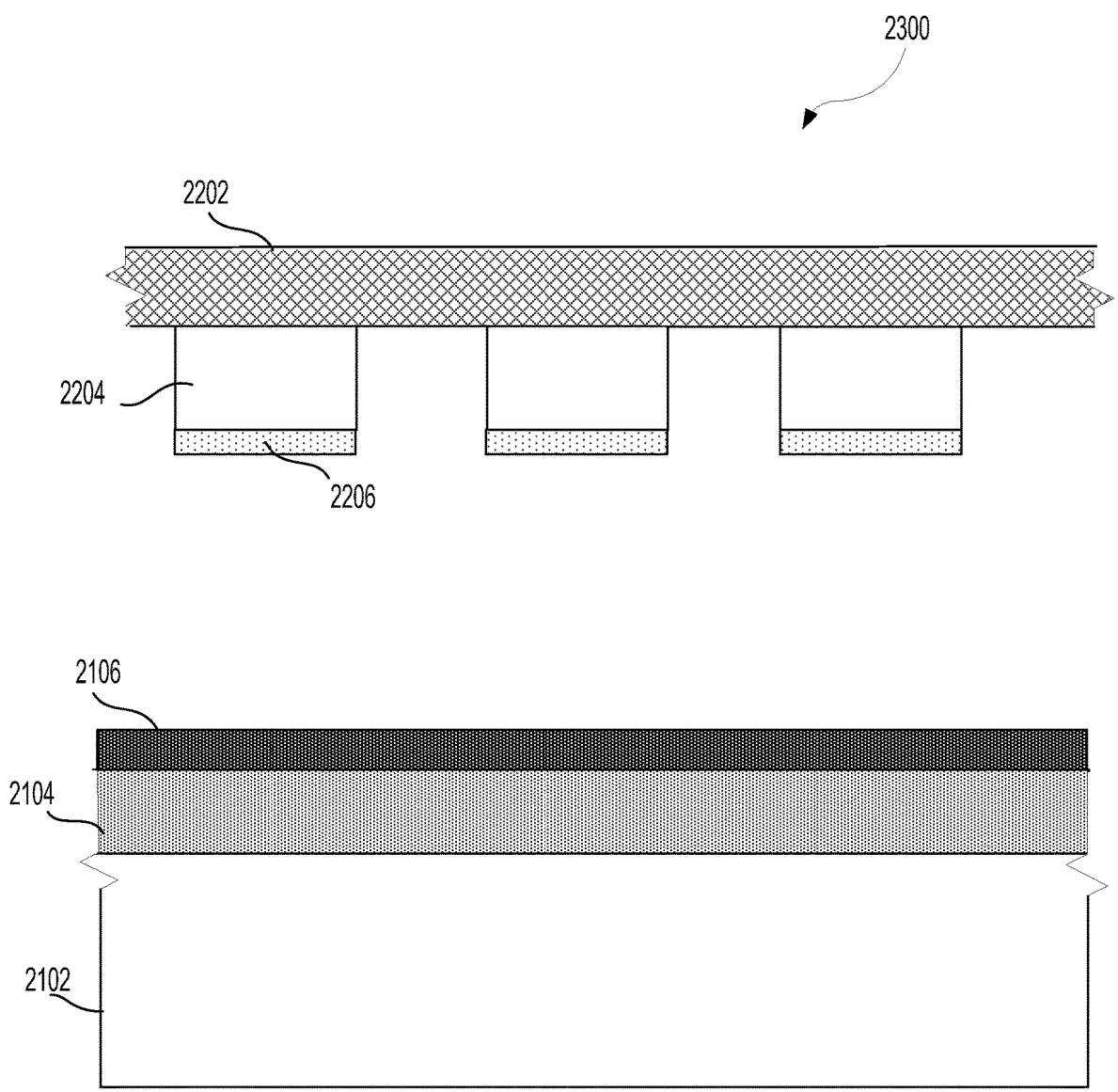
FIG. 23 illustrates a cross-sectional view of the relationship between the lid structure shown in FIG. 22 and the transdermal sampling and analysis device shown in FIGS. 21A-21C.

FIG. 22 illustrates an example lid structure that may be formed as a result of steps 2004-2008 of method 2000. Lid 2200 may include a lid substrate material 2202, on which a photoresist coating material may be applied, corresponding to step 2004 of method 2000. The photoresist coating material may be patterned to create channel support structures 2204 in a spacer layer, corresponding to step 2006 of method 2000. An adhesive material layer 2206 may be applied to only the top surface of the spacer layer (i.e., the tops of the channel support structures 2204) corresponding to step 2008 of method 2000. FIG. 23 illustrates components that, when joined together, form a device 2300. Device 2300 may have a base with the layers shown in FIG. 21C (i.e., base substrate 2102, conductive material layer 2104, and analyte sensing layer 2106), and may have a lid 2200 shown in FIG. 22. In an embodiment, the device 2300 may be manufactured according to method 2000 shown in FIG. 20A. Once the channel support structures 2204 on the underside of the lid attach to the base of the on the device 2300, the channels support structures 2204 may create channels in the reservoir.

As discussed with respect to FIGS. 20A, 21A-21C, 22 and 23, forming a spacer with channel support structures on the lid in method 2000 may provide an effective way to avoid channel blockage due to non-uniform distribution of the analyte sensing reagent in the reservoir (i.e., excess collection toward edges). However, the spacer may be relatively thick (e.g., around 30 µm) compared to the lid, which may be optimally thin to facilitate disruption. Since photoresist material, from which the channel support structures may be patterned, is typically coated on as a liquid and later dried, forming the spacer may cause internal stress to the thin lid structure (i.e., causing the lid to bend).

Figure 24:
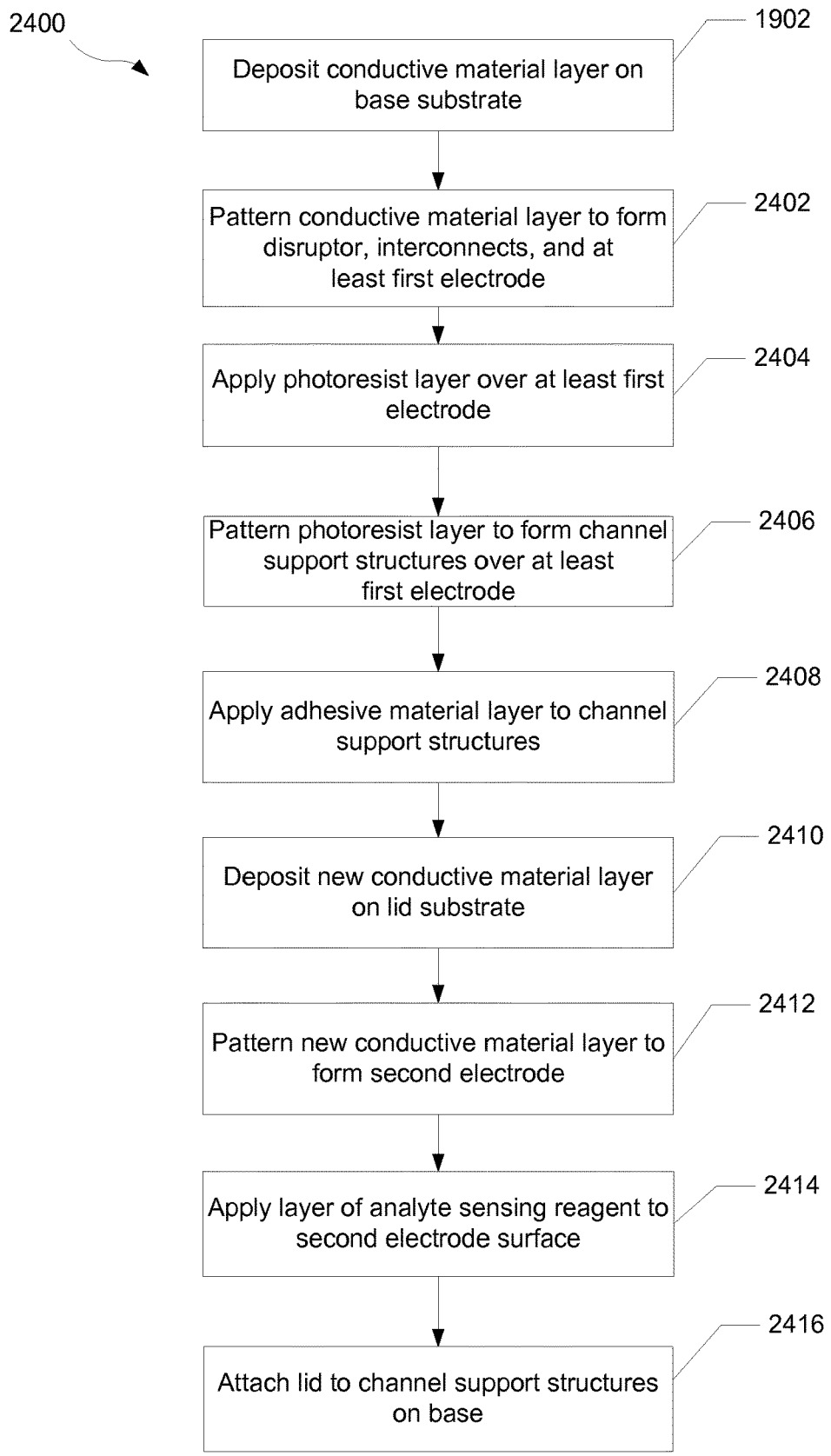
FIG. 24 illustrates an embodiment method of manufacturing a transdermal sampling and analysis device according to an alternative embodiment.

FIG. 24 is a process flow diagram illustrating an example method for manufacturing a transdermal sampling and analysis device according to an alternative embodiment. In particular, method 2400 may create a configuration in which channel support structures are formed on the base of the device, yet still ensuring uniform distribution of the analyte sensing reagent in the reservoir. Method 2400 may begin with the same first step as in step 1902 of method 1900. In step 2402, a first layer of conductive material may be patterned to form the disruptor, interconnects, and at least a first electrode (e.g., the counter electrode, or counter and reference electrodes). In step 2404, a photoresist layer may be applied to the base substrate over the at least first electrode, which may be patterned to form channel support structures, step 2406. In step 2408, a layer of adhesive material may be applied to only the top surfaces of the spacer channel support structures. In an embodiment, the layer of adhesive material may be applied using a technique similar to method 2050, discussed above with respect to FIG. 20B.

In step 2410, a second layer of conductive material may be deposited on a lid substrate. In step 2412, the second layer of conductive material may be patterned to form a second electrode (e.g., the working electrode) on the lid substrate. In step 2414, a layer of analyte sensing reagent may be applied to the second electrode. In step 2416, the lid may be positioned on the device, attaching to the channel support structures on the base.

Separating the counter and working electrodes may enable the analyte sensing reagent to be applied to the lid surface in a thin, uniform coating. Additionally, separating the electrodes by forming one electrode on the lid may allow for configurations that produce stronger, and therefore more a more accurate and reliable electrodes. In one example, the additional space provided by separation may allow formation of larger electrodes. In another example, since the electrodes are not on the same plane, a larger exposure area over which the biological sample may flow may be available for each electrode.

Figure 25:
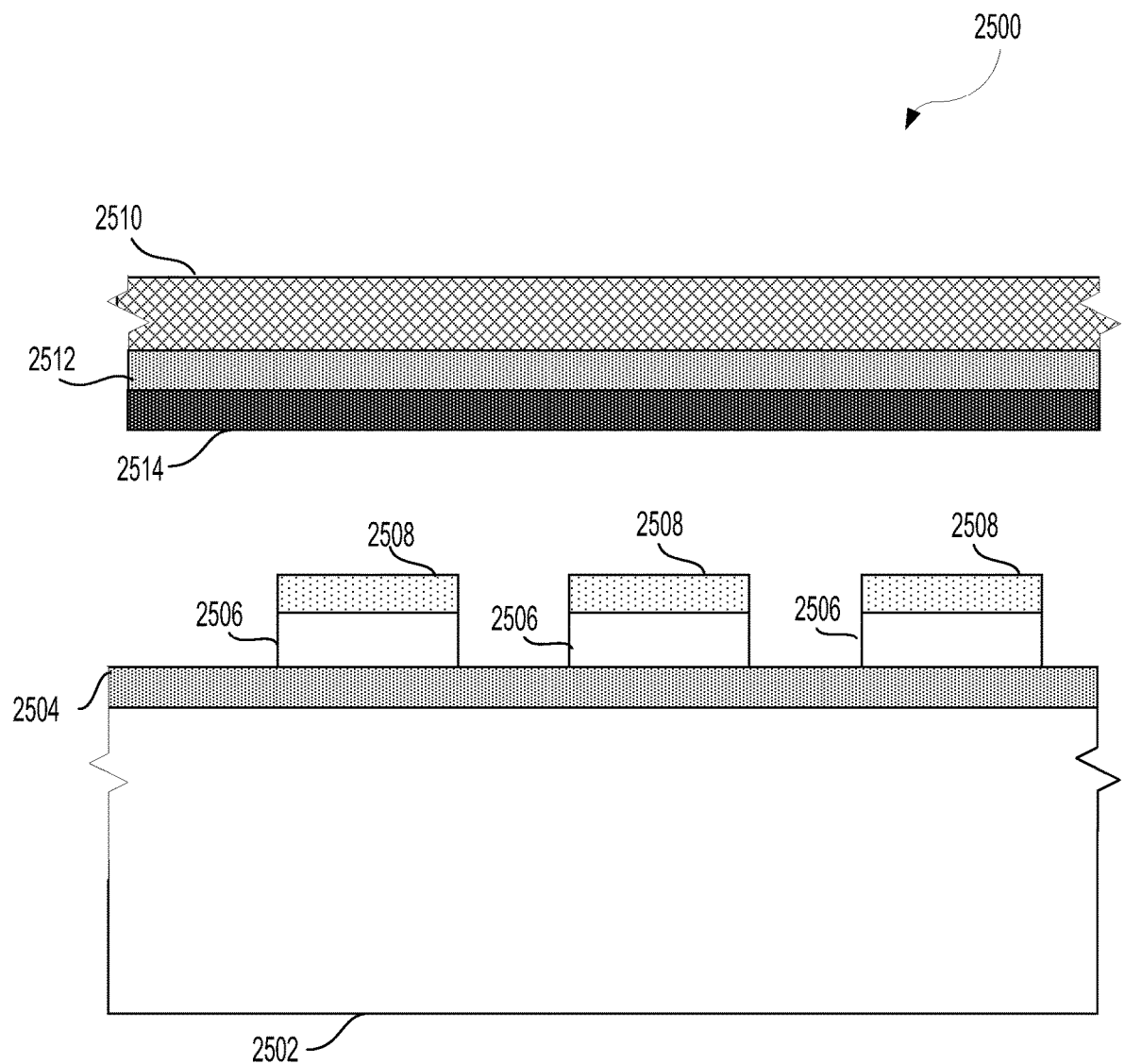
FIG. 25 illustrates a cross-sectional view of a transdermal sampling and analysis device and a lid structure manufactured according to an embodiment method of FIG. 24.

FIG. 25 illustrates example components that may be formed as a result of method 2400 and that, when joined together, create a device 2500. Device 2500 may include a base substrate 2502 and a first conductive material layer that is patterned to form components including at least a first electrode 2504, corresponding to step 2402. Device 2500 may also have a photoresist material applied to the base substrate 2502, corresponding to step 2404, which may be patterned to form channel support structures 2506, corresponding to step 2406. An adhesive material 2508 may be selectively applied to the top surfaces of channel support structures 2506, corresponding to step 2408. In an embodiment, the adhesive material may be applied using method 2050 discussed above with respect to FIG. 20B.

In the lid structure, a lid substrate 2510 may have a second conductive material layer, corresponding to step 2410, which may be patterned to form at least a second electrode 2512, corresponding to step 2412. A layer of the analyte sensing reagent 2514 may be applied to the at least second electrode 2512, corresponding to step 2414.

As discussed with respect to FIGS. 24 and 25, forming a first electrode (e.g., counter electrode) and a spacer layer with channel support structures on the base of the device, and forming a second electrode (e.g., working electrode) on the lid of the device may enable a thin, uniform coating of the analyte sensing reagent to be applied to the reservoir, thereby avoiding buildup from non-uniform distribution in the channels, and may avoid causing internal stress (and therefore bend) to the relatively thin lid structure. However, another consideration that arises as a result of separating the counter and working electrodes onto different planes is the amount of area of each electrode that is exposed, particularly the electrode on the lid. In the embodiment illustrated in FIG. 25, for example, by forming channel support structures 2506 of a spacer layer over the first (i.e., counter) electrode 2504 on the base of the device, the portion of the second (i.e., working) electrode 2512 that is exposed to the channel is defined and limited by the channel support structures 2506 of the spacer layer. However, similar to the first (i.e., counter) electrode 2504, the surface area of the second (i.e., working) electrode 2512 in device 2500 may be limited by the channel support structures 2506. That is, by applying the adhesive material 2508 to the top surfaces of the channel support structures 2506, once the lid structure is set in place, a portion of the second electrode 2512 that is exposed to the channel may be defined and limited by the channel support structures 2506 of the spacer layer.

Figure 26:
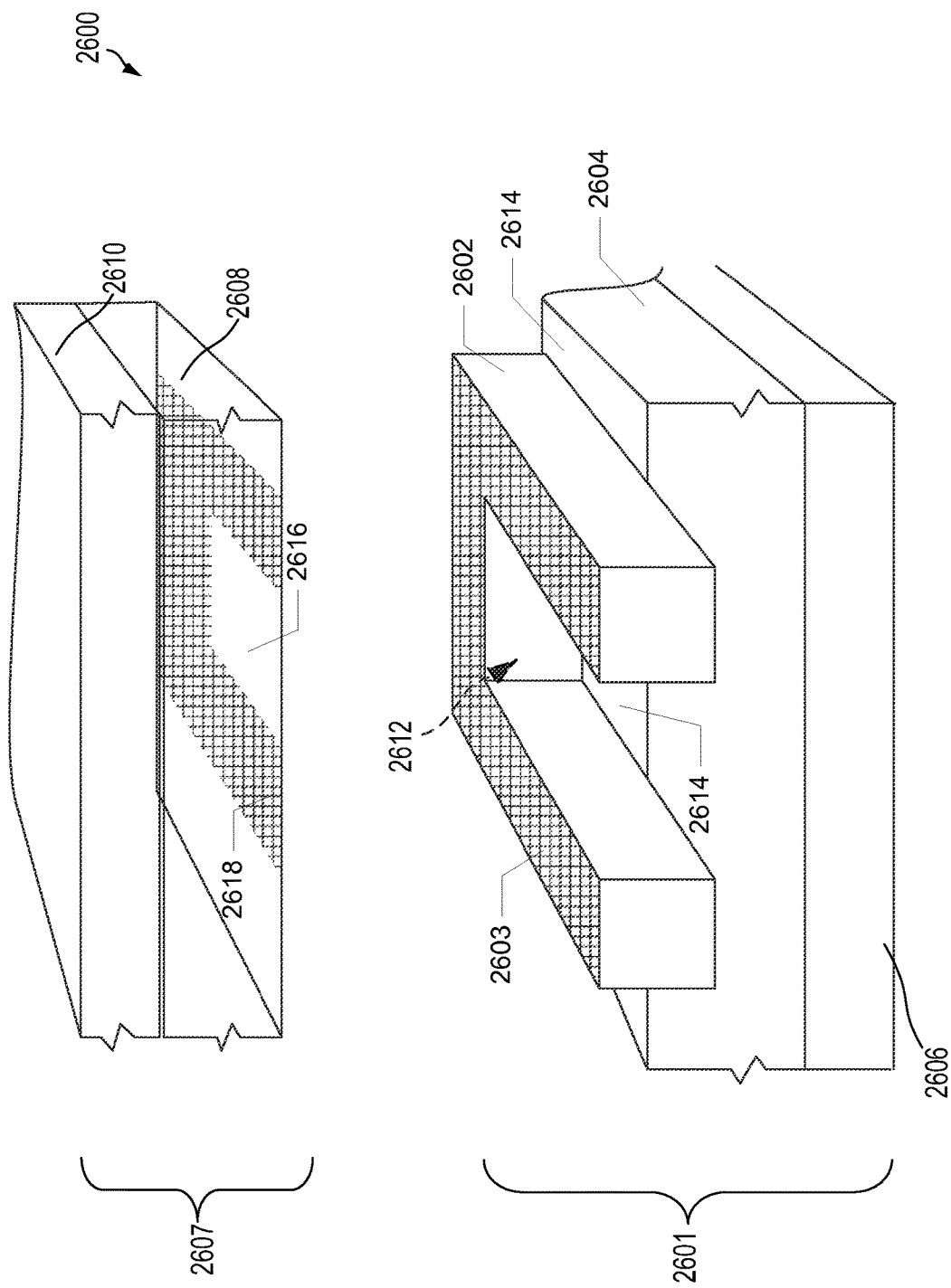
FIG. 26 illustrates a perspective view of a portion of a transdermal sampling and analysis device shown in FIG. 25.

This effect of the spacer layer channel support structures on the working electrode of the device 2500 configuration is further illustrated in FIG. 26. A device 2600 (not drawn to scale) may be formed using techniques similar to those discussed above with respect to FIGS. 24 and 25. Representative components of the device 2600 may include a base structure 2601 that includes a spacer layer of channel support structures 2602 formed over a counter electrode 2604, which are formed over a base substrate 2606. An adhesive (not shown) may be applied to the top surface 2603 of the channel support structures 2602. A lid structure 2607 of the device 2600 may have a working electrode 2608 patterned onto a lid substrate 2610. A layer of analyte sensing reagent (not shown) may have been applied to the surface of the working electrode 2608. The base structure and lid structure shown in device 2600 illustrate representative cross-section segments of a larger, three dimensional device 2600, and are not meant to limit the device 2600 based on size or shape. Further, while the base structure 2601 is shown with two spacer layer channel support structures 2602, they are representative of any of a plurality of sets of channel support structures that may be formed across a larger base structure.

As the lid structure 2607 is brought down into position over the channel support structures 2602, the adhesive on the channel support structures 2602 may secure the lid structure 2607 by contacting the working electrode 2608. In this manner, channels 2612 may be formed between exposed areas 2614 of the counter electrode 2604 and exposed areas 2616 of the working electrode 2608. However, device 2600 shows that such exposed areas on both electrodes are defined by the channel support structures 2602. That is, the direct contact by the top surface 2603 of the spacer layer channel support structures 2602 may "block" a corresponding contact area 2618 of the surface of the working electrode 2608. Moreover, if any of the adhesive material used to secure the working electrode 2608 to the channel support structures 2602 in device 2600 is pushed out (e.g., extruded) once the lid 2607 is secured in place, additional surface regions of the working electrode 2608 may be effectively blocked from coming into contact with the fluid sample as well.

Therefore, in an alternative embodiment, an additional spacer layer may be applied atop the channel forming spacer layer (i.e., channel support structures). In the various embodiments, the second spacer layer may be recessed back from the channel support structures in order to provide lift space between the channel support structures and a substantial portion of the working electrode surface.

While not limited to particular dimensions, in some embodiments the second spacer layer may be approximately the same thickness as the channel forming spacer layer. In an embodiment, the total thickness of the channel forming spacer layer and second spacer layer may be approximately the same as that of the single channel forming spacer layer, such as that of channel support structures 2506, 2602 in FIGS. 25 and 26 respectively. In this manner, the depth of the sensing channels (i.e., vertical space between the counter and working electrodes) may remain the same to avoid requiring a greater amount of fluid to fill.

Figure 27:
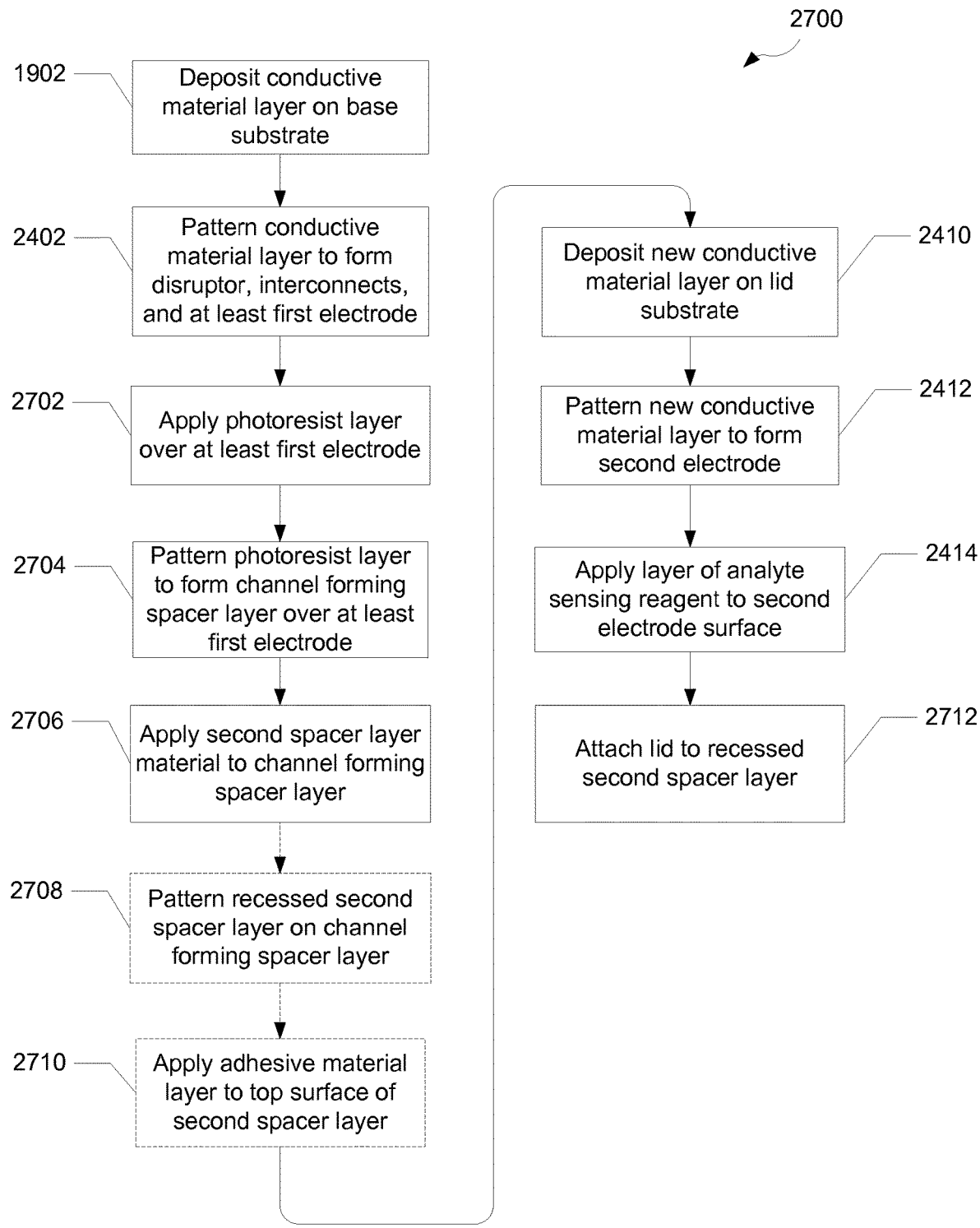
FIG. 27 illustrates an embodiment method of manufacturing a transdermal sampling and analysis device according to an alternative embodiment.

FIG. 27 is a process flow diagram illustrating an example method for manufacturing a transdermal sampling and analysis device according to this alternative embodiment. In particular, method 2700 may create a configuration in which a channel forming spacer layer is formed on the base of the device, over which a second, recessed spacer layer is formed to prevent the channel supports from directly contacting (and blocking) portions of the working electrode. Method 2700 may begin with the same first steps as in steps 1902 and 2402 of method 2400. In step 2702, a photoresist layer may be applied to the base substrate over the at least first electrode (e.g., the counter electrode). In various embodiments, the photoresist layer may be around half of the thickness of the photoresist layer applied in step 2402 of method 2400. In step 2704, the photoresist layer may be patterned to form channel support structures of a channel forming spacer layer. In step 2706, a second spacer layer material may be applied over the channel forming spacer layer. In various embodiments, the second spacer layer material may be approximately the same thickness as that of the photoresist layer applied to the base substrate in step 2702. In one embodiment, the second spacer layer material may be a double sided adhesive that has been pre-cut to be recessed from the channel support structures, thereby removing the need to pattern the material and to apply a separate adhesive layer. Alternatively, the second spacer layer material may be another photoresist layer, similar to the photoresist layer applied over the counter electrode in step 2702. In this case, the photoresist layer may be patterned in optional step 2708 to form the second spacer layer that is recessed from the channel forming spacer layer, and a layer of adhesive material may be applied to the top surface of the second spacer layer in optional step 2710. In an embodiment, the layer of adhesive material may be applied using a technique similar to method 2050, discussed above with respect to FIG. 20B. Formation of the lid structure in method 2700 may involve the same steps 2410-2414 as in method 2400, discussed above with respect to FIG. 24. In step 2712, the lid may be positioned on the device, attaching to the recessed second spacer layer that has been formed over the channel forming spacer layer.

Figure 28A:
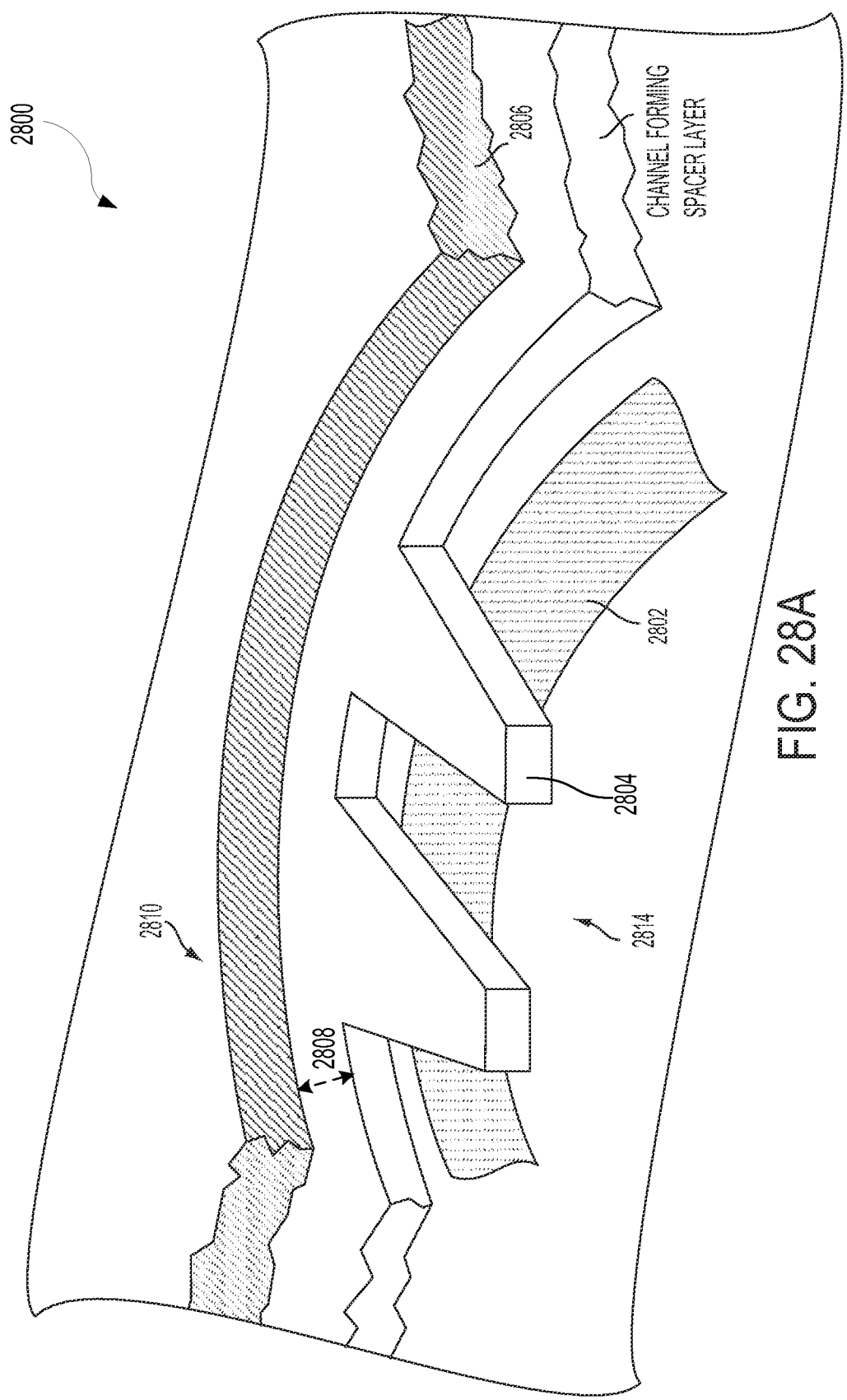
FIG. 28A illustrates a cross-sectional view of a base structure for a transdermal sampling and analysis device manufactured according to an embodiment method of FIG. 27.
Figure 28B:
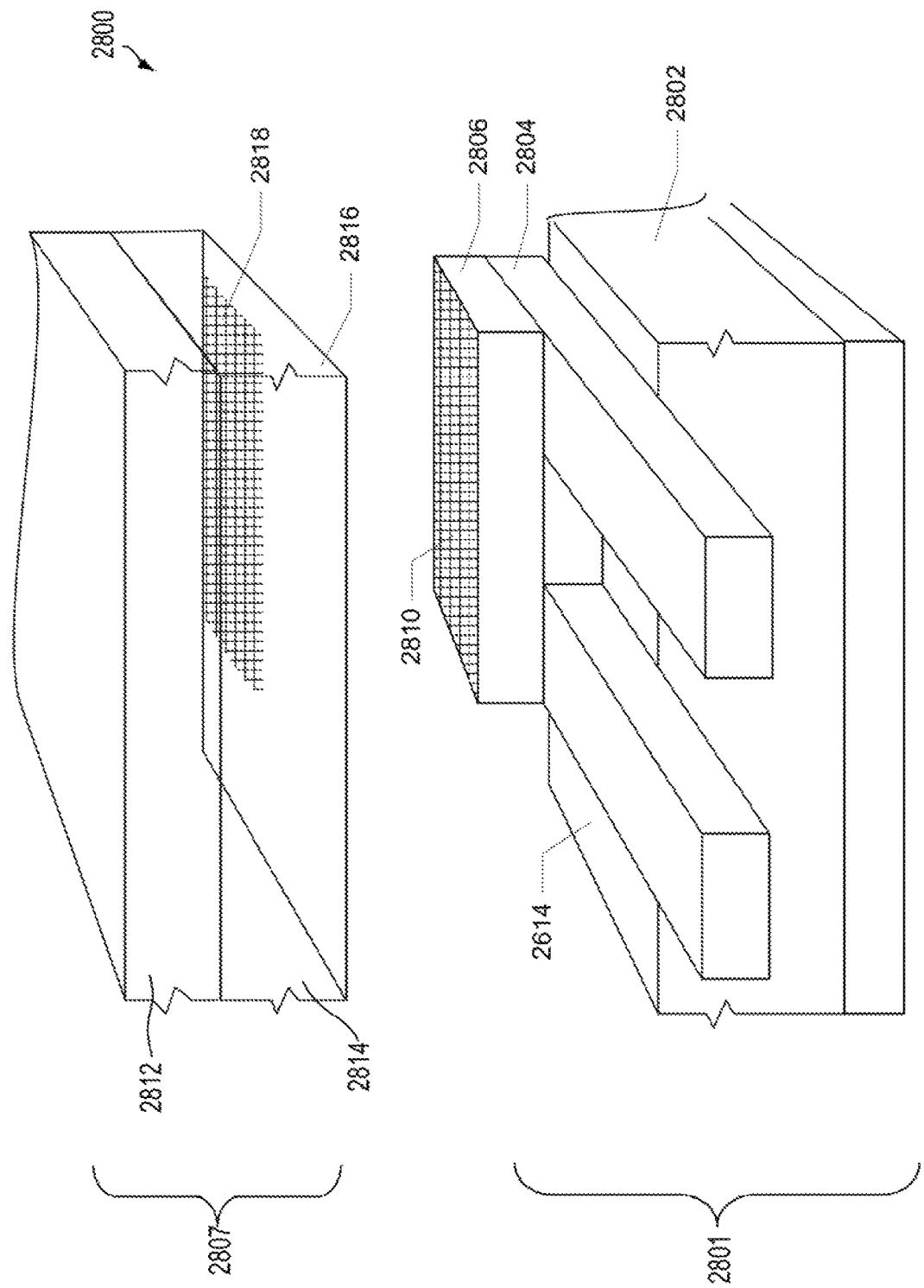
FIG. 28B illustrates a perspective view of a portion of the lid and base structure of the transdermal sampling and analysis device shown in FIG. 28A.

FIGS. 28A and 28B illustrate different views of example components that may be formed as a result of method 2700 and that, when joined together, create a device 2800. FIG. 28A shows a three-dimensional cross-section of a base structure of the device 2800. In device 2800 a first conductive material layer may be applied to a base substrate (not shown), and patterned to form components including at least a counter electrode 2802, corresponding to step 2402. Device 2800 may also have a photoresist material applied over the counter electrode 2802, corresponding to step 2702, which may be patterned to form channel support structures 2804 in a channel forming spacer layer, corresponding to step 2704.

A second spacer layer material may be applied over the channel forming spacer layer to form a recessed second spacer layer 2806, corresponding to step 2706 and, depending on the particular second spacer layer material, to optional step 2708. The degree to which the second spacer layer 2806 may be recessed back from the edge of the channel support structures 2804 in the channel forming spacer layer is shown by arrow 2808. The distance of arrow 2808 may be variable according to different embodiments. Also depending on the type of material used to create the second spacer layer 2806, an adhesive material may be selectively applied to the top surface 2810 of the second spacer layer 2806, corresponding to optional step 2710. For example, the second spacer layer material may be a double sided adhesive, thereby making an additional adhesive layer unnecessary. In various embodiments, the second spacer layer 2806 as well as the channel forming spacer layer may each be around 10-20 μm thick.

FIG. 28B illustrates a lid structure of device 2800 as well as the base structure 2801, and effect of the recessed second spacer layer in device 2800 compared to device 2600 discussed above with respect to FIG. 26. A lid structure 2807 may have a lid substrate 2812 to which a second conductive material layer may be applied, corresponding to step 2410. The second conductive material layer may be patterned to form a working electrode 2814, corresponding to step 2412. A layer of the analyte sensing reagent (not shown) may be applied to the surface of the working electrode 2814, corresponding to step 2414.

As shown by the base structure 2801 of device 2800, while the exposed areas 2614 on the counter electrode 2802 are still defined by channel support structures 2804, similar to device 2600, such channel support structures 2804 do not limit the exposed areas of the working electrode 2814. Rather, the recessed second spacer layer 2806 serves to raise the working electrode 2814 off of the channel support structures 2804, thereby providing an exposed area 2816 on the working electrode that is much larger than exposed area 2616 of device 2600. For example, in comparison to the direct contact between the top surface 2603 of the channel support structures and the working electrode in contact area 2618 of device 2600, the only direct contact to the working electrode 2814 of device 2800 is by the top surface 2810 of the recessed spacer layer 2806. As a result, device 2800 may have a smaller corresponding contact area 2818 on the working electrode 2814. The larger exposed areas of the 2816 of the working electrode may provide a stronger signal and/or allow for use of a smaller working electrode to produce the same level of result.

Glucose oxidase (GOD), an enzyme prototype, may be absorbed electrochemically onto a polypyrrole (PPy) layer using a potentiostat together with an electrolyte solution consisting of 0.1 M, each, of PPY and KCl at 0.8 V for 2 minutes. 0.1 M Ferricyanide and 8001 units/ml of GOD (18 µl GOD and 48 µl $K_2FeCN_6$ in 10 ml phosphate buffer solution) may be further added in the electrolyte solution for the deposition of GOD. Selective deposition of PPy+GOD may be then done on one of the exposed electrodes of the transdermal sampling and analysis device 200. Chronoamperometric dose responses may be recorded and the results reveal that the sensor has a good linearity from 0 to 10 mM glucose with the sensitivity of 2.9 mA/mM. For the lactate sensor chips, the same process may be used except lactate oxidase was substituted for the GOD.

In an embodiment the transdermal sampling and analysis device 200 may be used to deliver substances into the capillary-like channels of the skin 100. A substance may be loaded on the transdermal sampling and analysis device 200, preferably in an encapsulation. Heat applied to the skin creates capillary-like channels in the stratum corneum. The substance may then be delivered transdermally into the body through the capillary-like opening in the skin. Positive pressure may be required to deliver the substance into the body as interstitial fluid exits the body.

The transdermal sampling and analysis device 200 of the various embodiments may be packaged in a sealed and sterile container without any contaminants. The seal may be broken to access one transdermal sampling and analysis device 200 using an applicator. Once the transdermal sampling and analysis device 200 is taken out of the sealed packaging, it may be used as described above. The transdermal sampling and analysis device of the various embodiments may be disposable or reusable.

The transdermal sampling and analysis device 200 of the various embodiments may have a variety of different uses including monitoring for viability and functionality of organs and tissues prepared and stored for surgical implantations; monitoring entire chemical panels for individuals, patients, or populations at risk; monitoring for critical care, shock, trauma and resuscitation; monitoring for chronic critical diseases; monitoring for early detection of diseases; monitoring for response to therapeutic treatments; and gene therapy.

The transdermal sampling and analysis device 200 of the various embodiments may also be used to analyze biological samples that have already been collected from samples such as food, water, air, whole blood, urine, saliva, chemical reactions or cultures.

Figure 29A:
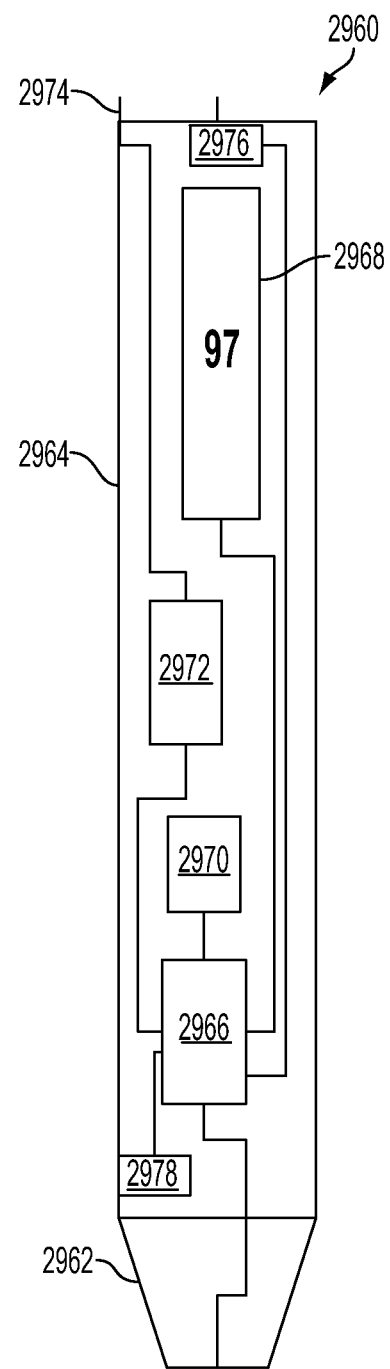
FIG. 29A is a component block diagram of an embodiment applicator device for applying the transdermal sampling and analysis device.

The transdermal sampling and analysis device 200 of the various embodiments may be applied to the skin 100 of a subject using an applicator device. The applicator device may be configured to take different shapes and designs. In an exemplary embodiment, as illustrated in FIG. 29A, the applicator device 2960 may be configured to have a cylindrical design with a head 2962 and a body 2964. The head 2962 may be configured to engage an embodiment transdermal sampling and analysis device 200 and couple it to both a voltage source as well as to a sensing unit and display. A voltage source 2978 may be provided in the form of a battery or an alternating current adapted to accept an alternating current voltage signal. For example, a user may load the applicator device 2960 by picking-up a transdermal sampling and analysis device 200 for measuring body parameters and unloading by discarding the transdermal sampling and analysis device 200 when the required parameters may be obtained or when the transdermal sampling and analysis device 200 is no longer functional.

The body 2964 may include a processor 2966 coupled to a display monitor 2968 for displaying data to the user, a memory 2970 for storing processed data received from the transdermal sampling and analysis device 200, and a transceiver 2972 for transmitting information from the applicator device 2960 or for receiving data. The processor 2966 may also include a digital signal processor which modifies the voltage source to produce a voltage signal having the appropriate duty cycle before application across the terminals of the embodiment disruptor. The body 2964 may also include an antenna 2974, used to transmit and receive radio frequency signals, coupled to the transceiver 2972. Alternatively, the applicator 2960 may include a data communication port 2976 such as USB or FireWire® which enables the applicator to transfer data over a communication cable to another device.

The processor 2966 may be configured by software to receive signals from the transdermal sampling and analysis device 200 and convert the signals to user ascertainable information. The user ascertainable information may be displayed on the display monitor 2968. The processed data may be stored in memory 2970. For example, if the transdermal sampling and analysis device 200 is configured to determine blood glucose levels, the applicator device 2960 may be configured to receive electrical signals generated by the transdermal sampling and analysis device 200 and convert the signals, using the processor 2966, to user ascertainable information such as a numeric glucose level. The information may be stored in the memory 2970. The numeric glucose level may be displayed on the display monitor 2968. In this example, the blood glucose levels are measured to be "97" which is displayed in the display monitor 2968.

The body 2964 may further include a transceiver 2972 coupled to the processor 2966 and an antenna 2974 to wirelessly transmit data to other devices or receive data. For example, the applicator device 2960 may transmit data obtained from a subject to a remote server. The applicator device 2960 may store the processed data in memory 2970 and transmit the data either continuously or intermittently to other devices.

Figure 29B:
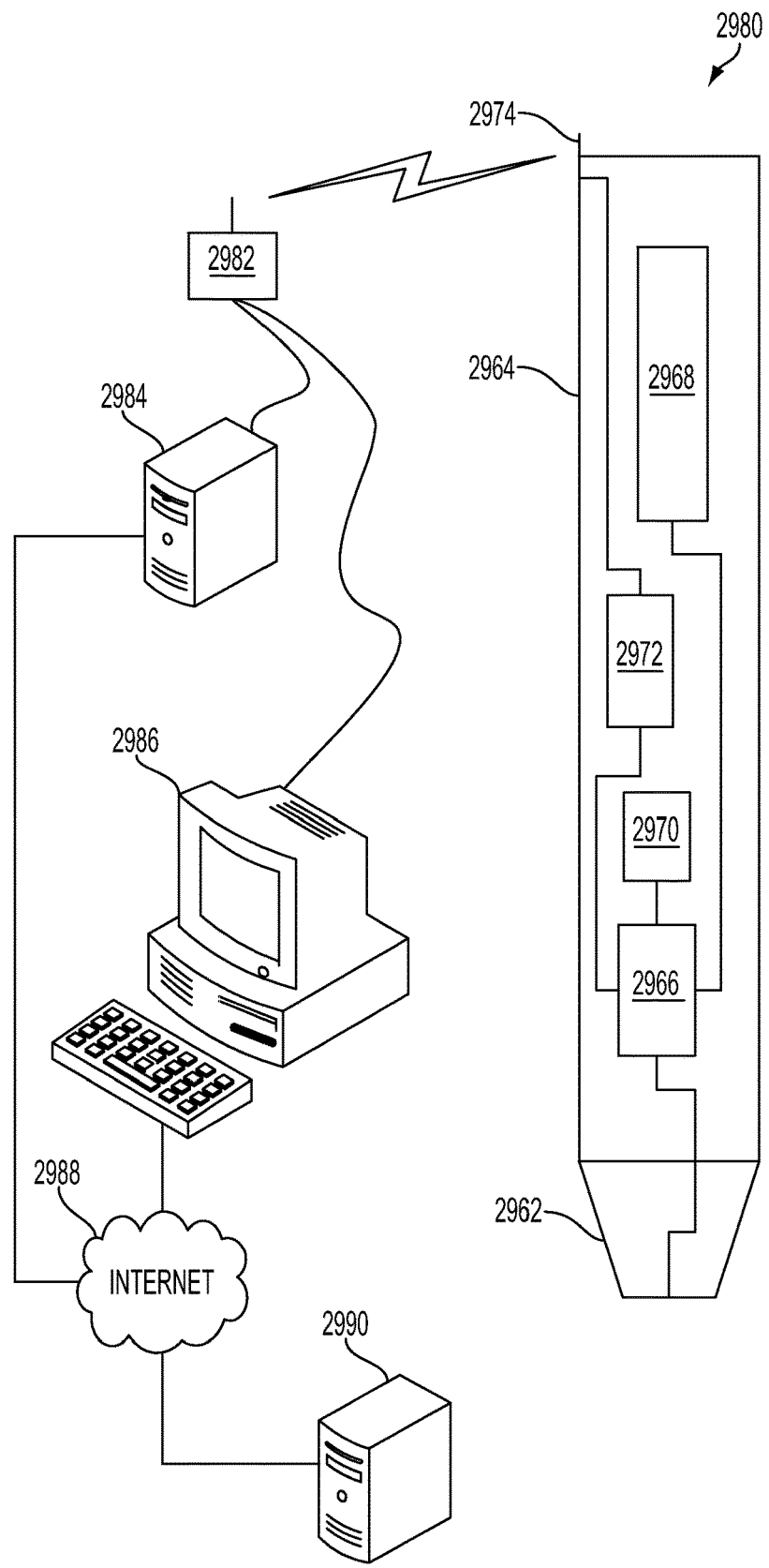
FIG. 29B is a system component diagram of a transdermal sampling and analysis device system according to an embodiment.

FIG. 29B illustrates a component block diagram for a transdermal sampling and analysis device system 2980 according to an embodiment. Once the data is collected by the transdermal sampling and analysis device and the applicator device 2960, the data may be transmitted to the other components of the transdermal sampling and analysis device system 2980 for storage/analysis. For example, the data may be transmitted to an external transceiver 2982 which in turn may relay the data to a remote server 2984 for storage and/or analysis. The remote server 2984 may receive and store the transmitted information as part of the subject's records, such as medical records; or the server 2984 may be configured to receive the data for conducting research. In an alternative example, the server 2984 may include a built-in transceiver using which it may receive and/or transmit data wirelessly.

In a further embodiment, data received and stored by an applicator device 2960 may be transmitted to a remote computing device 2986. The remote computing device 2986 may receive and store the transmitted data and display it on the monitor and/or perform further analysis of the data.

The remote devices (i.e., server 2984 and computing device 2986) may communicate with other remote devices, such as server 2990 by using different communication means such as the Internet 2988. For example, information received from the transdermal sampling and analysis device 200 may be transmitted to the remote devices using the applicator device 2960. The remote devices may in turn transmit data to other devices via the Internet 2988 for storage or further analysis.

Figure 29C:
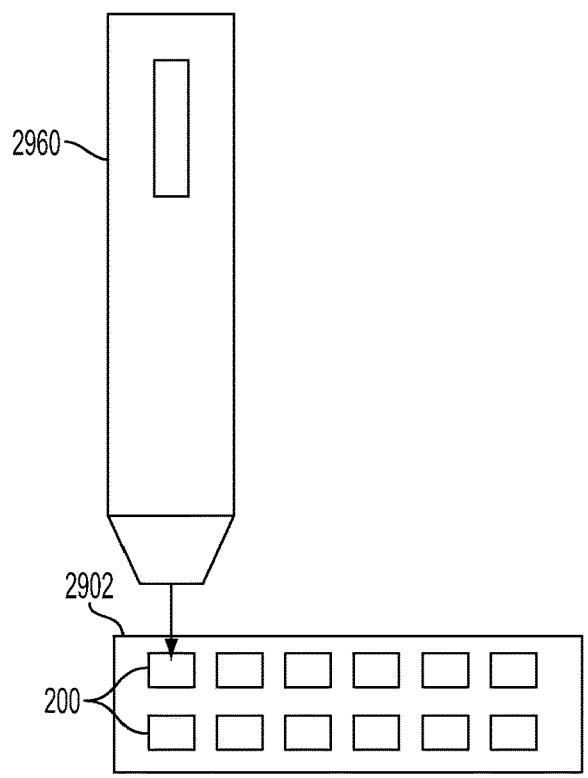
FIGS. 29C-29E illustrate embodiment methods for loading an embodiment applicator device with transdermal sampling and analysis devices using different kits.

In an exemplary embodiment, as illustrated in FIG. 29C, several transdermal sampling and analysis devices 200 may be arranged in a sterile kit 2902. In this example, the transdermal sampling and analysis devices 200 may be arranged next to one another, each in a sterile compartment, in the kit. The applicator device 2960 may be configured to load one transdermal sampling and analysis device 200 at a time from different compartments of the kit 2902 to ensure that the additional transdermal sampling and analysis devices 200 remain sterile and ready for future use.

Figure 29D:
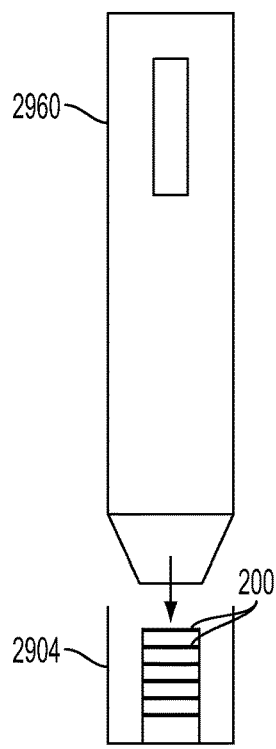

In a further embodiment, as illustrated in FIG. 29D, the transdermal sampling and analysis devices 200 may be arranged in a sterile stack in a kit 2904 that may be cylindrical in shape. In this example, the applicator device 2960 may be configured to load by contacting the applicator device 2960 to the transdermal sampling and analysis device 200 which may be at the top of the sterile stack in the kit 2904. The transdermal sampling and analysis devices 200 may be stacked directly on top of one another in the kit 2904 or may be separated by a separator material. As transdermal sampling and analysis devices 200 may be used to obtain a biological sample, the transdermal sampling and analysis device 200 may be ejected from the applicator device and disposed above.

Figure 29E:
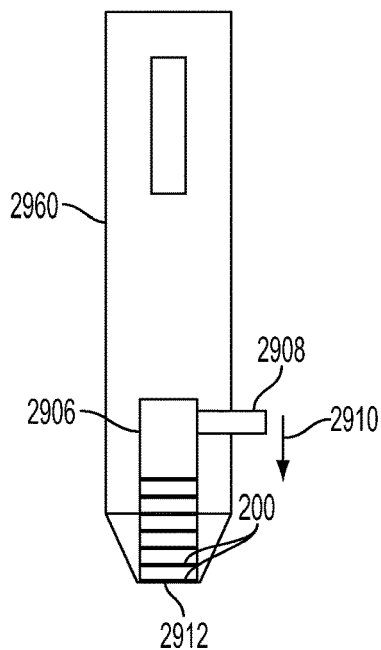

FIG. 29E illustrates a further embodiment method for loading and unloading transdermal sampling and analysis devices 200 on the applicator device 2960. In this embodiment, a kit cartridge 2906 including several transdermal sampling and analysis devices 200 stacked in a vertical configuration may be loaded on to the applicator device 2960. The applicator device 2960 may have a lever 2908 which may allow the user to load or unload transdermal sampling and analysis devices 200 onto the tip 2912 of the applicator device 2960. For example, once the kit cartridge 2906 is may be loaded onto the applicator device 2960, the user may push down the lever 2908 in the direction of the arrow 2910 to load the tip 2912 of the applicator device 2960 with a transdermal sampling and analysis device 200. Once the transdermal sampling and analysis device 200 is used up, it may be unloaded by simply pushing it out of the applicator device 2960 by pushing the lever 2908 in the direction of the arrow 2910 and discarding it. This process may continue until the last transdermal sampling and analysis device 200 is used. Once the last transdermal sampling and analysis device 200 is used, the kit cartridge 2906 may be changed with one that includes new transdermal sampling and analysis devices 200.

Figure 30:
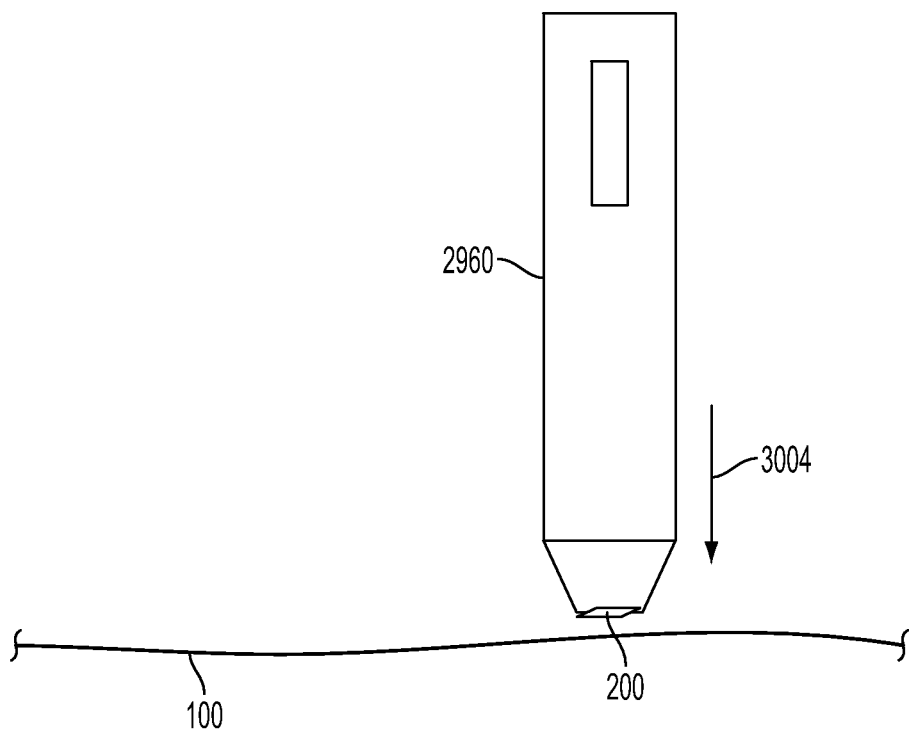
FIG. 30 illustrates an embodiment method of applying a loaded applicator device to the skin of a subject.

In an embodiment illustrated in FIG. 30, after loading an applicator device 2960 with a transdermal sampling and analysis device 200 from a kit 2902, 2904, 2906 the applicator device 2960 may apply the transdermal sampling and analysis device 200 to the skin 100 of a subject. The transdermal sampling and analysis device 200 may be applied to the skin 100 by moving the applicator device 2960 in the direction of the arrow 3004 towards the skin 100. Once in contact with the skin 100, the transdermal sampling and analysis device 200 may draw interstitial fluid and generate signals which may be transmitted to a processor.

Figure 31:
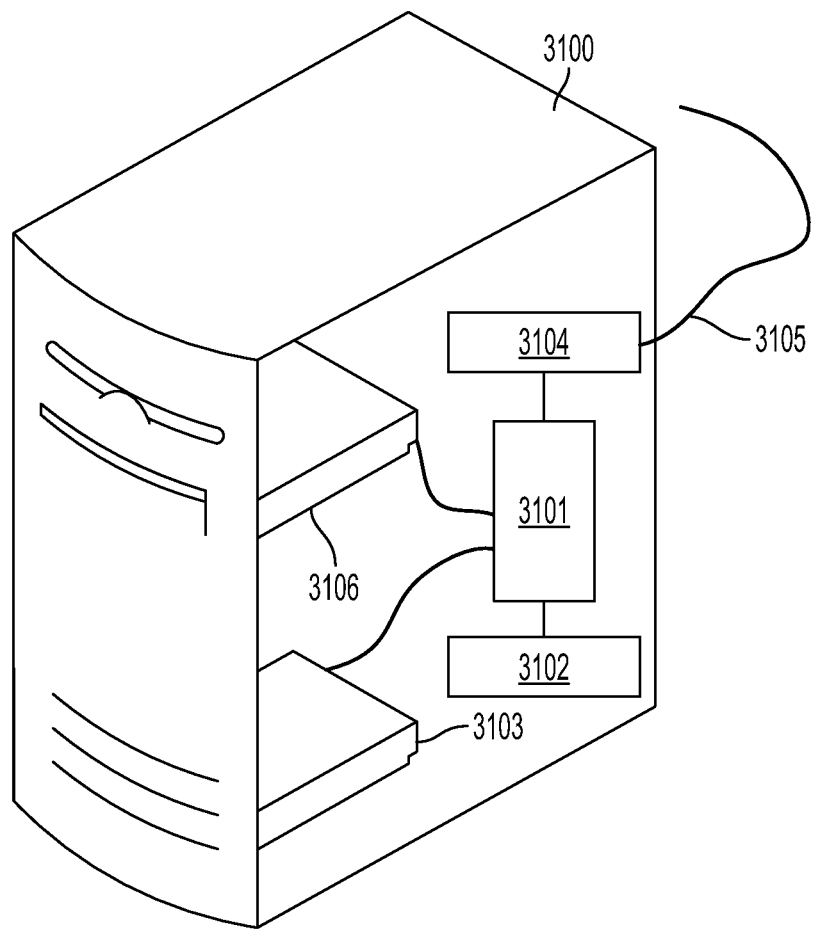
FIG. 31 is a component block diagram of a server suitable for use in the various embodiments.

A number of the embodiments described above may be implemented with any of a variety of remote server devices, such as the server 3100 illustrated in FIG. 31. Such a server 3100 typically includes a processor 3101 coupled to volatile memory 3102 and a large capacity nonvolatile memory, such as a disk drive 3103. The server 3100 may also include a floppy disc drive and/or a compact disc (CD) drive 3106 coupled to the processor 3101. The server 3100 may also include a number of connector ports 3104 coupled to the processor 3101 for establishing data connections with network circuits 3105.

Figure 32:
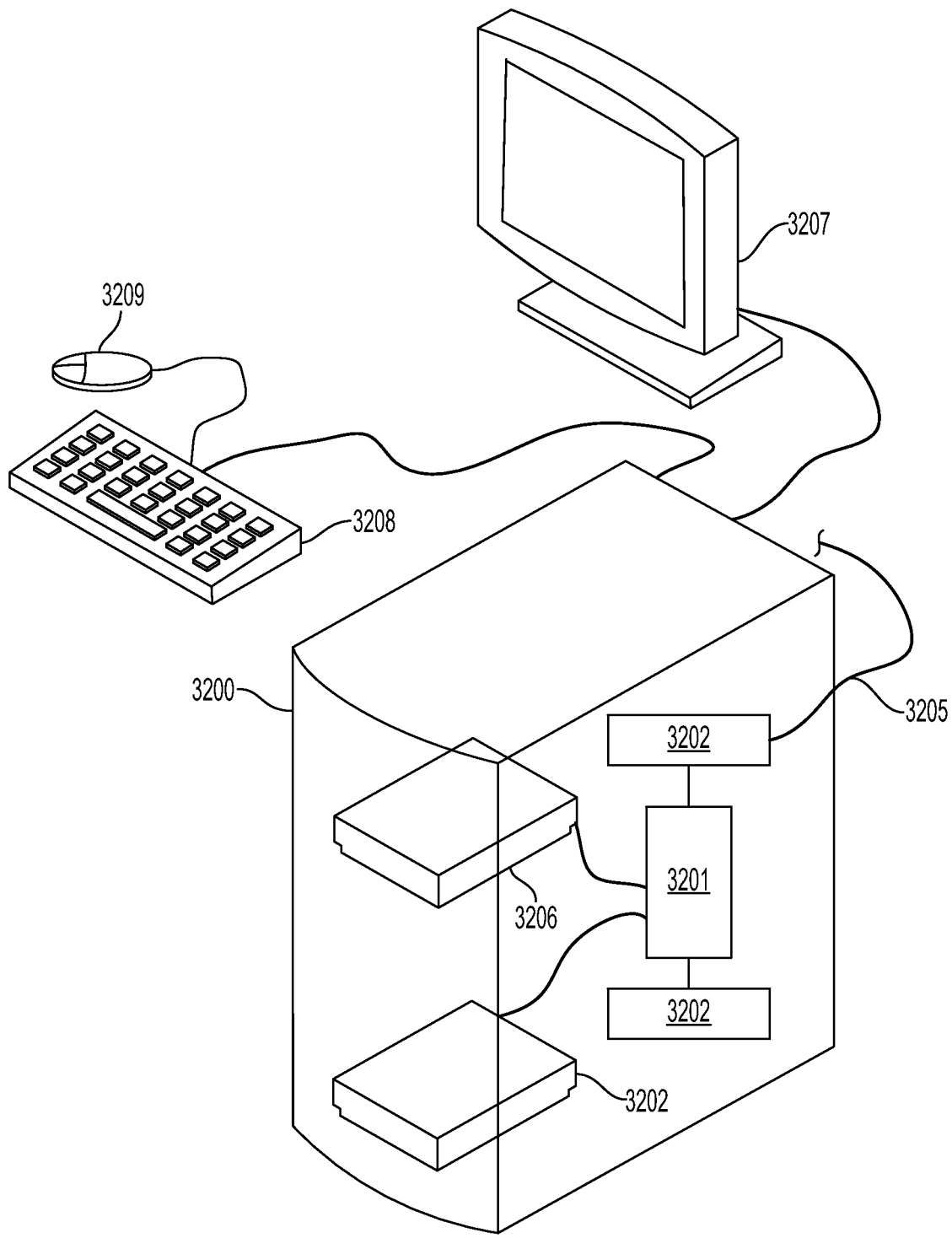
FIG. 32 is a component block diagram of a computer device suitable for use in the various embodiments.

The embodiments transdermal sampling and analysis device data described above may also be transmitted or coupled to any of a variety of computers, such as a personal computer 3200 illustrated in FIG. 32, for further monitoring, storage or manipulation. Such a personal computer 3200 typically includes a processor 3201 coupled to volatile memory 3202 and a large capacity nonvolatile memory, such as a disk drive 3203. The computer 3200 may also include a floppy disc drive and/or a compact disc (CD) drive 3206 coupled to the processor 3201. Typically the computer 3200 will also include a pointing device such as a mouse 3209, a user input device such as a keyboard 3208 and a display 3207. The computer 3200 may also include a number of network connection circuits 3204, such as a USB or Fire-Wire®, coupled to the processor 3201 for establishing data connections to the applicator 2960. In a notebook configuration, the computer housing includes the pointing device 3209, keyboard 3208 and the display 3207 as is well known in the computer arts.

The processor 2966, 3101, 3201 may be any programmable microprocessor, microcomputer or multiple processor chip or chips that can be configured by software instructions (applications) to perform a variety of functions, including the functions of the various embodiments described herein. In some mobile devices, multiple processors 2966, 3101, 3201 may be provided, such as one processor dedicated to wireless communication functions and one processor dedicated to running other applications. Typically, software applications may be stored in the internal memory 2970, 3102, 3202 before they are accessed and loaded into the processor 2966, 3101, 3201. In some mobile devices, the processor 2966, 3101, 3201 may include internal memory sufficient to store the application software instructions. The internal memory of the processor may include a secure memory (not shown) which is not directly accessible by users or applications and that may be capable of recording MDINs and SIM IDs as described in the various embodiments. As part of the processor, such a secure memory may not be replaced or accessed without damaging or replacing the processor. In some devices 200, 3100, 3200, additional memory chips (e.g., a Secure Data (SD) card) may be plugged into the device and coupled to the processor 2966, 3101, 3201. In many devices, the internal memory 2970, 3102, 3202 may be a volatile or nonvolatile memory, such as flash memory, or a mixture of both. For the purposes of this description, a general reference to memory refers to all memory accessible by the processor 2966, 3101, 3201, including internal memory 2970, 3102, 3202, removable memory plugged into the device, and memory within the processor 2966, 3101, 3201 itself, including the secure memory.

The various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality may be implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a computer-readable medium. The steps of a method or algorithm disclosed herein may be embodied in a processor-executable software module executed which may reside on a tangible non-transitory computer-readable medium or processor-readable medium. Non-transitory computer-readable and processor-readable media may be any available media that may be accessed by a computer or processor. By way of example, and not limitation, such computer-readable media may comprise RAM, ROM, EEPROM, CD-ROM or other optical disk storage, magnetic disk storage or other magnetic storage devices, or any other medium that may be used store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

While the invention has been described in detail with respect to specific embodiments thereof, it will be apparent to those skilled in the art that various alterations, modifications and other changes may be made without departing from the scope of the embodiments described herein. It is therefore intended that all such modifications, alterations and other changes be encompassed by the claims. Further, any reference to claim elements in the singular, for example, using the articles "a," "an" or "the" is not to be construed as limiting the element to the singular.

What is claimed is:

1. A transdermal sampling and analysis device adapted to be placed on skin, the transdermal sampling and analysis device comprising:
   a substrate having a first side;
   at least one disruptor mounted on the first side of the substrate, wherein the at least one disruptor is configured to generate a localized heat capable of altering permeability characteristics of barrier cells of an organism to become permeable when a voltage is applied across the at least one disruptor;
   a reservoir on the first side of the substrate, wherein the reservoir comprises:
      a circular collection portion configured to collect a biological sample that is obtained through permeable barrier cells, wherein the circular collection portion is substantially parallel to a plane of the skin; and
      a sensing chamber portion configured to receive the biological sample from the circular collection portion, wherein the sensing chamber portion surrounds a periphery of the circular collection portion such that the sensing chamber portion is concentric with the circular collection portion substantially parallel to the plane of the skin;
   a lid structure configured to enclose the reservoir;
   a biological sensing element comprising at least a first electrode and at least a second electrode, wherein the biological sensing element is configured to determine a level of an analyte in the biological sample;
   a first spacer layer disposed on the first side of the substrate; and a second spacer layer disposed over the first spacer layer, wherein the sensing chamber portion of the reservoir is configured to contain the biological sample between the at least first electrode and the at least second electrode.

2. The transdermal sampling and analysis device of claim 1, wherein the first spacer layer comprises a plurality of channel support structures that form a plurality of channels in the sensing chamber portion.

3. The transdermal sampling and analysis device of claim 2, wherein each of the plurality of channels in the sensing chamber portion comprise a channel height to width ratio of less than 20:1.

4. The transdermal sampling and analysis device of claim 3, wherein the channel height to width ratio is approximately 3:1.

5. The transdermal sampling and analysis device of claim 3, wherein the channel height to width ratio is approximately 1:1.

6. The transdermal sampling and analysis device of claim 3, wherein the channel height is between 80 and 500 µm.

7. The transdermal sensing and analysis device of claim 2, wherein the sensing chamber portion comprises a circular sensing chamber.

8. The transdermal sensing and analysis device of claim 2, wherein the second spacer layer is further configured to be recessed back from an edge of at least one of the plurality of the channel support structures of the first spacer layer.

9. The transdermal sampling and analysis device of claim 1, wherein the second spacer layer comprises a double-sided adhesive material that is pre-cut to form a shape recessed back from an edge of the first spacer layer.

10. The transdermal sampling and analysis device of claim 1, further comprising:

an adhesive layer on a top surface of the second spacer layer, wherein the adhesive layer is configured to adhere the lid structure to the second spacer layer.

11. The transdermal sampling and analysis device of claim 1, wherein a thickness of the first spacer layer is approximately equal to a thickness of the second spacer layer, wherein each of the first and second spacer layers are approximately 10-20 µm thick.

12. The transdermal sensing and analysis device of claim 1, wherein one or more of the first spacer layer and second spacer layer comprise a photoresist material.

13. The transdermal sensing and analysis device of claim 12, wherein the first spacer layer comprises a first photoresist material and the second spacer layer comprises a second photoresist material.

* * * * *